United States Patent [19]
Good

[11] Patent Number: 5,342,283
[45] Date of Patent: Aug. 30, 1994

[54] ENDOCURIETHERAPY

[76] Inventor: Roger R. Good, 302 Forest Dr., Bellevue, Nebr. 68005

[21] Appl. No.: 565,714

[22] Filed: Aug. 13, 1990

[51] Int. Cl.$^5$ .................................... A61N 5/00
[52] U.S. Cl. ............................................ 600/8
[58] Field of Search ............................ 600/1-8

[56] References Cited
U.S. PATENT DOCUMENTS

| | | |
|---|---|---|
| 4,702,228 | 10/1987 | Russell, Jr. et al. ........... 600/8 |
| 4,754,745 | 7/1988 | Horowitz ........................ 600/8 |
| 4,994,013 | 2/1991 | Suthanthiran et al. ......... 600/8 |

Primary Examiner—Lee S. Cohen
Assistant Examiner—J. P. Lacyk
Attorney, Agent, or Firm—Vincent L. Carney

[57] ABSTRACT

To provide versatile radioactive implants and methods of radiation therapy, plating methods such sputtering, as are used to coat single elements such as microspheres, wires and ribbons with radioactive metals, protective layers and identification layers. The resulting solid, radioactive, multilayered seamless elements are implanted individually or combined in intercavity applicators, with fabrics and in ribbons. Because they have selected half-lives and intensities, they provide flexibility in treatment, permitting low intensity or high intensity treatment, using temporary or permanent implants and implants with high intensity or low intensity or controured intensity to permit different therapies.

55 Claims, 13 Drawing Sheets

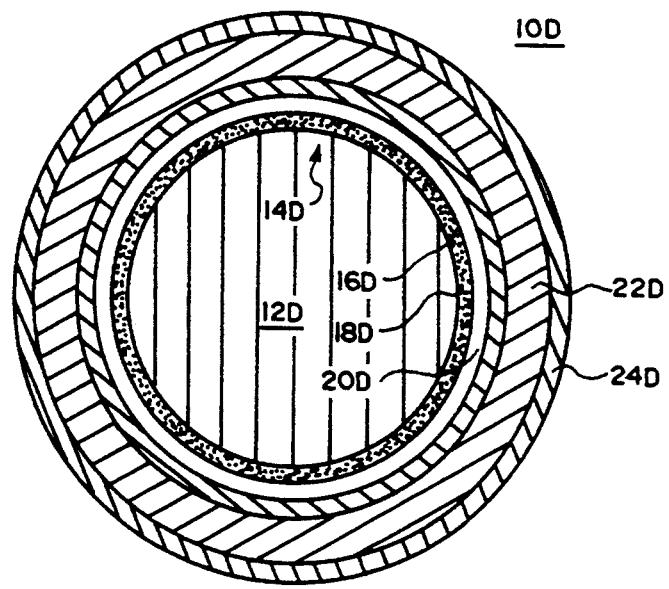
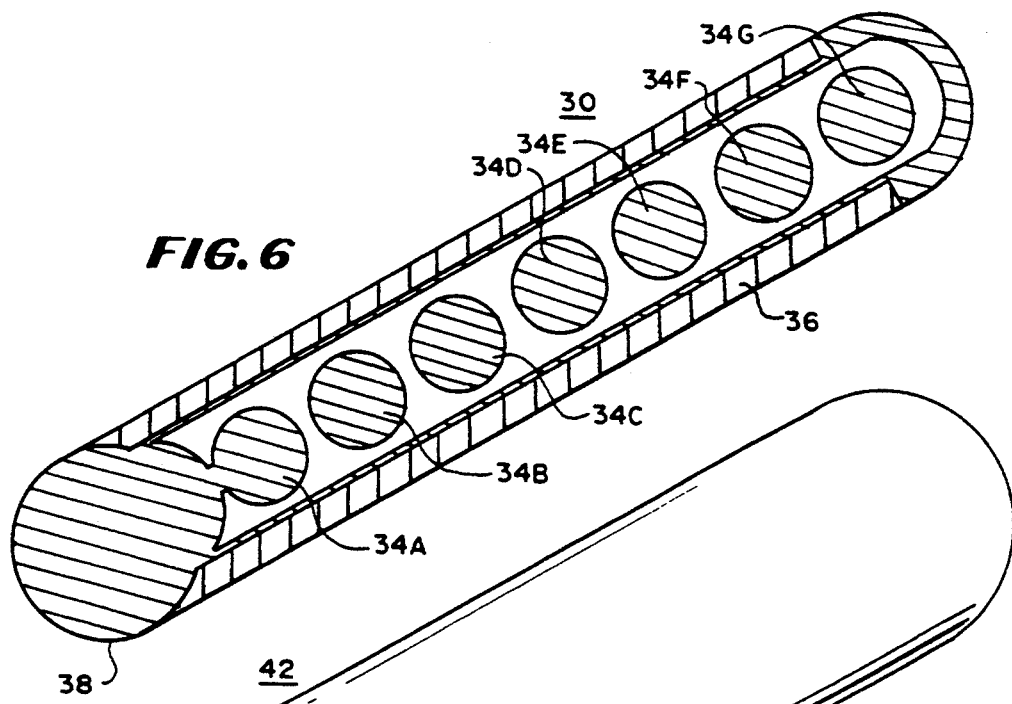
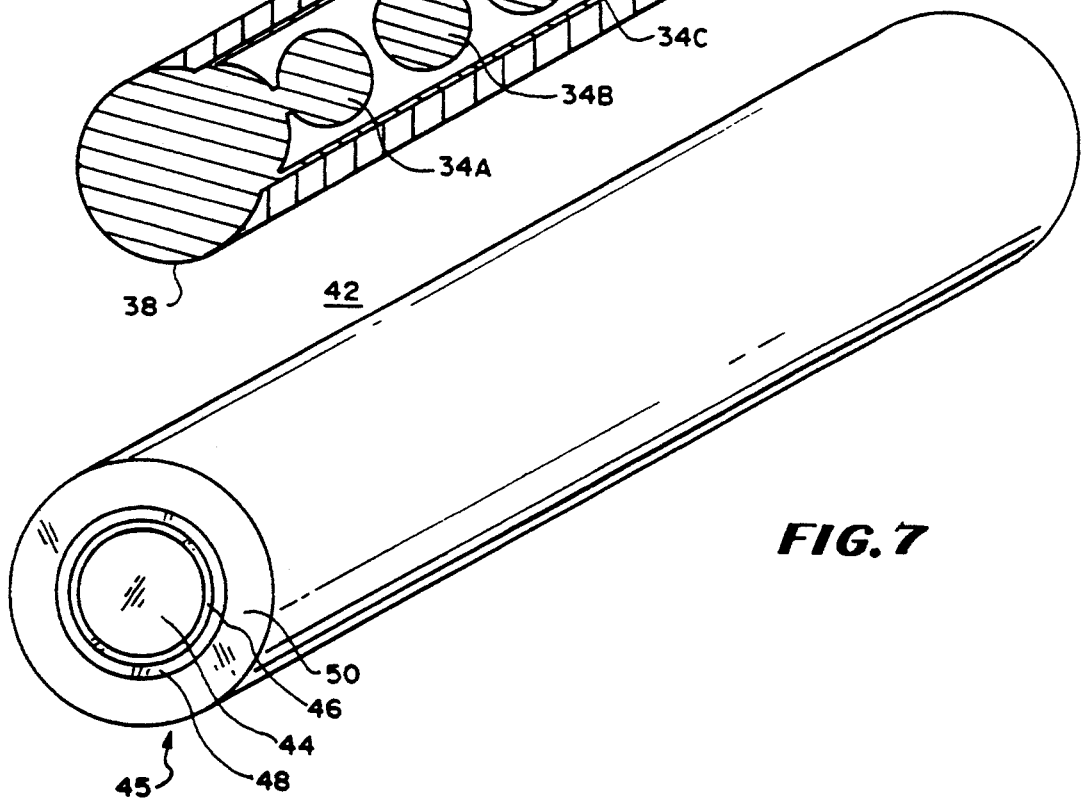

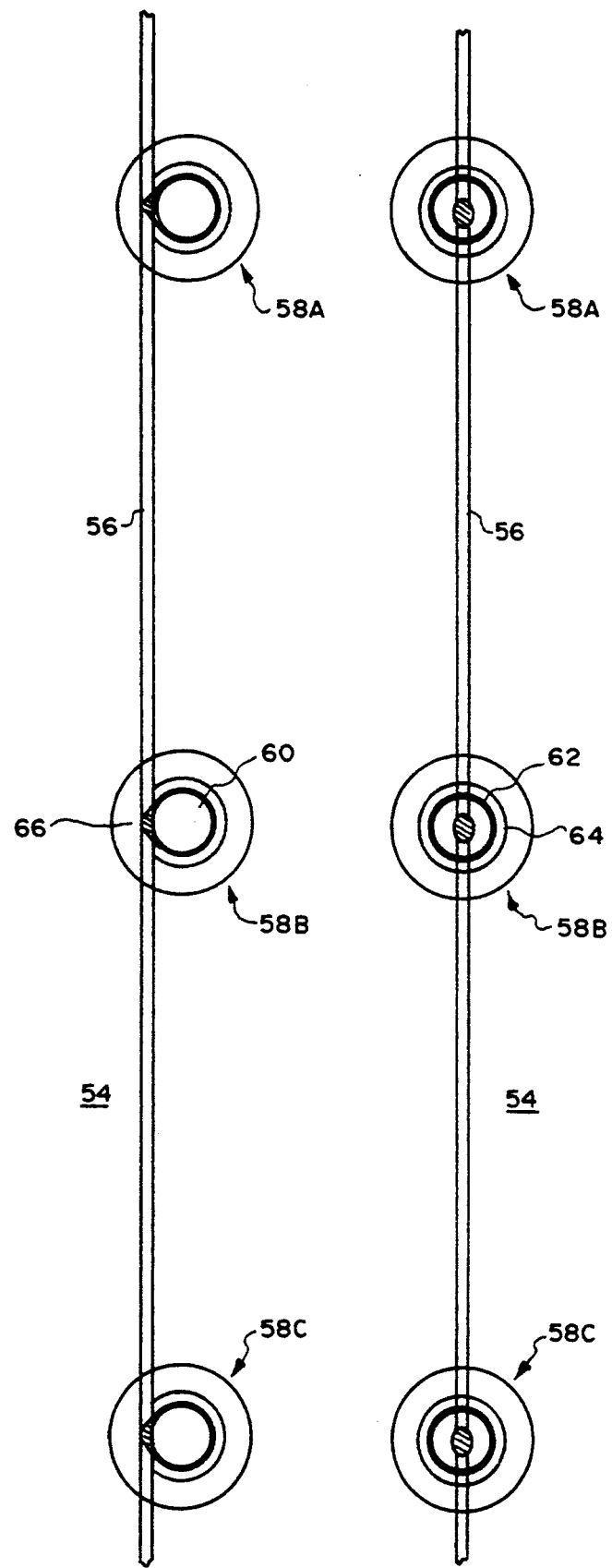

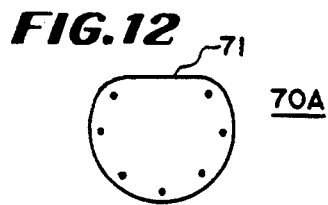
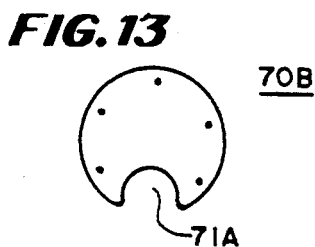
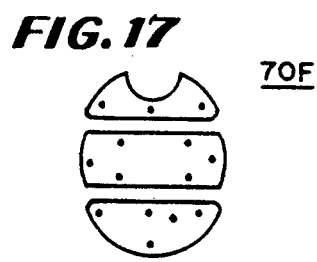
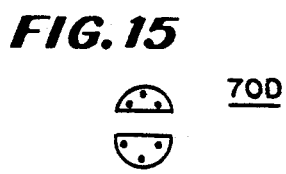
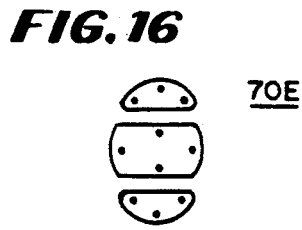
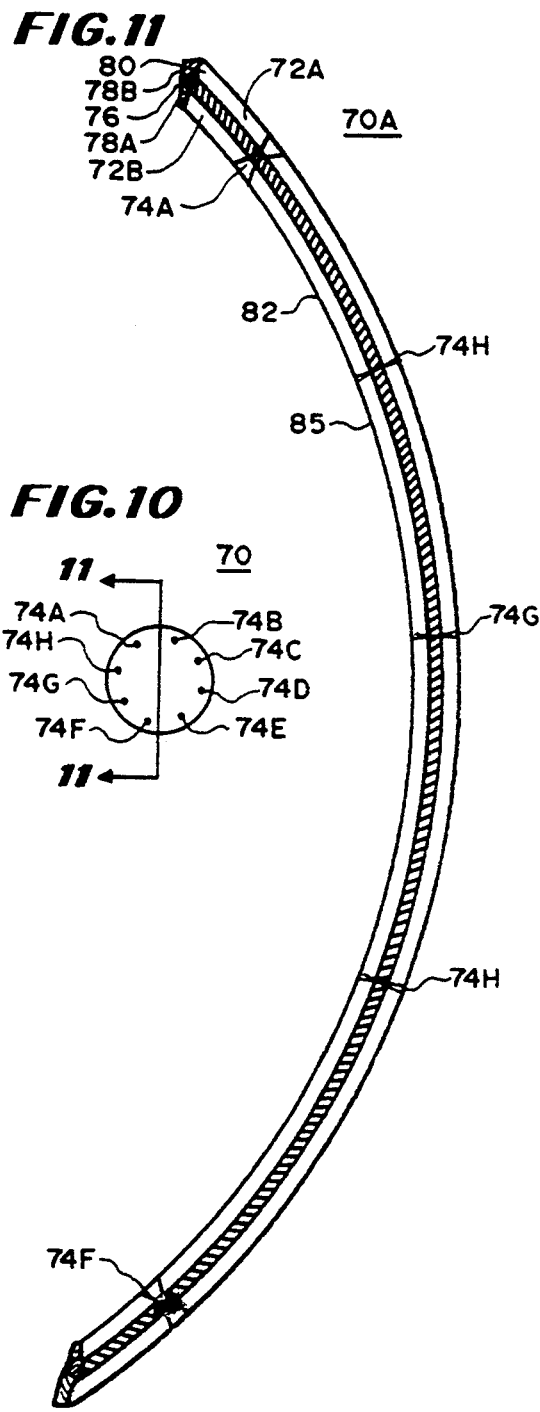

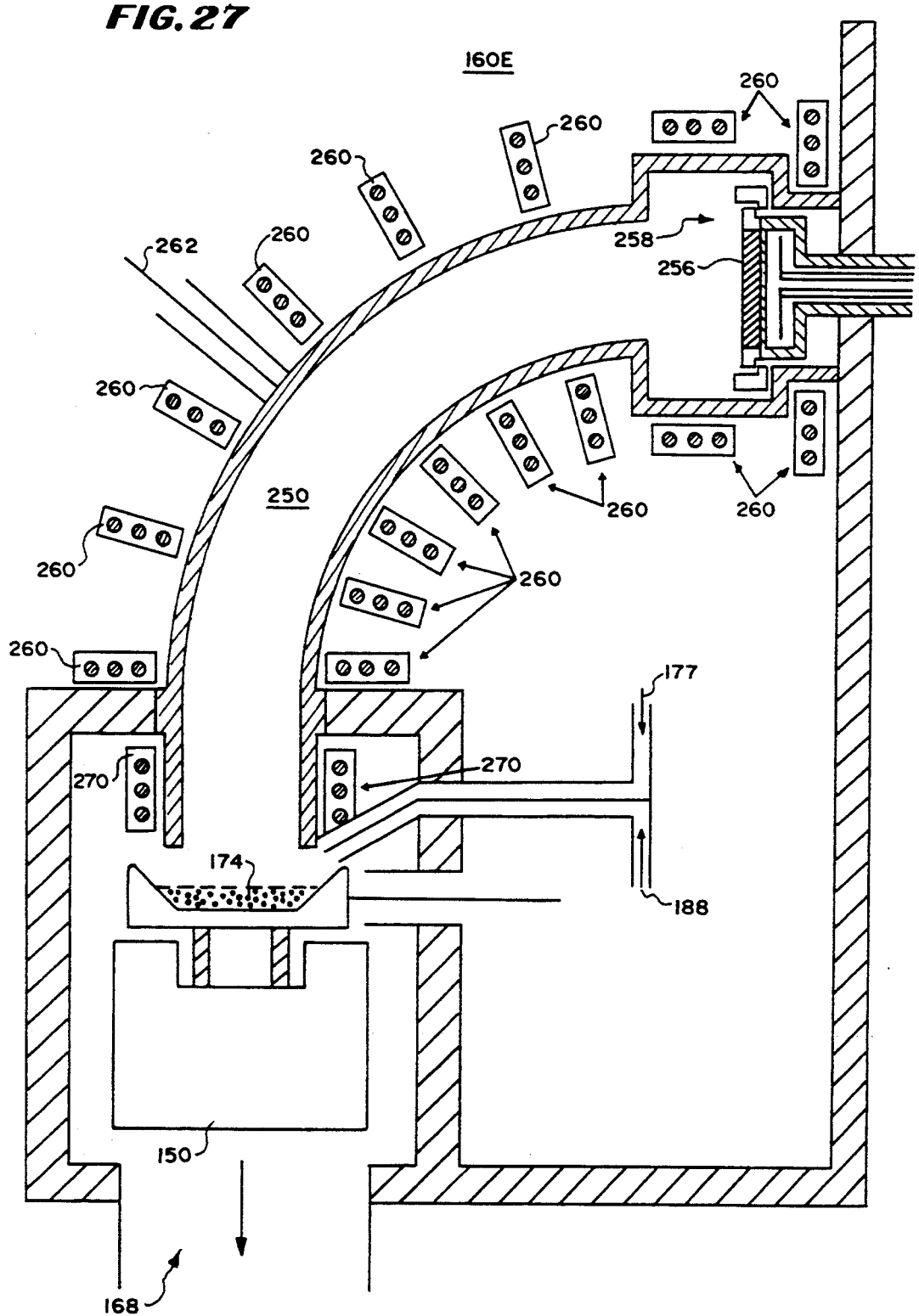

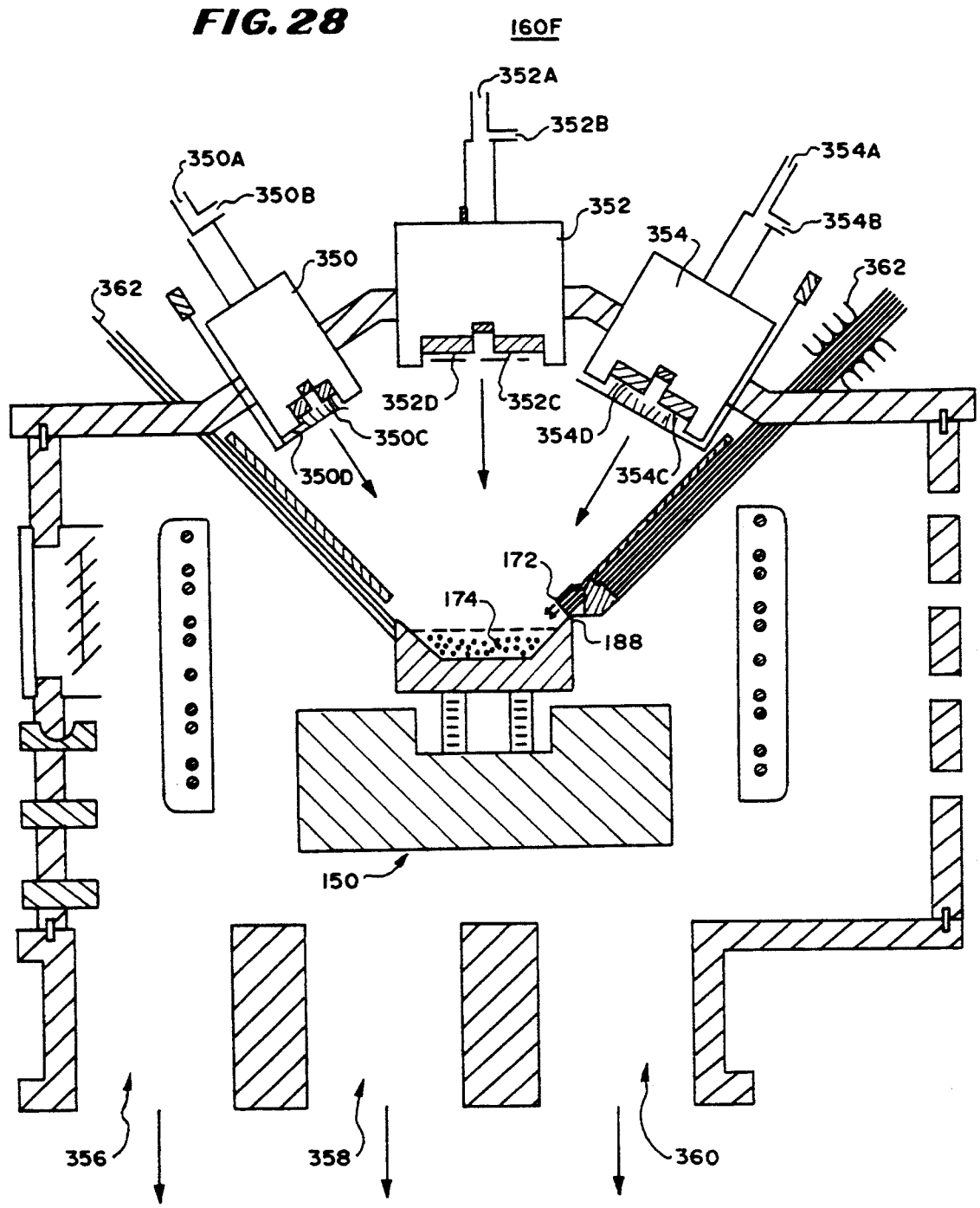

ENDOCURIETHERAPY

BACKGROUND OF THE INVENTION

This invention relates to radioactive implants, methods of making them and methods of using them.

It is known to use external beam supervoltage or megavoltage conventional fractionated radiation therapy to treat subclinical microscopic metastases in surgically undisturbed lymph node chains and to sterilize the postoperative tumor bed after the tumor is grossly excised. The uses of external beam radiation techniques have a disadvantage that they are not able to safely treat solid tumors because the solid tumors require an intensity of ratiation that is harmful to the surrounding normal tissue.

It is also known to implant radioactive sources directly into solid tumors for the destruction of the tumors in a therapy referred to as brachytherapy (short-range therapy). This therapy permits the application of larger does of radiation.

In the prior art brachytherapy, the sources are generally implanted for short periods of time and generally are sources of high radiation intensity. For example, radium needles and iridium-192 ribbons have been implanted into tumors (interstitial brachytherapy) or radium-226 capsules and cesium-137 capsules have been placed into body cavities such as the uterus (intracavitary brachytherapy).

The prior art interstitial brachytherapy treatment using radium needles has several disadvantages, such as for example: (1) dosimetry is difficult and imprecise; (2) local failures are caused, mainly by the large size of the radium needles (approximately the size of a lumber nail); (3) it is difficult to implant an adequate number of the needles uniformly throughout a tumor to produce homogeneous irradiation because they are large sources; and (4) the needles can only be left in place temporarily, and must be surgically removed.

It is known to implant iodine seeds temporarily or permanently. The prior art iodine seed consists of the radionuclide adsorbed onto a carrier which is placed into a metal tube that is welded shut. It has the disadvantages of: (1) being relatively large to be safely implanted in large numbers in the human body; and (2) due to its construction, producing inhomogeneous radiation.

The prior art iridium seeds in ribbon consist of solid iridium wire cut into pieces and placed in plastic tubing, which is then implanted into accessible tissues temporarily for several days. These seeds work well, but because they must be removed their application is limited to a few accessible body sites. Also, they only come in one energy.

The prior art radium-226 intracavitary sources and cesium sources consist of metal cylinders containing radium salts or cesium. The have several disadvantages, such as for example: (1) dosimetry is difficult and imprecise; (2) they are bulky and difficult to use; (3) it is difficult to implant or otherwise insert an adequate number of the cylinders in the proper locations to produce homogeneous irradiation because they are large sources; (4) the cylinders can only be left in place temporarily, and under some circumstances, must to be surgically removed; and (5) general anesthesia is required to dilate the cervix sufficiently to place a source in the uterus.

The applications of brachytherapy are still severely limited by the unavailability of a wide range of implantable radioactive sources that have a wide range of gamma energies (radiation energy is related to the volume irradiated) and varying half-lives (radionuclide half-life affects tumor dose rate, radiobiology, and normal tissue effects). Also the limited number of sources currently available are still physically unsatisfactory in their construction. There are few low energy limited lifetime radioactive seeds such as gold-198 and iodine-125 seeds that may be permanently implanted into solid cancers.

It is also known to apply heat to tumors by implanting metals that may be heated by radio frequency radiation and to move heatable or radioactive members about magnetically for positioning them without excessive surgery. This is especially significant in the treatment of highly vascular tumors. The existing hyperthermia radio frequency treatment is not well adapted for easy combination with endocurietherapy.

SUMMARY OF THE INVENTION

Accordingly, it is an object of the invention to provide novel radioactive implants.

It is a further object of the invention to provide novel techniques for manufacturing radioactive implants.

It is a still further object of the invention to provide novel techniques for using radioactive implants.

It is a still further object of the invention to improve the physical characteristics and manufacturing techniques of the radioactive seed used for implantation and treatment of human solid tumors (endocurietherapy).

It is a still further object of the invention to provide techniques for manufacture of radioactive seeds containing a wide variety of radionuclides with different energies and half-lives.

It is a still further object of the invention to provide techniques for manufacturing a wide variety of radionuclides including those useful for permanent implantation into human tissues, those useful for temporary removable interstitial needle or ribbon implantation into human tissues, and those useful for temporary intracavitary irradiation.

It is a still further object of the invention to mass manufacture microspherical seeds less than 0.40 millimeter in diameter that may contain a therapeutic amount of radioactivity, a hard tissue-compatible protective coat, and several special purpose coats.

It is a still further object of the invention to provide a novel electron-producing beta-seed.

It is a still further object of the invention to provide a novel technique for manufacture of multiple radioactive seeds connected by a ribbon or wire to facilitate rapid implantation of multiple seeds.

It is still further object of the invention to provide a novel technique for manufacture of multilayered radioactive wires that contain a wide variety of different radionuclides for use in temporary removable tumor implants.

It is a still further object of the invention to provide a novel tissue-compatible (absorbable and non-absorbable) surgical fabric that contains multiple radioactive seeds to facilitate rapid implantation of a large number of radioactive seeds.

It is a still further object of the invention to manufacture a novel small-diameter (less than one millimeter) high-activity intracavitary source using any of a variety of different radionuclides.

It is a still further object of the invention to present a novel method for incorporation of a radionuclide into a seed during manufacture of the seed.

It is a still further object of the invention to provide a novel method for incorporation of a nonradioactive elemental isotope into a seed during manufacture of a seed that will later form the desired radioactive isotope when the finished seed is bombarded with neutrons.

It is a still further object of the invention to provide a novel technique for eliminating the radiation dose anisotropy problems characteristic of the tungsten end-welded cylindrical radioactive seeds.

It is a still further object of the invention to provide a radioactive seed having a shape that is spherical rather than cylindrical to make it less likely to jam in an auto-feeding tissue implantation gun.

It is a still further object of the invention to provide a method for making a perfectly spherical titanium casing over a radioactive microspherical substrate when the radioactive material produces low energy gamma rays.

It is a still further object of the invention to provide a perfectly spherical tantalum, tungsten, gold, platinum casing or compound tungsten carbide, tantalum carbide casing over a radioactive microspherical substrate when the radioactive material produces high energy gamma rays.

It is a still further object of the invention to provide a perfectly spherical titanium, hafnium or zirconium metal casing or a compound casing of titanium carbide, titanium nitride, titanium conbonitride, hafnium nitride or zirconium nitride over a radioactive microspherical substrate when the radioactive material produces low energy gamma rays.

It is a still further object of the invention to provide a perfectly spherical diamond casing over a radioactive microsphere when the radioactive material produces beta rays.

It is a still further object of the invention to reduce the danger of radioactive contamination of the hospital environment.

It is a still further object of the invention to reduce the danger of case rupture of the radioactive seed by eliminating the free space between the radioactive component and the casing.

It is a still further object of the invention to increase the clinical utility and safety of the radioactive seed by making it significantly smaller in diameter to permit tissue implantation with thinner gauge needles.

It is a still further object of the invention to improve upon the uniformity of the radioactive coating used in radioactive seed production.

It is a still further object of the invention to provide a less expensive seed by eliminating the need for human or mechanical assembly of separate parts and welding of individual seeds.

It is a still further object of the invention to reduce the danger of radiation exposure to personnel involved in seed assembly.

It is a still further object of the invention to provide an effective low cost method for large-scale mass-manufacture of high quality radioactive seeds for use in implantation of human tissues and to make the seeds readily available for use in large numbers of patients on a daily basis.

It is still further object of the invention to provide means of modified manufacturing processes which allows great versatility in manufacturing seeds of a variety of designs containing different combinations of types of radionuclides, metal and alloy coatings, and elemental nonmetallic as well as compound hard coatings.

It is a still further object of the invention to produce a radioactive seed which contains multiple coating layers which have specialized purposes.

It is a still further object of the invention to produce a radioactive seed which contains a diffusion barrier coat over the radionuclide layer.

It is a still further object of the invention to produce a radioactive seed which contains a coat that enables visualization of the seed in tissue such as by magnetic resonance imaging (NMR, MR) or X-ray or single positron resonance (SPECT) or positron emitting tomography (PET) or the like.

It is a still further object of the invention to produce radioactive seeds that contain different magnetic resonance imaging marker coat to enable separate individual identification of one type of seed from another type of seed when seeds containing different radionuclides are implanted into the same tumor.

It is a still further object of the invention to produce an outermost seed coating which reduces friction, adds coloring for seed type identification, increases hardness and durability, and increases tissue compatibility and corrosion resistance.

It is still further object of the invention to produce a novel low-energy permanent multilayered radioactive microsphere.

It is a still further object of the invention to provide a novel ribbon containing multiple low energy permanent multilayered radioactive microspheres.

It is a still further object of the invention to provide a novel multilayered low energy permanent or temporary radioactive wire that may be permanently or temporarily implanted into human tissues and that safely delivers low energy.

It is a still further object of the invention to provide a novel invention which safely delivers energy at levels less than or equal to 100 KeV average gamma energy to tumors at a low rate in less than 130 days to produce tumoricidal radiation doses that are 2.3 to 5.7 times higher than the maximum doses permissible with reasonable safety by modern megavoltage external beam radiation therapy techniques.

It is a still further object of this invention to produce a radioactive seed which has the clinical result of reducing the complication rate of treatment while increasing the local cure rate by allowing safe delivery of very high radiation doses to sol id human tumors.

It is a still further object of the invention to introduce a versatility of manufacturing process that permit manufacture of improved seeds which have varied physical characteristics including different average gamma radiation energies and different average lifetimes.

It is a still further object of the invention to provide a combination of manufacturing techniques that permit optimally matched seeds for the physical location and radiobiology of the tumor type or cancerous tissue they are designed to destroy.

It is still further object of the invention to produce an improved radioactive seed, ribbon containing multiple seeds, or radioactive wire which may be permanently implanted into human tissues and safely deliver high energy (greater than 100 KeV average gamma energy) tumor irradiation at an average dose rate less than 1.50 Gy/hour (Gray/hour-one Gray is equal to 100 rad) in less than 15 to 20 days.

It is a still further object of the invention to provide a novel technique for making an improved radioactive seed, seed ribbon, or radioactive wire which may be temporarily implanted into human tissues by after-loading tubes or by implanting interstial needles.

It is a still further object of the invention to produce a novel multilayered radioactive microsphere, ribbon microsphere, or multilayered radioactive wire, which emits electrons or beta particles and have casings which are substantially transparent to electrons.

It is a still further object of the invention to produce a more miniaturized intracavitary source that may be placed into the uterus without endocervical dilation or into the bladder with minimal trauma to the urethra and is available in a wide range of energies and isotopes.

A still further object of the invention is to produce a radioactive seed which has the clinical result of reducing the complication rate of treatment while increasing the local cure rate by allowing safe delivery of very high radiation doses to solid human tumors.

It is a still further object of the invention to provide novel method for production of radioactive microspheres, ribbon microspheres or wires in which the radioactive component is incorporated into the microsphere by the reaction of an excited radionuclide gas with a target material produced by reactive coating techniques.

It is a still further object of the invention to provide a novel method for production of radioactive microspheres, ribbon microspheres, or wires in which the radioactive component is incorporated into the microsphere by sputtering, laser ablation, cathodic arc plasma deposition or curvilinear cathodic arc plasma deposition from a target material consisting of a radioactive dielectric compound material or a radioactive metal.

It is a still further object of the invention to provide a radioactive seed that can be raised to a selected temperature by remotely radiated energy for hyperthermia.

It is a still further object of the invention to provide a radioactive seed that can be moved by remotely originated radiant energy.

It is a still further object of the invention to provide a radioactive, heatable seed that can be moved by remotely originated radiant energy.

It is a still further object of the invention to provide a novel therapy for necrosis of tumors.

It is a still further object of the invention to provide a novel therapy which combines low dose continuous radiation with higher dosage radiation for the destruction of tumors.

It is a still further object of the invention to provide a novel therapy for the incorporation of low energy implants into a tumor with externally applied high energy treatment to destroy a tumor.

It is a still further object of the invention to provide a novel therapy in which cancer cells are biased toward a sensitive state and then irradiated for a short period of time while in the sensitive state.

It is a still further object of the invention to produce a radioactive seed which has the clinical result of serving as a radiation sensitizer when implanted prior to administration of conventional external-beam radiation therapy and which delivers continuous low dose rate radiation to block tumor cells in the most radiation sensitive portions of their cell cycle.

According to the above and further objects of the invention, a one-piece solid spherical seamless multilayered radioactive seed, herein sometimes referred to as a multilayered radioactive microsphere includes a spherical radioactive thin layer with a therapeutic amount of activity. The spherical seed has several desirable characteristics such as for example: (1) its contents may provide up to 1000 millicuries of activity and a completely spherical photon fluence without significant anisotropy; and (2) there is no free space between the radioactive component and the casing.

In a preferred embodiment it includes a microspherical central marker, a spherical radioactive thin coat containing a therapeutic amount of activity, a spherical diffusion barrier coat, an optional special purpose spherical coating designed to enhance diagnositc imaging, a thick spherical (up to 0.10 mm) protective coating containing the inner coats, and an optional thin outermost special-purpose coat in the order listed. The multilayered radioactive microsphere contains: (1) no free spaces or cavities; and (2) no endwelds. The central marker or special coat for imaging may be selected for X-ray, PET, SPECT or MR or any other type of imaging.

The multilayer radioactive micropsphere radionuclide is selected for the desired purpose. For example, for a first group of purposes, the radionuclide has a weighted average gamma energy of less than 100 KeV, with a half-life of less than 130 days. This multilayer radioactive micropsphere is referred to as a low energy permanent multilayered radioactive microsphere for permanent interstitial implantation into human tumor tissues. The corresponding multilayer radioactive microsphere with a gamma energy greater than 100 KeV is referred to as a high energy permanent multilayered radioactive microsphere for permanent interstitial implantation into human tumor tissues. Preferably, its half life is less than 15 to 20 days.

For a second group of purposes, the radionuclide has a weighted average gamma energy greater than or equal to 100 KeV, with a half-life of greater than 15 to 20 days, or an average energy less than 100 KeV and a half-life of greater than 130 days. This multilayered radioactive microsphere is referred to as a temporary removable multilayered radioactive microsphere for temporary removable interstitial implantation into human tumor tissues.

For a third group of purposes, the radionuclide emits a high energy electron particle without significant high-energy gamma-ray component. This multilayer radioactive microsphere is referred to as an electron-producing or beta multilayered radioactive microsphere for permanent or temporary removable interstitial implantation into human tumor tissues.

The shape size and packaging of the multilayered radioactive seeds are appropriate for their purposes, such as being a microsphere having a diameter of 0.40 millimeters or less for use in injection equipment or in the case of wire or ribbon, having a similar diameter to permit interstitial tissue implanation through a regular 21 gauge needle or through a thin-walled 22 gauge needle.

The radioactive coat of the multilayered radioactive microsphere comprises one or more of: (1) a metal such as palladium-103, gold-198, thulium-170, or chromium-56, a mixture of metals, a mixture of compounds including radioactive metals or radionuclides, or a radionuclide bound to a metal; or (2) a dielectric radioactive element such as arsenic-73, yttrium-90, or iodine-125 or compound dielectric materials containing one non-radioactive and one radioactive component such as zirconium iodide Zr(I-125)4, hafnium iodide Hf(I-125)4, titanium iodide Ti (I-125)2, silver iodide-125, thulium bromide-170, magnesium arsenide-73, potassium iodide-125, rubidium silver iodine-125, or copper iodide-125; or (3) any combination of radioactive dielectric compounds; or (4) two or more radioactive components, such as for example arsenic-73 and di-iodide-125, arsenic-73, selenide-75, or palladium-103 and iodide-125.

The radioactive coat may also be formed in different configurations such as by being laminated together with a nonradioactive high boiling point or hard metal by sputtering, laser ablation ion plating, ion beam sputtering, or cathodic arc deposition; (2) by being uniformly covered by a spherical diffusion barrier that may consist of a coat of single metals such as gold, tantalum, palladium, and titanium or several layers of metals or compounds such as titanium-palladium-gold, gold-titanium, titanium nitride (TIN) zirconium nitride (ZrN) titanium carbide (TIC) titanium (T) tungsten/titanium (W/T), tungsten carbide (WC), tungsten nitride (WN), tungsten/titanium nitride (WTN), hafnium nitride (HfN), Hafnium carbide (HfC), zirconium carbide (ZRC), Vanadium carbide (VC), boron carbide (BC), tungsten boride (WB) or diamond. The diffusion barrier may be covered by a uniform spherical thick (up to 0.10 millimeter) protective coat.

Either inside the radioactive layer or over the diffusion barrier inside the protective coat, there may be an inner spherical uniform special purpose coat. This special purpose coat may be used to enhance imaging of the multilayer radioactive microsphere by means of conventional radiographs or MR, CT, SPEC or PET imaging. For example, the special spherical inner coat may consist of gadolinium for magnetic resonance imaging of the multilayer radioactive microsphere.

The spherical thick outside protective coat may be composed of: (1) a resistant human tissue-compatible metal which also has low atomic weight to minimize X-ray shielding such as titanium or other corrosion-resistant metal alloy such as stainless steel; or (2) a resistant human tissue-compatible metal compound (using reactive nitrogen, oxygen, methane, or carbon monoxide gases during coating to form carbides, nitrides, or carbonitrides of transition metals or other metals) such as titanium carbide, titanium nitride, titanium carbonitride, titanium aluminum nitride, zirconium nitride and hafnium nitride; or (3) a resistant human tissue-compatible metal coating less than 0.1 millimeters thick which has a high atomic weight such as tantalum, platinum or gold or the corresponding compounds of tungsten carbide, tantalum carbide, or platinum oxide; or (4) a human tissue-incompatible metal coating which is covered by a tissue-compatible thin coating.

If a tissue-compatible outermost thin coat is included it may be sputtered diamond, tantalum, tungsten or titanium and should overlay the thick protective metal casing. In this case, the more toxic but low atomic weight metals such as beryllium, vanadium, nickel and boron nitride may be used as the thick protective casing. The thin outer coats may consist of a special-purpose coats designed to enhance physical properties of the seed such as diamond or diamond-like carbon, platinum, or tantalum. These coats individually enhance the multilayer radioactive microsphere by adding hardness, and corrosion resistance.

The outermost thin coat may also be used to produce different seed identification colors. For example, the outermost thin coat may consist of titanium nitride (TIN) to produce a golden color, titanium carbonitride (TiCN) to produce a brown color, titanium aluminum nitride (TiAlN) to produce a black color, titanium carbide (TIC) to produce a gray color, zirconium nitride (ZrN) to produce a silver-yellow color, and hafnium nitride (HfN) to produce a yellow-green color.

The central sphere or other coats may be formed of a material that is heatable by remotely radiated energy for hyperthermia and/or a material that enables force to be applied to the seed to move it around using externally radiated energy to avoid damage to tissue. For example, ferrogmagnetic materials may be used that heat by induced radio frequency energy to the Curie temperature and have a Curie temperature appropriate for hyperthermia, such as for example, 50 degrees Centigrade. Moreover, a ferromagnetic material may cause movement of the seed by externally applied magnetic fields.

In one form of therapy using the multilayer radioactive microsphere, multiple low activity multilayer radioactive microsphere's (between 30 and 300) are permanently implanted into a human tumor at approximately 1 cm (centimeter) intervals throughout the volume, thus producing continuous low-dose-rate low energy irradiation at less than 1.0 Gy/hour and preferably less than 0.20 Gy/hour and delivering minimum doses of 80 to 400 Gy to the tumor volume over the average lifetime of the multilayer radioactive microsphere.

In another form of therapy using the multilayer radioactive microsphere (MRM) several (1 to 10) high activity multilayer radioactive microsphere's are permanently implanted into a human tumor producing continuous low-dose-rate low energy irradiation at less than 1.0 Gy/hour and preferably less than 0.20 Gy/hour and delivering minimum doses of 80 to 400 Gy to the tumor volume over the average lifetime of the multilayer radioactive microsphere.

In still another form of therapy, a long term low energy radiation is applied to a tumor followed by a short term high energy radiation. In one embodiment, the low energy radiation serves as a radioactive sensitizer which blocks tumor cells in the most radioactive sensitive portions of their cell cycles and the high energy beam is applied when the tumor cells are sensitive.

In one embodiment, a low intensity radioactive seed is implanted to provide the long term low intensity radioactivity and external radiation beam is used for the high intensity. In this embodiment, the relatively low radiation dose of between 40 to 80 Gray is delivered substantially continuously at a low dose rate over a time period of 30 to 200 days and preferably approximately 30 days. Either temporary or permanent implantation of one or several seeds may be used to accomplish this purpose. This low dose-rate radiation blocks the tumor cells in their most radioactive sensitive parts of their cell cycles. These are optimally killed at the time of delivery of a conventional daily fractionated radiation given over two minutes each 24-hour period for five days a week.

To make multilayer coatings of a microsphere for mass-production of the multilayer radioactive microsphere, a microspherical substrate is coated with multiple uniformly-spherical coats which consist of a radioactive coat, a thick protective coat (up to 0.1 millimeter) and in some embodiments, a diffusion barrier coat, an optional special-purpose imaging-enhancement coat and an optional special purpose outer thin coat.

The microsphere is adapted to be made in a manufacturing process that eliminates the need for assembly of separate seed parts and welding of titanium tubing containing the radioactive material because the multilayer radioactive microsphere is constructed by electronic means. In the processes used: (1) one-hundred to one-thousand multilayer radioactive microsphere's can be produced in a single batch or run of the coating equipment; and (2) the design of the multilayer radioactive microsphere can be easily modified or its components or type of radionuclide easily changed by changing either the target materials, coating atmosphere or operational parameters of the coating process.

In manufacturing the coats, existing coating techniques are used. In one embodiment, one or more radioactive dielectric or metal materials are used as a target in a sputter-deposition, laser ablation, or cathodic arc plasma-deposition system to produce a stable radioactive radionuclide-metal coat upon microspherical substrates, ribbon-mircospheres, or wire substrates. Moreover, combinations of radioactive and nonradioactive materials may be used.

The deposition of the radionuclide coat or laminate of a radionuclide and high-boiling point metal must be uniform. The peak-to-valley height variation in this coating should not exceed plus or minus 400 Angstroms. It should have high quality in terms of uniformity, spherosity and not have macroparticles, holes or other defects.

Other thin layers should be uniform but are not as sensitive to the lack of uniformity. Those layers are the diffusion barrier coat and in some embodiments, imaging coats. A relatively thick protective coat such as one of 0.05 millimeters is less critical as to uniformity.

All of these substrates are applied by processes which bond so there are substantially no voids in the member. Generally, sputtering is preferred with the thicker layers utilizing higher power and larger targets and the thinner layers smaller targets and lower power so that the same apparatus may be used for the different coats and all be applied with reasonable speed in spite of the difference of thicknesses by energizing different targets at different times. Thicker coats might also be applied by cathodic arc plasma-deposition techniques although these techniques do not usually apply with the same uniformity. In a few embodiments, electrolysis is suitable although electrolysis in most applications does not provide as uniform a surface area as sputtering and in the case of microspheres, it is difficult to obtain uniformity on all sides.

Generally, fabrics, wires and ribbons may be plated while they are suspended in a vacuum but the microspheres require a levitating device such as a vibrator that bounces them so that they will be coated on all sides. The most uniform coats are applied by vacuum methods but there are other methods which can create the uniformity and intimate contact of the coats desired in these products. Because some of the radionuclide coats are soft, low boiling point metals, special precautions can be taken to prevent the microspheres from being welded together. One such precaution is to combine the low boiling point radionuclide with a higher boiling point metal in interleaved areas or concomitantly. Injection of 1% to 5% of an electronegative gas such as oxygen gas will present microsphere vacuum welding. In another embodiment, gaseous radionuclides are bound by combining them with a metal during the coating process such as by sputtering the radioactive nuclide gas together with a metal in an argon atmosphere to form a coat of a compound combining the radionuclide and the metal.

The multilayer radioactive microsphere radioactive microspherical substrate coat may be produced by one of several processes, such as: (1) from a radioactive metal target by dc sputtering; or (2) by radio frequency or magnetron sputtering using a radioactive dielectric target; or (3) by reactive sputter-deposition in an excited radioactive gas producing a coat which is a radioactive compound of the radioactive gas and the sputtered target material; or (4) by reactive cathodic arc plasma deposition in an excited radioactive gas producing a coat which is a radioactive compound of the radioactive gas and the sputtered target material; or (5) by reactive ion beam sputtering using a cathodic arc ion source in an excited radioactive gas producing a coat which is a radioactive compound of the radioactive gas and the sputtered target material; or (6) by reactive ion-plating using an electron-beam source in an excited radioactive gas producing a coat which is a radioactive compound of the radioactive gas and the sputtered target material; or (7) by cathodic arc plasma deposition using a radioactive dielectric target; or by (8) laser ablation of the target metal in the presence of a radioactive gas forming a radioactive metal compound on the substrate.

A radioactive dielectric coated planar metal target for use in cathodic arc plasma deposition or for use in rf or magnetron sputtering may be made by coating a metal planar substrate with a radio-active dielectric compound using reactive dc, rf, or magnetron sputtering, reactive cathodic arc plasma deposition, reactive ion-beam sputtering, or reactive ion plating wherein the radioactive compound coat is produced from an excited radionuclide gas and a non-radioactive metal target.

To optimize mass-production manufacture of the multilayer radioactive microsphere a two step process is used employing sputter deposition with a radioactive dielectric or metal target, or reactive sputter deposition in a radionuclide gas to produce a uniform radioactive coat over a microspherical substrate followed by ion-plating, or ion-beam self-sputtering using a cathodic arc ion source, or cathodic arc plasma deposition or high-energy high deposition rate sputtering using a large sputter gun, to produce the remaining coatings and spherical thick protective metal coatings over the radioactive microspheres.

In another method for mass-production manufacture of the multilayer radioactive microsphere consisting of a one-step process employing reactive cathodic arc plasma deposition, reactive laser ablation deposition, or reactive ion beam sputtering using a cathodic arc ion source, or reactive ion plating all carried out in an excited radionuclide reactive gas/inert gas mixture to form a smooth spherical stable compound radioactive coating over a microspherical substrate, followed by use of either ion plating, ion beam sputtering, cathodic arc deposition or laser ablation to produce the remaining coatings and spherical thick protective metal coatings over the radioactive microspheres.

In still another optimized method for mass-production manufacture of the multilayer radioactive microsphere consisting of a one-step process employing cathodic arc plasma deposition using a radioactive dielectric or metal target to produce a radioactive coat over a microspherical substrate, followed by use of cathodic arc plasma deposition to produce the remaining coats and spherical thick protective metal coats over the radioactive microspheres.

To eliminate vacuum welding between levitated microspheres, soft low boiling point elements (that are likely to vacuum weld) are laminated with hard, high boiling point elements (that are unlikely to vacuum weld). The microspherical substrates may be biased to improve reactive deposition efficiency using a reactive gas in a sputtering, ion plating, ion beam sputtering, or cathodic arc deposition.

Several embodiments of therapeutic devices can be formed. In one embodiment a ribbon-multilayer radioactive microsphere substrate has microspheres attached to the ribbon prior to coating. Coats are then applied to form a ribbon surface for rapid implanting of seeds. The coats may vary at different locations to enable in some embodiments, a contoured radiation pattern. In another embodiment, a multilayered radioactive wire design has a coat applied to a wire substrate by means of sputtering, laser ablation ion plating, ion beam sputtering, or cathodic arc deposition. The radioactive material is differentially deposited onto a substrate wire in such a manner that variable activities are deposited per unit length in a controlled fashion to match a computerized treatment plan.

In other embodiments absorbable or non-absorbable surgical fabrics containing multiple multilayer radioactive microspheres spaced apart on the fabric or minituriazed intracavitary sources of radioactivity composed of multiple multilayer radioactive microsphere's are fabricated. Coats are applied in successive layers on the fabric and microsphere substrate or only on the microsphere substrate using masking in forming a fabric. Also, finished microspheres can be embedded during manufacture of a cellulose fabric. To form small intracavity sources, microspheres are first formed by sputtering or other such manufacturing technique and then afterloaded into containers that are welded shut. In still another embodiment, an ocular applicator is constructed in which radioactive multilayers are deposited on the active surface by means of sputtering, ion plating, ion beam sputtering, cathodic arc deposition, or laser ablation.

Some of the embodiments that are fabricated enable improvement in other known techniques. For example, a modified multilayer radioactive microsphere that contains a ferromagnetic alloy that may be inductively heated in situ by applied radio frequency radiation may be formed. The coat passes through a Curie transition at temperatures useful for clinical hyperthermia and stops receiving inductive heating, thus maintiaining the proper temperature. Also, a solid multilayered radioactive needle for temporary removable implants incorporates a wide variety of radionuclides and is thinner than a conventional radium-containing needle, thus enabling its use without major tissue trauma and improving the implant geometry.

The radioactive single seed design of this invention has several advantages such as: (1) it is smaller than prior art radioactive seeds and is spherical thus permitting a wider range of uses and easier use with less traumatic insertion into human tissues; (2) it is stronger and has high structural integrity and is thus safer; (3) it is symmetrical and uniform and thus produces a symmetrical radiation field as shown by symmetrical dosimetry; (4) it may be constructed using a wide variety of isotopes of differing energies and half-lives selected for specific applications, thus permitting optimization of the radiobiology of the type of cancer being treated; (5) it is inexpensive; and (6) in clinical practice, it permits safe delivery of radiation tumor doses that are two to five times higher than that achieved with external beam irradiation; and (7) the different multilayered radioactive microspheres can be identified by their different imaging contrast agent coats or center substrate.

In use, the microspheres have several advantages such as: (1) an effective modality for treatment is provided by combining a relatively low continuous dose of radiation by multilayer radioactive microspheres implanted in a tumor at any anatomic location and which serve as radiosensitizers so that a short conventional course of external-beam radiation therapy is much more effective; (2) radiation dose localization is improved beyond that achievable with the low energy permanent gamma-ray seeds by use of an electron-producing seed because electron dosimetry is more localized than X-ray dosimetry; (3) different types of multilayered radioactive microspheres with different half-lives and photon or electron energies can be implanted into a tumor in the same operation to optimize tumor therapy; and (4) the use of permanent implantation of short-lived seeds rather than temporary-removable implants eliminate exposed tubes which penetrate the skin surface and serve as a route for infection over many days.

There are also advantages from the composite designs that can be produced using the spheres, such as for example: (1) ribbons and a tissue-compatible fabric containing seeds useful for rapid surgical implantation may be produced; (2) the thin ribbon design containing multiple seeds allows rapid implantation of multiple seeds using a hollow interstitial needle; (3) a tissue-compatible surgical fabric containing multiple radioactive seeds allows rapid intraoperative implantation of a sheet of evenly spaced radioactive seeds; and (4) the various surgical procedures and devices used for implantation of radioactive seeds provide better adaptability to a patient's needs.

There are also advantages from a wire multilayered radioactive design such as: (1) it may be cut up into pieces and placed into afterloading catheters or into nylon or polyethylene ribbons for temporary removable implants or placed inside appropriate containers to construct various intracavitary sources; (2) it has the advantages of being flexible or remain as a long needle, with or without an added sleeve for temporary implanting.

When encapsulated: (1) the multilayered radioactive microspheres simplify intracavitary therapy because smaller intracavitary capsules can be construed using multiple small-diameter seeds of the present invention; (2) a wide variety of radionuclides with energies varying from very low to very high can be incorporated into composite intracivitary sources by sealing multiple multilayered radioactive microspheres of one or several types into an appropriate container; (3) use of low energy intracavitary sources composed of low energy multilayered radioactive microspheres allow selective shielding of adjacent vital structures such as rectum and bladder using relatively thin high atomic weight foils placed over the intracavitary sources or source holders.

There are also several advantages related to manufacturing the radioactive implants such as: (1) it permits mass production of a variety of designs without need of assembly of separate (radioactive) parts; (2) changes in seed composition may be made easily; (3) it permits customized manufacture of multilayered radioactive microspheres, multilayered radioactive wires, ribbon-multilayered radioactive microspheres or optical plaques optimized for individual tumor types; (4) manufacture of new models of multilayered radioactive microspheres, multilayered radioactive wires and ribbon-multilayered radioactive microspheres can be accomplished as needed by simply changing deposition parameters, or by changing the type, thickness, and layering of deposited elements using the same deposition equipment; (5) it permits construction of seeds containing many optional different types of laminated materials such as imaging contrast agents, colored seed identification markers, or supplemental protective outer layers; (6) use of the high energy processes of sputtering, laser ablation ion-beam sputtering, cathodic arc or curvilinear cathodic arc plasma deposition, reactive deposition, and ion plating increase the hardness of metals coated in this manner compared to the bulk materials; and (7) the controlled variable deposition of radioactive material per unit length or per unit surface area permits customized manufacture of brachytherapy sources to exactly match the requirements of 3-dimensional computerized brachytherapy treatment plan.

The ability to provide a variety of half-lives and intensities of implants has several advantages, such as for example: (1) the smaller permanent seeds permit implantation of a greater number of seeds in more body sites using thinner needles with less risk of complication; (2) a combination of short-acting high-energy and long-acting low energy seeds can be implanted in the same procedure; (3) under some circumstances repeated implantation of seeds with short half-lives may be used instead of repeated temporary removable implant procedures thus reducing the risk of infection associated with temporary removable implants; (4) high energy short-lived seeds provide results equivalent to a temporary removable implant, but they may be applied to sites not accessible to temporary removable implantation; (5) short-lived seeds may be implanted as a "tumor-boost", replacing and improving upon a "tumor-boost" delivered by means of external-beam radiation therapy; (6) with a wide variety of seeds available, many cancers can be more effectivley managed by brachytherapy alone; (7) a wide variety of radionuclides with energies varying from very low to very high can be incorporated into composite intracavitary sources by sealing multiple multilayered radioactive microspheres of one or several types into an appropriate container; (8) use of low energy intracavitary sources composed of low energy multilayered radioactive microspheres al low selective shielding of adjacent vital structures such as rectum and bladder using relatively thin high atomic weight foils placed over the intracavitary sources or source holders.

The ribbons, wire, plaques and fabric of this invention have the advantages of: (1) multiple multilayered radioactive microspheres provided on a single ribbon allow multiple multilayered radioactive microspheres to be implanted at once by a thin gauge hollow needle by pushing the multilayer radioactive microsphere ribbon out of the tissue-embedded needle with a stylet while withdrawing the needle; (2) the ribbon-multilayered radioactive microspheres of the present invention may be implanted by a very thin 21 or 22-gauge needle; (3) the fabric of this invention self-adheres to the tissues over which it is placed and may be either tissue-absorbable or non-tissue absorbable; (4) the use of a fabric containing multiple multilayered radioactive microspheres allows rapid surgical implantation of multiple seeds without need of interstitial needles or a seed gun; and (5) very thin plaques such as optical plaques can be contoured have the appropriate strength and appropriate intensity for effective treatment.

SUMMARY OF THE DRAWINGS

The above noted and other features of the invention will be better understood from the following detailed description when considered with reference to the accompanying drawings in which:

FIG. 5 is a sectional view of still another embodiment of multilayer radioactive microsphere;

FIG. 6 is a longitudinal sectional view of an embodiment of intracavitary radiation-emitting implant;

FIG. 7 is a perspective view of another embodiment of the invention formed as a wire or rod-like member;

FIG. 8 is a sectional elevational view of a ribbon-like embodiment;

FIG. 9 is a top sectional view of the embodiment of FIG. 8;

FIG. 10 is a plan view of an optical plaque in accordance with an embodiment of the invention;

FIG. 11 is a sectional view of the embodiment of FIG. 10 taken through lines 11—11;

FIG. 12 is a plan view of another embodiment of optical plaque in accordance with the invention;

FIG. 13 is a plan view of still another embodiment of optical plaque;

FIG. 14 is a plan view of still another embodiment of optical plaque;

FIG. 15 is a plan view of still another embodiment of optical plaque;

FIG. 16 is a plan view of still another embodiment of optical plaque;

FIG. 17 is a plan view of still another embodiment of optical plaque;

FIG. 27 is still another embodiment of apparatus for making microspheres;

FIG. 28 is still another embodiment of apparatus for making microspheres;

DETAILED DESCRIPTION

Figure 1:
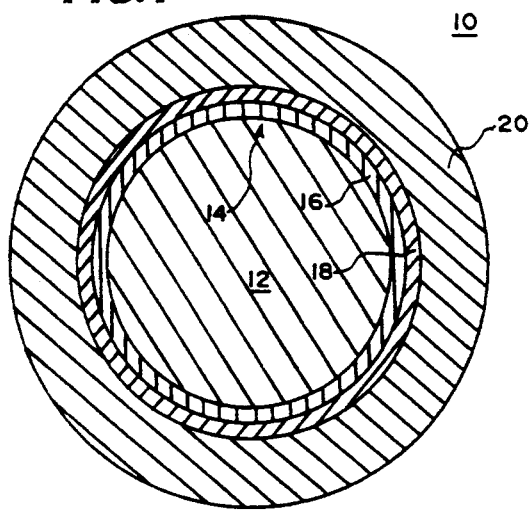
FIG. 1 is a hemispherical sectional view of a multilayer radioactive microsphere in accordance with an embodiment of the invention.
Figure 2:
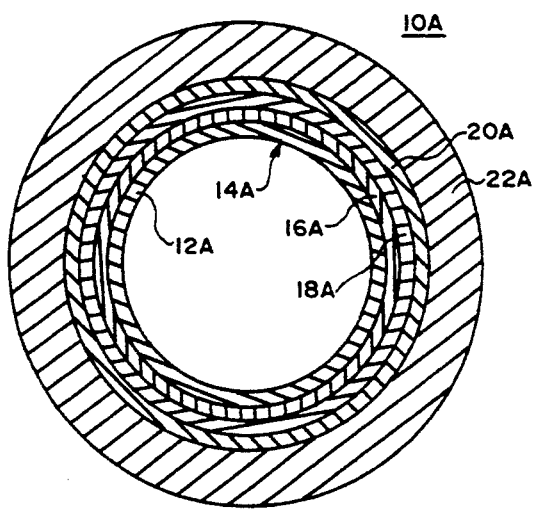
FIG. 2 is a sectional view of another embodiment of a multilayer radioactive microsphere.
Figure 3:
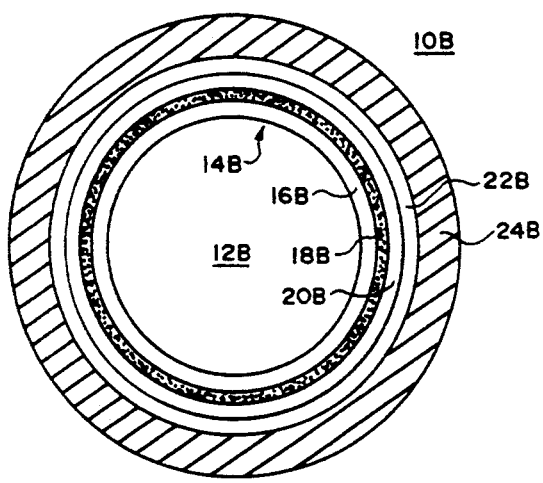
FIG. 3 is a sectional view of still another embodiment of multilayer radioactive microsphere.

In FIG. 1, there is shown a sectional view of a radiation-emitting or radioactive microsphere 10 having a central sphere 12, and a layered section 14, with no space or voids between layers or between the central sphere 12 and the layered section 14 and no end-welds. It has an outside diameter less than 1 millimeter and provides a therapeutic amount of radiation selected in accordance with the desired treatment.

The central section is a microsphere and is normally solid but may be hollow. In the preferred embodiment, the material of which the central section is made is selected to serve as a substrate for other usefull coats applied over it, and under some circumstances, to serve other functions such as to identify or locate the implant. For this latter purpose, it may be selected to be opaque to radiation such as X-rays or easily detectable by other devices. If the central section 12 is itself the source of the therapeutic radiation, there may be a reduced number of layers in the layered section 14.

The center section or core 12 is less than 1 millimeter in diameter and in the preferred embodiment is generally 0.2 millimeters. However its size may be varied to accommodate different coating processes or to distinguish one radiation-emitting sphere from another by sensing the center section or the like. In the preferred embodiment the material is selected for its function.

This substrate center or core 12 may be made of a high atomic number metal or alloy such as iridium, platinum, gold, tantalum, tungsten or lead. Additionally, any lower atomic weight metal or alloy which is satisfactorily visualized on radiographs may be used including molybdenum, indium, lithium, silver, copper, and steel. Platinum, tantalum, gold, and silver are the preferred X-ray marker multilayer radiation-emitting microsphere core substrate materials in the present invention because of their high visibility on conventional radiographs.

In another seed design disclosed wherein only magnetic resonance imaging of the seed is clinically desirable and X-ray imaging is not necessary, the seed core 12 is composed of a non-metal such as carbon or diamond and an outer seed coat producing a magnetic resonance imaging signal (gadolinium) described below produces the seed image.

A multilayer radiation-emitting microsphere without a ferromagnetic core is essentially non-magnetic. This absence of ferromagnetic metal is advantageous for clinical situations where the implanted seed is implanted in close proximity to critical structures, such as near arterio-venous realformations in the brain. Here a strong magnetic field produced by magnetic resonance imaging equipment may exert enough force to dislodge or move a ferromagnetic metal-containing seed. A magnetically dislodged seed in the brain could cause immediate neurologic damage, stroke, or death of the patient. It could also be lost into the cerebrospinal fluid.

In the embodiment 10 of radiation-emitting microsphere of FIG. 1, the layered section 14 includes three layers 16, 18, and 20, in the order named, from the center section 12 outwardly. Each layer is concentric and they are selected in accordance with any of several therapeutic techniques. Other embodiments to be described hereinafter have still further coats and some embodiments may require primer coats to improve the ability to apply the layers to the central section or to each other or may require careful selection of techniques such as using mixtures of the material of the two coats at the interface between them.

Preferred primer metals include titanium, aluminum, tin, tantalum, vanadium, titanium nitride, titanium iodide, titanium oxide, titanium carbide, or metal alloys such as stainless steels or nickel alloys. If the coated material of one coat or the central section does not have good surface compatability with any primer metal, then a graded interface can be created composed of the materials of both coats or the central microsphere and its first coat as described below for a central substrate and a first coat that is a radioactive material.

The layer 16 may be an evenly distributed, highly-controlled, uniform, smooth, thin (less than 0.01 mm to 0.045 mm) spherical radiation-emitting coat that is produced by any method that results in a layer in intimate contact without void spaces. The material of the coat 16 may be any radiation-emitting material including: (1) a radionuclide with a weighted average gamma energy of less than 100 KeV, and with a half-life of less than 130 days for low energy permanent interstitial implantation; or (2) a radionuclide with a weighted average gamma energy greater than or equal to 100 KeV and with a half-life of less than 15 to 20 days for high-energy permanent interstitial implantation; or (3) a radionuclide that has a weighted average gamma energy greater than or equal to 100 KeV, with a half-life of greater than 15 to 20 days or an average energy less than 100 KeV and a half-life of greater than 130 days for temporary removable interstitial implantation; or (4) a radionuclide that emits a high energy electron particle without significant high-energy gamma-ray component for permanent or temporary removable interstitial implantation. It may be one metal, a mixture of metals, a dielectric compound, a mixture of dielectric compounds, a radionuclide that is normally a gas but is bound to a metal or other material in the radiation-emitting layer 16 or a plurality of layers of materials.

To provide the desired characteristics, the material of the layer 16 may be a metal selected from the group comprising palladium-103, gold-198, thulium-170, or chromium-56 or a combination of these or a dielectric radiation-emitting element such as arsenic-73, yttrium-90, or iodine-125 or a combination of these or a compound dielectric material containing one non-radiation-emitting and one radiation-emitting component with the radiation-emitting component such as zirconium iodide Zr (I-125)$_4$, hafnium iodide Hf (I-125)$_4$ titanium iodide Ti (I-125)$_2$, silver $^{125}$iodide, thulium bromide-170, magnesium $^{73}$arsenide, potassium $^{125}$iodide, rubidium silver $^{125}$iodine, or copper $^{125}$iodide. It may include a radiation-emitting dielectric compound coat having two or more radiation-emitting components including any of arsenic-73 and diiodide-125, arsenic-73, selenide-75, and palladium-103 iodide-125 or it may be laminated with a non-radiation-emitting and radiation-emitting materials.

A list of such materials is provided in tables 1–19 of appropriate target materials and gases is provided in tables 20–58.

Moreover, instead of being a radiation-emitting microsphere from the start, the layer 16 may be formed of a material not in final form and altered by imparting radiation such as by nuclear or neutron bombardment or by combination with other layers of material under energy sources such as heat. For example, the microsphere in one stage of development may include a coat that is a non-radiation-emitting isotope precursor of the desired radiation-emitting isotope (such as those elements labelled with a * in tables 1–15). One such multilayer radiation-emitting microsphere may first contain a primary coat of non-radiation-emitting palladium-102 or samarium-144 but may be later irradiated with neutrons in a nuclear reactor or in a "neutron oven" to produce a finished multilayer radiation-emitting microsphere containing radiation-emitting palladium-103 or radiation-emitting samarium-145, respectively.

TABLE 1

RADIONUCLIDES FOR LOW ENERGY PERMANENT MULTILAYERED RADIOACTIVE MICROSPHERES
(Main Gamma Energies less than 100 KeV,
Half-Life less than 130 days)

| RADIONUCLIDE | HALF-LIFE | MAIN GAMMA ENERGIES |
|---|---|---|
| As-73 | 80.3 days | 53.4 KeV |
| Se-72 | 8.4 days | 46.0 KeV |
| Pd-100 | 3.6 days | 75–84 KeV |
| *Pd-103 | 17.0 days | 39.7 (0.02% 357 KeV) |
| Pd-112 | 21.0 hours | 18.5 KeV |
| *Te-123m | 117.0 days | 88–159 KeV |
| Te-127m | 109.0 days | 88.3 KeV |
| Te-125m | 58.0 days | 35.5 KeV |
| I-125 | 59.9 days | 35.5 KeV |
| *Ce-141 | 33.0 days | 145 KeV |
| *Nd-147 | 10.9 days | 91.1 KeV (13% 531 KeV) |
| Tb-151 | 17.6 hours | 108–731 KeV |
| Tb-155 | 5.3 days | 86.5–105.3 KeV |

*radioisotope can be created by neutron irradiation of corresponding (naturally) occurring isotope, thus allowing manufacture of non-radioactive microsphere with subsequent activation of placing finished product in a "neutron oven".

TABLE 2

RADIONUCLIDES FOR LOW ENERGY PERMANENT MULTILAYERED RADIOACTIVE MICROSPHERES
(Main Gamma Energies less than 100 KeV,
Half-Life less than 130 days)

| RADIONUCLIDE | HALF-LIFE | MAIN GAMMA ENERGIES |
|---|---|---|
| Tb-161 | 6.9 days | 25.6–74.6 KeV |
| Dy-166 | 81.6 hours | 82.5 KeV (0.5% 426 KeV) |
| Ho-166 | 1.1 days | 80.6 KeV (0.6% 1.4 MeV) |
| *Er-168 | 9.4 days | 8.42 KeV |
| *Tm-170 | 128.6 days | 84.3 KeV |
| Sb-119 | 36.1 hours | 23.9 KeV |
| Lu-176m | 3.6 hours | 88.3 KeV |
| *Os-191 | 15.0 days | 49–186 KeV |
| Hg-197 | 64.1 hours | 77.4 KeV |
| *Pt-195m | 4.0 days | 31–130 KeV |
| Th-231 | 25.2 hours | 25.6–84.2 KeV (0.2% 108 KeV) |
| Th-234 | 24.1 days | 63.3–92.7 KeV (0.3% 113 KeV) |

*radioisotope can be created by neutron irradiation of corresponding naturally occurring isotope, thus allowing manufacture of the non-radioactive microsphere with later conversion to the radioactive product by activating the seeds in a "neutron oven".

TABLE 3

RADIONUCLIDES FOR LOW ENERGY PERMANENT MULTILAYERED RADIOACTIVE MICROSPHERES
(Main Gamma Energies less than 100 KeV,
Half-Life less than 130 days)

| RADIONUCLIDE | HALF-LIFE | MAIN GAMMA ENERGIES |
|---|---|---|
| Pu-237 | 45.1 days | 59.5 KeV |
| U-231 | 4.2 days | 25.6 KeV (13%) 84.2 KeV (6%) |
| Tl-201 | 3.05 days | Hg K-X-ray |

*radioisotope can be created by neutron irradiation of corresponding naturally occurring isotope, thus allowing manufacture of the non-radioactive microsphere with later conversion to the radioactive product by activating the seeds in a "neutron oven".

TABLE 4

RADIONUCLIDES FOR HIGH ENERGY PERMANENT MULTILAYERED RADIOACTIVE MICROSPHERES
(Main Gamma Energies greater than 100 KeV,
Half-Life Less than 130 days)

| RADIONUCLIDE | HALF-LIFE | MAIN GAMMA ENERGIES |
|---|---|---|
| K-43 | 22.3 hours | 373 KeV |
| As-74 | 17.8 days | 595 KeV |
| As-77 | 38.8 hours | 239 KeV |
| Sc-47 | 3.4 days | 159 KeV |
| Zr-86 | 16.5 hours | 243 KeV |
| In-111 | 2.8 days | 170–245 KeV |
| Sm-153 | 46.7 hours | 103 KeV |
| Sm-156 | 9.4 hours | 87–204 KeV |
| Eu-157 | 15.2 hours | 64–413 KeV |
| Gd-159 | 18.6 hours | 364 KeV |
| Pb-203 | 2.2 days | 279 KeV |
| V-48 | 15.9 days | 984 KeV |
| Cr-48 | 21.6 hours | 116–305 KeV |
| *Fe-52 | 8.2 hours | 168–377 KeV |

TABLE 5

RADIONUCLIDES FOR HIGH ENERGY PERMANENT MULTILAYERED RADIOACTIVE MICROSPHERES
(Main Gamma Energies greater than 100 KeV,
Half-Life Less than 15 to 20 days)

| RADIONUCLIDE | HALF-LIFE | MAIN GAMMA ENERGIES |
|---|---|---|
| Cu-67 | 61.9 hours | 91.2–184 KeV |
| Zn-62 | 9.3 hours | 41.0–596 KeV |
| Ga-67 | 78.3 hours | 93.0–394 KeV |
| Ga-73 | 4.9 hours | 297 KeV |
| Se-73 | 7.1 hours | 67.0–361 KeV |
| Br-77 | 57.0 hours | 87.0–818 KeV |
| *As-76 | 26.5 hours | 559- KeV |
| Kr-76 | 14.8 hours | 45.5–452 KeV |
| Rb-81 | 4.6 hours | 190–446 KeV |
| Sr-83 | 32.4 hours | 763 KeV |
| Y-87 | 80.3 hours | 388 KeV |
| Mo-99 | 65.9 hours | 144–739 KeV |
| Ru-97 | 2.9 days | 214–461 KeV |
| Rh-105 | 35.4 hours | 306–319 KeV |
| Cd-107 | 6.5 hours | 93–829 KeV |
| Cd-115 | 53.5 hours | 336–528 KeV |
| Sn-110 | 4.0 hours | 283 KeV |
| *Sn-117m | 14.0 days | 159 KeV |

TABLE 6

RADIONUCLIDES FOR HIGH ENERGY PERMANENT MULTILAYERED RADIOACTIVE MICROSPHERES
(Main Gamma Energies greater than 100 KeV,
Half-Life Less than 15 to 20 days)

| RADIONUCLIDE | HALF-LIFE | MAIN GAMMA ENERGIES |
|---|---|---|
| Te-119 | 16.0 hours | 644 KeV |
| Te-132 | 78.2 hours | 49.7–228 KeV |
| Cs-127 | 6.2 hours | 412 KeV |
| Cs-129 | 32.3 hours | 371–412 KeV |
| Ag-111 | 7.5 days | 250–340 KeV |
| Te-121 | 16.8 days | 573 KeV |
| I-131 | 8.0 days | 364 KeV |

TABLE 6-continued

RADIONUCLIDES FOR HIGH ENERGY PERMANENT MULTILAYERED RADIOACTIVE MICROSPHERES
(Main Gamma Energies greater than 100 KeV, Half-Life Less than 15 to 20 days)

| RADIONUCLIDE | HALF-LIFE | MAIN GAMMA ENERGIES |
|---|---|---|
| Ba-128 | 2.4 days | 273 KeV |
| Ba-131 | 11.8 days | 496 KeV |
| Ba-140 | 12.8 days | 162–537 KeV |
| *Ce-141 | 33.0 days | 145 KeV |
| Ce-134 | 76.0 hours | 605 KeV |
| Ce-137 | 9.0 hours | 447 KeV |
| Nd-138 | 5.1 hours | 199–326 KeV |
| Pm-151 | 28.4 hours | 340 KeV |
| Tb-155 | 5.3 days | 86.5–105.3 KeV |

TABLE 7

RADIONUCLIDES FOR HIGH ENERGY PERMANENT MULTILAYERED RADIOACTIVE MICROSPHERES
(Main Gamma Energies greater than 100 KeV, Half-Life Less than 15 to 20 days)

| RADIONUCLIDE | HALF-LIFE | MAIN GAMMA ENERGIES |
|---|---|---|
| Dy-157 | 8.1 hours | 182–326 KeV |
| Yb-175 | 4.19 days | 114–396 KeV |
| Os-182 | 21.5 hours | 131–510 KeV |
| Os-191 | 15.4 days | 129.4 KeV |
| Pt-184 | 10.2 days | 188–423 KeV |
| Pr-143 | 13.6 days | 742 KeV |
| Eu-157 | 15.2 hours | 413 KeV |
| Gd-149 | 9.3 days | 149–346 KeV |
| Er-169 | 9.4 days | 109–118 KeV |
| Tm-167 | 9.2 days | 208 KeV |
| Tm-173 | 8.2 hours | 398–461 KeV |
| Yb-175 | 4.2 days | 114–396 KeV |

TABLE 8

RADIONUCLIDES FOR HIGH ENERGY PERMANENT MULTILAYERED RADIOACTIVE MICROSPHERES
(Main Gamma Energies greater than 100 KeV, Half-Life Less than 15 to 20 days)

| RADIONUCLIDE | HALF-LIFE | MAIN GAMMA ENERGIES |
|---|---|---|
| Hf-170 | 16.0 hours | 593–621 KeV |
| Hf-171 | 12.1 hours | 122–1,071 KeV |
| Hf-173 | 23.6 hours | 123.6–311.2 KeV |
| Hf-184 | 4.1 hours | 139–345 KeV |
| Re-181 | 20.0 hours | 177–365 KeV |
| Re-188 | 16.9 hours | 155 KeV |
| Re-189 | 24.0 hours | 148–563 KeV |
| Lu-177 | 6.7 days | 113–332 KeV |
| Lu-179 | 4.6 hours | 214 KeV |
| Ta-177 | 2.4 days | 113 KeV |
| Ta-180m | 8.2 hours | 93.3–103 KeV |
| Ta-183 | 5.1 days | 246–354 KeV |
| W-187 | 23.9 hours | 479–685 KeV |
| Ir-189 | 13.2 days | 245 KeV |
| Pt-191 | 2.9 days | 82.4–539 KeV |
| Pt-197 | 18.3 hours | 191.4 KeV |
| Pt-200 | 12.5 hours | 135–330 KeV |

TABLE 9

RADIONUCLIDES FOR HIGH ENERGY PERMANENT MULTILAYERED RADIOACTIVE MICROSPHERES
(Main Gamma Energies greater than 100 KeV, Half-Life Less than 15 to 20 days)

| RADIONUCLIDE | HALF-LIFE | MAIN GAMMA ENERGIES |
|---|---|---|
| Au-193 | 17.6 hours | 112–439 KeV |
| *Au-198 | 2.7 days | 412 KeV |
| Au-199 | 3.1 days | 158–208 KeV |
| Hg-192 | 4.9 hours | 275 KeV |
| Hg-195m | 40.0 hours | 262 KeV |

TABLE 9-continued

RADIONUCLIDES FOR HIGH ENERGY PERMANENT MULTILAYERED RADIOACTIVE MICROSPHERES
(Main Gamma Energies greater than 100 KeV, Half-Life Less than 15 to 20 days)

| RADIONUCLIDE | HALF-LIFE | MAIN GAMMA ENERGIES |
|---|---|---|
| Hg-197m | 23.8 hours | 134 KeV |
| Tl-201 | 3.0 days | 135–165 KeV |
| Tl-202 | 12.2 days | 439 KeV |
| Pb-100 | 21.5 hours | 148 KeV |
| Nb-90 | 14.6 hours | 141–2,319 KeV |
| Nb-92m | 10.1 days | 934 KeV |
| Nb-96 | 23.4 hours | 460–1,202 KeV |
| Bk-245 | 4.9 days | 253 KeV |
| Bk-246 | 1.8 days | 799 KeV |
| Es-254m | 1.64 days | 648–693 KeV |
| U-237 | 6.75 days | 59.0 KeV (33%) |
|  |  | 208.0 KeV (22%) |

TABLE 10

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Be-7 | 53.3 days | 477 KeV |
| Sc-46 | 83.3 days | 159 KeV |
| As-74 | 17.8 days | 595 KeV |
| *Se-75 | 120.4 days | 135–264 KeV |
| Co-57 | 271.0 days | 122 KeV |
| Rb-83 | 86.2 days | 521–529 KeV |
| Sr-85 | 64.8 days | 514 KeV |
| Ti-44 | 47.0 days | 67.8–78.4 KeV |
| Se-75 | 118.5 days | 136–264 KeV |
| Zr-88 | 83.4 days | 393 KeV |
| Zr-93 | $1.5 \times 10^6$ years | 30.4 KeV |
| *Zr-95 | 64.0 days | 724–756 KeV |
| La-138 | $1.06 \times 10^{11}$ years | 788–1,436 KeV |
| Gd-146 | 48.3 days | 115–155 KeV |
| Nb-92 | $3 \times 10^7$ years | 61–935 KeV |
| Nb-93m | 13.6 years | 30.4 KeV |
| Nb-94 | $2.4 \times 10^4$ years | 703–871 KeV |
| Nb-95 | 34.9 days | 766 KeV |
| *Mo-93 | $3.5 \times 10^3$ years | 30.4 KeV |

TABLE 11

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Cr-51 | 27 days | 320 KeV |
| *Cd-109 | 450 days | 88 KeV |
| *Cd-115m | 43 days | 935 KeV |
| *In-114m | 50 days | 191–724 KeV |
| *Sn-119m | 250 days | 23–65 KeV |
| *Sn-121m | 76 years | 37 KeV |
| *Sb-124 | 60 days | 443 KeV |
| *Te-129m | 34 days | 487–696 KeV |

TABLE 12

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| *Ru-103 | 39.3 days | 497 KeV |

TABLE 12-continued

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| *Ag-107 | 5.0 years | 30–722 KeV |
| Sb-125 | 2.8 years | 427–636 KeV |
| I-129 | 1.6 × 107 years | 39.6 KeV |
| *Cs-134 | 2.0 years | 604–795 KeV |
| Cs-137 | 30.2 years | 662 KeV |
| Ce-144 | 284.4 days | 134 KeV |
| Pm-143 | 265.0 days | 742 KeV |
| Pm-145 | 17.7 years | 67.2 KeV |
| *Sm-145 | 340.0 days | 61.3 KeV |
| *Sm-151 | 93.0 years | 298 KeV |
| Eu-155 | 4.7 years | 105 KeV |
| Gd-153 | 241.6 days | 69–103 KeV |
| Dy-159 | 144.0 days | 326 KeV |
| *Tb-160 | 73.0 days | 298 KeV |
| *Tm-171 | 1.9 years | 66.7 KeV |
| Lu-173 | 1.4 years | 78–271 KeV |
| Lu-174 | 3.3 years | 76.6 KeV |
| Hf-172 | 1.87 years | 23.9–125 KeV |

TABLE 13

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Hf-175 | 70.0 days | 343 KeV |
| *Hf-178m2 | 31.0 years | 88.8–426 KeV |

TABLE 14

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Hf-179m2 | 25.1 days | 123–453 KeV |
| *Hf-181 | 42.4 days | 133–482 KeV |
| *Hf-182 | 9 × 10^6 years | 114–270 KeV |
| *W-185 | 74.8 days | 125 KeV |
| W-188 | 69.4 days | 63.6–291 KeV |
| Yb-169 | 32.0 days | 63.0–307 KeV |
| Re-183 | 70.0 days | 163 KeV |
| Os-194 | 6.0 years | 42.9 KeV |
| *Ir-192 | 73.8 days | 205–604 KeV |
| Ir-194m | 171.0 days | 328–688 KeV |
| *Hg-203 | 46.6 days | 279 KeV |
| Am-241 | 432.2 years | 59.5 KeV |
| *Bi-210M | 1000.0 years | 300 KeV |
| Am-242m | 141.0 years | 86.5 KeV |
| *Am-243 | 7.4 × 10^3 years | 74.7 KeV |
| Cm-241 | 32.8 days | 472 KeV |
| Cm-243 | 28.5 years | 228 KeV |
| Cm-245 | 8.5 × 10^3 years | 174 KeV |

TABLE 15

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Bk-247 | 1.4 × 10^3 years | 83.9–268 KeV |
| Cf-249 | 351 years | 388 KeV |

TABLE 16

RADIONUCLIDES FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| U-233 | 1.59 × 105 years | 42–97 KeV |
| U-234 | 2.45 × 105 years | 53 KeV (0.04% 121 KeV) |
| U-235 | 7.04 × 108 years | 185.7 KeV |
| U-236 | 2.34 × 107 years | 49.4–112.7 KeV |
| *U-238 | 4.46 × 109 years | 49.5 KeV |

TABLE 17

RADIONUCLIDES FOR ELECTRON-PRODUCING MULTILAYERED RADIOACTIVE MICROSPHERES
High Energy Electron Particle Radiation without Major Gamma-ray Component

| RADIONUCLIDE | HALF-LIFE | PARTICLE | ENERGY | GAMMA COMPONENT |
|---|---|---|---|---|
| Si-32 | 100.0 years | beta– | 213 KeV | — |
| P-32 | 14.3 days | beta– | 1.71 MeV | — |
| P-33 | 25.3 days | beta– | 249 KeV | — |
| Cl-36 | 3.0 × 105 years | beta– | 0.71 MeV | — |
| K-40 | 1.3 × 109 years | beta– | 1.31 MeV | annihilation rad 1.4 MeV 10% |
| K-42 | 12.4 hours | beta– | 3.52 MeV | 1.5 MeV 18.9% |
| Ca-45 | 163.8 days | beta– | 257 KeV | — |
| Ti-45 | 3.1 hours | beta+ | 1.04 MeV | annihilation rad |
| Cu-64 | 12.7 hours | beta– | 578 KeV | annihilation rad |
|  |  | beta+ | 650 KeV | 1.3 MeV 0.6% |
| Bi-210 | 5.0 days | beta– | 1.16 MeV | — |
| Sr-89 | 50.5 days | beta– | 1.49 MeV | 0.9 MeV 0.0009% |
| Sr-90 | 29.0 years | beta– | 546 KeV | — |
| S-35 | 87.2 days | beta= | 167 KeV | — |

TABLE 18

RADIONUCLIDES FOR ELECTRON-PRODUCING MULTILAYERED RADIOACTIVE MICROSPHERES
High Energy Electron Particle Radiation without Major Gamma-ray Component

| RADIONUCLIDE | HALF-LIFE | PARTICLE | ENERGY | GAMMA COMPONENT |
|---|---|---|---|---|
| Y-90 | 64.0 hours | beta– | 2.28 MeV | — |
| Zr-89 | 78.4 hours | beta+ | 0.90 MeV | annihilation rad 1.7 MeV 0.7% |
| Pd-112 | 21.0 hours | beta– | 280 KeV | 18.5 KeV 27% |
| Ag-111 | 7.47 days | beta– | 1.0 MeV | 0.34 MeV 6.7% |
| Cd-113m | 13.7 years | beta– | 590 KeV | 264 KeV 0.02% |
| Cd-115m | 44.6 days | beta– | 1.62 MeV | 1.2 MeV 0.9% |
| In-115 | 4.4 × 10^14 years | beta– | 348 KeV | — |
| Sn-123 | 129.2 days | beta– | 1.42 MeV | 1.08 MeV 0.6% |

TABLE 18-continued
RADIONUCLIDES FOR ELECTRON-PRODUCING MULTILAYERED RADIOACTIVE MICROSPHERES
High Energy Electron Particle Radiation without Major Gamma-ray Component

| RADIO-NUCLIDE | HALF-LIFE | PARTICLE | ENERGY | GAMMA COMPONENT |
|---|---|---|---|---|
| Cs-135 | 3.0 × 10$^6$ years | beta− | 205 KeV | — |
| Pr-139 | 4.4 hours | beta+ | 1.1 MeV | annihilation rad 1.6 MeV 0.3% |
| Pr-143 | 13.6 days | beta− | 935 KeV | 742 KeV 0.00001% |
| Er-169 | 9.6 days | beta= | 340 KeV | — |

TABLE 19
RADIONUCLIDES FOR ELECTRON-PRODUCING MULTILAYERED RADIOACTIVE MICROSPHERES
High Energy Electron Particle Radiation without Major Gamma-ray Component

| RADIO-NUCLIDE | HALF-LIFE | PARTICLE | ENERGY | GAMMA COMPONENT |
|---|---|---|---|---|
| Ho-166 | 1.1 days | beta− | 1.8 MeV | 80.5 KeV 6.0% 1.3 MeV 0.90% |
| Tm-170 | 128.6 days | beta− | 883 KeV | 84.3 KeV 3.3% |
| Yb-175 | 4.2 days | beta− | 467 KeV | 396 KeV 6.5% |
| Lu-177 | 6.7 days | beta− | 497 KeV | 208 KeV 11% |
| W-185 | 74.8 days | beta− | 433 KeV | 125 KeV 0.019% |
| W-188 | 69.4 days | beta− | 349 KeV | 291 KeV 0.40% |
| *Tl-204 | 3.8 years | beta− | 763 KeV | — |
| *Bi-210 | 5.0 days | beta− | 1.2 MeV | — |
| Th-231 | 25.2 hours | beta− | 305 KeV | 25.6 KeV 15% 84.2 KeV 6.6% |
| Th-234 | 24.1 days | beta− | 198 KeV | 63.3 KeV 3.8% 92.4 KeV 2.7% |
| Re-186 | 3.7 days | beta= | 1.07 MeV | — |

TABLE 20
MANUFACTURING PARAMETERS FOR LOW ENERGY PERMANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| As-73 | As-73 | Ar | As-73 |
| | As-73 Tribromide | Ar | As-73 Tribromide |
| | As-73 | Ar/Oxygen | As-73 Trioxide |
| | As-73 | Ar/Hydrogen Sulfide | As-73 Trisulfide |
| | Gallium | Ar/As-73H$_3$ | GaAs-73 |
| | Cobalt | Ar/As-73H$_3$ | Co$_2$As-73 |
| | Nickel | Ar/As-73H$_3$ | NiAs-73 |
| | Indium | Ar/As-73H$_3$ | InAs-73 |
| | Iron | Ar/As-73H$_3$ | FeAs-73 |
| | Tungsten | Ar/As-73H$_3$ | W(As-73)$_2$ |
| Se-72 | Se-72 | Ar | Se-72 |
| | Se-72 | Ar/Acetylene | Se-72 Carbide |
| | Se-72 | Ar/Nitrogen | Se-72 Nitride |
| | Se-72 | Ar/Oxygen | Se-72 Oxide |
| | Se-72 | Ar/Hydrogen Sulfide | Se-72 Sulfide |
| | Iridium | Ar/H$_2$Se-72 | Ir(Se-72)$_2$ |
| | Indium | Ar/H$_2$Se-72 | In$_2$(Se-72)$_3$ |
| | Thallium | Ar/H$_2$Se-72 | Tl$_2$Se-72 |

TABLE 21
MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| Pd-100 | Pd-100 | Ar | Pd-100 |
| *Pd-103 | Pd-103 | same as Pd-100 | |
| Pd-112 | Pd-112 | same as Pd-100 | |
| Te-123m | Te-123m | same as Te-125m | |
| Te-125m | Te-125m | Ar | Te-125m |
| Te-125m | | Ar/Oxygen | Te-125O$_3$ |
| Gallium | | Ar/H$_2$Te-125 | GaTe-125 |
| Lead | | Ar/H$_2$Te-125 | PbTe-125 |
| Indium | | Ar/H$_2$Te-125 | InTe-125 |
| Platinum | | Ar/H$_2$Te-125 | Pt(Te-125)$_2$ |
| Te-127m | Te-127m | same as Te-125m | |
| I-125 | CuI-125 | Ar | Copper iodide-125 |
| | AgI-125 | Ar | Silver iodide-125 |
| | KI-125 | Ar | Potassium iodide-125 |
| | Ti(I-125)$_2$ | Ar | Titanium di-iodide-125 |
| | Zr(I-125)$_4$ | Ar | Zirconium iodide-125 |
| | Hf(I-125)$_4$ | Ar | Hafnium iodide-125 |
| | Cr(I-125)$_2$ | Ar | Chromium iodide-125 |
| | Dy(I-125)$_3$ | Ar | Dysprosium iodide-125 |
| | Er(I-125)$_3$ | Ar | Erbium iodide-125 |

TABLE 22
MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| I-125 (continued) | Eu(I-125)$_2$ | Ar | Europium iodide-125 |
| | Ho(I-125)$_3$ | Ar | Holmium iodide-125 |
| | Li(I-125) | Ar | Lithium iodide-125 |
| | Lu(I-125)$_3$ | Ar | Lutetium iodide-125 |
| | Nd(I-125)$_3$ | Ar | Neodymium iodide-125 |
| | Rb(I-125) | Ar | Rubidium iodide-125 |
| | Sm(I-125)$_2$ | Ar | Samarium iodide-125 |
| | Tb(I-125)$_3$ | Ar | Terbium iodide-125 |
| | Titanium | Ar/(I-125)$_2$ Ar/HI-125 | Titanium di-iodide-125 |
| | Zirconium | Ar/(I-125)$_2$ Ar/HI-125 | Zirconium iodide-125 |
| | Hafnium | Ar/(I-125)$_2$ Ar/HI-125 | Hafnium iodide-125 |
| | Chromium | Ar/(I-125)$_2$ Ar/Hi-125 | Chromium iodide-125 |
| | Dysprosium | Ar/(I-125)$_2$ Ar/HI-125 | Dysprosium iodide-125 |
| | Erbium | Ar/(I-125)$_2$ Ar/HI-125 | Erbium iodide-125 |
| | Europium | Ar/(I-125)$_2$ Ar/HI-125 | Europium iodide-125 |

TABLE 23

MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| | Holmium | Ar/(I-125)$_2$ Ar/HI-125 | Holmium iodide-125 |
| | Lithium | Ar/(I-125)$_2$ Ar/HI-125 | Lithium iodide-125 |
| | Lutetium | Ar/(I-125)$_2$ Ar/HI-125 | Lutetium iodide-125 |
| | Neodymium | Ar/(I-125)$_2$ Ar/HI-125 | Neodymium iodide-125 |
| | Rubidium | Ar/(I-125)$_2$ Ar/HI-125 | Rubidium iodine-125 |
| | Samarium | Ar/(I-125)$_2$ Ar/HI-125 | Samarium iodide-125 |
| | Terbium | Ar/(I-125)$_2$ Ar/HI-125 | Terbium iodine-125 |
| *Ce-141 | Ce-141 | | |
| | Ce-141 fluoride | same as Ce-134 | |
| *Nd-147 | Nd-147 | Ar | Nd-147 |
| | Nd-147 bromide | Ar | Nd-147 bromide |
| | Nd-147 fluoride | Ar | Nd-147 fluoride |
| | Nd-147 | Ar/Acetylene | Nd-147 carbide |
| | Nd-147 | Ar/Nitrogen | Nd-147 nitride |
| | Nd-147 | Ar/Oxygen | Nd-147 oxide |
| | Nd-147 | Ar/Hydrogen Sulfide | Nd-147 sulfide |

TABLE 24

MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| Tb-155 | Tb-155 | Ar | Tb-155 |
| | Tb-155 bromide | Ar | Tb-155 bromide |
| | Tb-155 fluoride | Ar | Tb-155 fluoride |
| | Tb-155 | Ar/Oxygen | Tb-155 oxide |
| Tb-161 | Tb-161 | same as Tb-155 | |
| | Tb-161 bromide | | |
| | Tb-161 fluoride | | |
| | Tb-161 | | |
| Dy-166 | Dy-166 | Ar | Dy-166 |
| | Dy-166 bromide | Ar | Dy-166 bromide |
| | Dy-166 chloride | Ar | Dy-166 chloride |
| | Dy-166 fluoride | Ar | Dy-166 fluoride |
| | Dy-166 | Ar/Oxygen | Dy-166 oxide |
| Ho-166 | Ho-166 | Ar | Ho-166 |
| | Ho-166 bromide | Ar | Ho-166 bromide |
| | Ho-166 chloride | Ar | Ho-166 chloride |
| | Ho-166 | Ar/Oxygen | Ho-166 oxide |
| *Er-168 | Er-168 | | |
| | Er-168 fluoride | same as Er-169 | |
| *Tm-170 | Tm-170 | Ar | Tm-170 |
| | Tm-170 bromide | Ar | Tm-170 bromide |
| | Tm-170 fluoride | Ar | Tm-170 fluoride |
| | Tm-170 | Ar/Oxygen | Tm-170 oxide |
| Lu-176m | Lu-176m | same as Lu-177 | |
| | Lu-176m fluoride | | |

TABLE 25

MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| Sb-119 | Sb-119 | Ar | Sb-119 |
| | Tellurium | Ar/Sb-119H$_3$ | (Sb-119)$_2$Te$_3$ |
| | Indium | Ar/Sb-119H$_3$ | InSb-119 |
| *Pt-195m | Pt-195m | same as Pt-184 | |
| | Pt-195M phosphide | | |
| Hg-197 | Hg-197 fluoride | Ar | Hg-197 fluoride |
| | Hg-197 | Ar/Oxygen | Hg-197 oxide |
| Tl-201 | Tl-201 | Ar | Tl-201 |
| Th-231 | Th-231 | Ar | Th-231 |
| | Th-231 hexaboride | Ar | Th-231 hexaboride |
| | Th-231 | Ar/Acetylene | Th-231 carbide |
| | Th-231 | Ar/Oxygen | Th-231 oxide |
| | Th-231 | Ar/Hydrogen Sulfide | Th-231 sulfide |
| | Th-231 | Ar/B$_2$H$_6$ | |
| Th-234 | Th-234 | same as Th-231 | |
| | Th-234 hexaboride | | |
| | Th-234 | | |
| | Th-234 | | |
| | Th-234 | | |

TABLE 26

MANUFACTURING PARAMETERS FOR LOW ENERGY PERMANANENT MULTILAYERED RADIOACTIVE MICROSPHERES
(Main Gamma Energies less than 100 KeV, Half-Life less than 130 days)

| RADIONUC | TARGET MATERIAL | ATMOSPHERE GAS | COAT |
|---|---|---|---|
| Pu-237 | Pu-237 | Ar | Pu-237 |
| U-231 | U-231 | Ar | U-231 |
| | U-231 | Ar/B$_2$H$_6$ | U-231B$_2$ |
| | Boron | Ar/U-231F$_6$ | U-231B$_2$ |

TABLE 27

MANUFACTURING PARAMETERS FOR HIGH ENERGY PERMANANENT MULTILAYERED RADIOACTIVE MICROSPHERES
(Main Gamma Energies greater than 100 KeV, Half-Life less than 15 to 20 days)

| RADIONUC | TARGET MATERIAL | ATMOSPHERE GAS |
|---|---|---|
| As-74 | As-74 | same as As-73 |
| | As-74 Tribromide | |
| | As-74 | |
| | As-74 | |
| | Gallium | |
| | Cobalt | |
| | Nickel | |
| | Indium | |
| | Iron | |
| | Tungsten | |
| As-77 | As-77 | same as As-73 |
| | As-77 Tribromide | |
| | As-77 | |
| | As-77 | |
| | Gallium | |
| | Cobalt | |
| | Nickel | |
| | Indium | |
| | Iron | |
| | Tungsten | |

TABLE 27-continued

MANUFACTURING PARAMETERS FOR HIGH ENERGY PERMANANENT MULTILAYERED RADIOACTIVE MICROSPHERES
(Main Gamma Energies greater than 100 KeV, Half-Life less than 15 to 20 days)

| RADIONUC | TARGET MATERIAL | ATMOSPHERE GAS |
|---|---|---|
| Sc-47 | Sc-47 | Ar |

TABLE 28

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Zr-86 | Zr-86 | Ar | Zr-86 |
| | Zr-86 diboride | Ar | Zr-86 diboride |
| | Zr-86 | Ar/Acetylene | Zr-86 carbide |
| | Zr-86 | Ar/Nitrogen | Zr-86 nitride |
| | Zr-86 | Ar/Oxygen | Zr-86 oxide |
| | Zr-86 | Ar/Hydrogen Sulfide | Zr-86 sulfide |
| | Zr-86 | Ar/$B_2H_6$ | Zr-86 diboride |
| | Graphite | Ar/Zr-86$Cl_4$ | Zr-86 carbide |
| | Boron | AR/Zr-86$Cl_4$ | Zr-86 diboride |
| Sm-153 | Sm-153 | Ar | Sm-153 |
| | Sm-153 bromide | Ar | Sm-153 bromide |
| | Sm-153 fluoride | Ar | Sm-153 fluoride |
| Pb-203 | Pb-203 | Ar | Pb-203 |
| | Pb-203 fluoride | Ar | Pb-203 fluoride |
| V-48 | V-48 | Ar | V-48 |
| | V-48 | Ar/Acetylene | V-48 carbide |
| | V-48 | Ar/Nitrogen | V-48 nitride |
| | V-48 | Ar/Oxygen | V-48 oxide |
| | V-48 | Ar/Hydrogen Sulfide | V-48 sulfide |
| | V-48 | Ar/$B_2H_6$ | V-48$B_2$ |
| | Graphite | Ar/V-48$F_5$ | V-48 carbide |
| | Boron | Ar/V-48$Cl_4$ | V-48$B_2$ |

TABLE 29

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Cu-67 | Cu-67 | Ar | Cu-67 |
| | Cu-67 fluoride | Ar | Cu-67 fluoride |
| | Cu-67 | Ar/Oxygen | Cu-67 oxide |
| Ga-67 | Ga-67 | Ar | Ga-67 |
| | Tellurium | Ar/Ga-67$Cl_3$ | Ga-67 telluride |
| Br-77 | Samarium (Br-77)$_2$ | Ar | Samarium (Br-77)2 |
| | Neodymium (Br-77)3 | Ar | Neodymium (Br-77)3 |
| Sr-83 | Sr-83 | Ar | Sr-83 |
| | Sr-83 | Ar/Oxygen | Sr-83 oxide |
| | Sr-83 | Ar/Acetylene | Sr-83 carbide |
| Y-87 | Y-87 | Ar | Y-87 |
| | Y-87 chloride | Ar | Y-87 chloride |

TABLE 30

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Mo-99 | Mo-99 | Ar | Mo-99 |
| | Mo-99 | Ar/Acetylene | Mo-99 carbide |
| | Graphite | Ar/Mo-99$Cl_5$ | Mo-99 carbide |
| | Graphite | Ar/Mo-99$F_6$ | Mo-99 carbide |
| Ru-97 | Ru-97 | Ar | Ru-97 |
| Rh-105 | Rh-105 | Ar | Rh-105 |
| Cd-115 | Cd-115 fluoride | Ar | Cd-115 fluoride |
| | Cd-115 | Ar/Oxygen | Cd-115 oxide |
| | Cd-115 | Ar/Hydrogen Sulfide | Cd-115 sulfide |
| *Sn-117m | Sn-117m Tellurium | same as Sn-123 | |
| Te-132 | Te-132 | Ar | Te-132 |
| | Te-132 | Ar/Oxygen | Te-132 oxide |
| | Gallium | Ar/Te-132$H_2$ | GaTe-132 |
| | Lead | Ar/Te-132$H_2$ | PbTe-132 |
| | Indium | Ar/Te-132$H_2$ | InTe-132 |
| | Platinum | Ar/Te-132$H_2$ | Pt(Te-132)$_2$ |
| Cs-129 | Cs-129 bromide | Ar | Cs-129 bromide |
| | Cs-129 chloride | Ar | Cs-129 chloride |
| | Cs-129 fluoride | Ar | Cs-129 fluoride |
| | Cs-129 iodide | Ar | Cs-129 iodide |

TABLE 31

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Ag-111 | Ag-111 | Ar | Ag-111 |
| | Ag-111 chloride | Ar | Ag-111 chloride |
| | Ag-111 iodide | Ar | Ag-111 iodide |
| | Tellurium | Ar/Ag-111$N_3$ | (Ag-111)2Te |
| | Hg$I_2$ | Ar/Ag-111N3 | (Ag-111)2Hg$I_4$ |
| Te-121 | Te-121 Te-121 Gallium Lead Indium Platinum | same as Te-132 | |
| I-131 | CuI-131 AgI-131 KI-131 Ti(I-131)$_2$ Zr(I-131)$_4$ Hf(I-131)$_4$ Cr(I-131)$_2$ Dy(I-131)$_3$ Er(I-131)$_3$ Eu(I-131)$_2$ Ho(I-131)$_3$ | same as I-125 | |

TABLE 32

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| I-131 | Li(I-131) Lu(I-131)$_3$ Nd(I-131)$_3$ Rb(I-131) Sm(I-131)$_2$ Tb(I-131)$_3$ | same as I-125 | |

TABLE 32-continued
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| | Titanium | | |
| | Zirconium | | |
| | Hafnium | | |
| | Chromium | | |
| | Dysprosium | | |
| | Erbium | | |
| | Europium | | |
| | Holmium | | |
| | Lithium | | |
| | Lutetium | | |
| | Neodymium | | |
| | Rubidium | | |
| | Samarium | | |
| | Terbium | | |

TABLE 33
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Ba-128 | Ba-128 chloride | Ar | Ba-128 chloride |
| | Ba-128 fluoride | Ar | Ba-128 fluoride |
| | Ba-128 | Ar/Oxygen | Ba-128 oxide |
| Ba-131 | Ba-131 chloride | same as Ba-128 | |
| | Ba-131 fluoride | | |
| | Ba-128 | | |
| Ba-140 | Ba-140 chloride | same as Ba-128 | |
| | Ba-140 fluoride | | |
| | Ba-140 | | |
| Ce-134 | Ce-134 | Ar | Ce-134 |
| | Ce-134 fluoride | Ar | Ce-134 fluoride |
| | Ce-134 | Ar/Oxygen | Ce-134 oxide |
| Nd-138 | Nd-138 | same as Nd-147 | |
| | Nd-138 bromide | | |
| | Nd-138 fluoride | | |
| | Nd-138 | | |
| | Nd-138 | | |
| | Nd-138 | | |
| | Nd-138 | | |
| *Ce-141 | Ce-141 | same as Ce-134 | |
| | Ce-141 fluoride | | |

TABLE 34
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Pm-151 | Pm-151 | Ar | Pm-151 |
| Tb-155 | see previous Tb-155 entry | | |
| Dy-157 | Dy-157 | same as Dy-166 | |
| | Dy-157 bromide | | |
| | Dy-157 chloride | | |
| | Dy-157 fluoride | | |
| | Dy-166 | | |
| Yb-175 | Yb-175 | Ar | Yb-175 |
| | Yb-175 bromide | Ar | Yb-175 bromide |
| | Yb-175 fluoride | Ar | Yb-175 fluoride |
| *Os-191 | Os-191 | Ar | Os-191 |
| Pt-184 | Pt-184 | Ar | Pt-184 |

TABLE 34-continued
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| | Pt-184 phosphide | Ar | Pt-184 phosphide |
| Pr-143 | Pr-143 | Ar | Pr-143 |
| | Pr-143 fluoride | Ar | Pr-143 fluoride |
| | Pr-143 | Ar/Oxygen | Pr-143 oxide |

TABLE 35
MANUFACTURING PARAMETERS FOR HIGH ENERGY PERMANANENT MULTILAYERED RADIOACTIVE MICROSPHERES
(Main Gamma Energies less than 100 KeV, Half-Life less than 15 to 20 days)

| RADIONUC | TARGET MATERIAL | ATMOSPHERE GAS | COAT |
|---|---|---|---|
| Gd-149 | Gd-149 | Ar | Gd-149 |
| | Gd-149 iodide | Ar | Gd-149 iodide |
| Er-169 | Er-169 | Ar | Er-169 |
| | Er-169 fluoride | Ar | Er-169 fluoride |
| Tm-167 | Tm-167 | same as Tm-170 | |
| | Tm-167 bromide | | |
| | Tm-167 fluoride | | |
| | Tm-167 | | |
| Hf-170 | Hf-170 | Ar | Hf-170 |
| | Hf-170 | Ar/Acetylene | Hf-170 carbide |
| | Hf-170 | Ar/Nitrogen | Hf-170 nitride |
| | Hf-170 | Ar/Oxygen | Hg-170 oxide |
| Hf-171 | Hf-171 | same as Hf-170 | |
| | Hf-171 | | |
| | Hf-171 | | |
| | Hf-171 | | |
| Hf-173 | Hf-173 | same as Hf-170 | |
| | Hf-173 | | |
| | Hf-173 | | |
| | Hf-173 | | |

TABLE 36
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Hf-184 | Hf-184 | same as Hf-170 | |
| | Hf-184 | | |
| | Hf-184 | | |
| | Hf-184 | | |
| Re-181 | Re-181 | Ar | Re-181 |
| Re-188 | Re-188 | same as Re-181 | |
| Re-189 | Re-189 | same as Re-181 | |
| Lu-177 | Lu-177 | Ar | Lu-177 |
| | Lu-177 fluoride | Ar | Lu-177 fluoride |
| Ta-177 | Ta-177 | Ar | Ta-177 |
| | Ta-177 | Ar/Acetylene | Ta-177 carbide |
| | Ta-177 | Ar/B$_2$H$_6$ | Ta-177 boride |
| | Boron | Ar/Ta-177F$_8$ | Ta-177 boride |
| | Graphite | AR/Ta-177F$_8$ | Ta-177 carbide |
| Ta-180m | Ta-180m | same as Ta-177 | |
| | Ta-180m | | |
| | Ta-180m | | |
| | Boron | | |
| | Graphite | | |

TABLE 37
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Ta-183 | Ta-183 | same as Ta-177 | |
| | Ta-183 | | |
| | Ta-177 | | |
| | Boron | | |
| | Graphite | | |
| W-187 | W-187 | Ar | W-187 |
| | W-187 | Ar/Acetylene | W-187 carbide |
| | W-187 | Ar/$B_2H_6$ | W-187 Boride |
| | Boron | Ar/W-187$Cl_5$ | W-187 Boride |
| | Graphite | Ar/W-187$F_6$ | W-187 carbide |
| Ir-189 | Ir-189 | Ar | Ir-189 |
| Pt-191 | Pt-191 | same as Pt-184 | |
| | Pt-191 phosphide | | |
| Au-193 | Au-193 | Ar | Au-193 |
| | Tellurium | Ar/Au-193$Cl_2$ | Au-193$Te_2$ |
| *Au-198 | Au-198 | same as Au-193 | |
| | Tellurium | | |

TABLE 38
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Au-199 | Au-199 | same as Au-193 | |
| | Tellurium | | |
| Hg-195m | Hg-195m fluoride | same as Hg-197 | |
| | Hg-195m | | |
| Hg-197m | Hg-197m fluoride | same as Hg-197 | |
| | Hg-197m | | |
| Tl-201 | Tl-201 | Ar | Tl-201 |
| | Vanadium | Ar/$O_2$/Tl-201$NO_3$ | Tl201$VO_3$ |
| Tl-202 | Tl-202 | Same as Tl-201 | |
| | Vanadium | | |
| Pb-100 | Pb-100 | same as Pb-203 | |
| | Pb-100 fluoride | | |
| Nb-90 | Nb-90 | Ar | Nb-90 |
| | Nb-90 | Ar/Acetylene | Nb-90 carbide |
| | Nb-90 | Ar/$B_2H_6$ | Nb-90 boride |
| | Boron | Ar/Nb-90$Cl_5$ | Nb-90 boride |
| | Graphite | Ar/Nb-90$F_5$ | Nb-90 carbide |

TABLE 39
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Nb-92m | Nb-92 | same as Nb-90 | |
| | Nb-92 | | |
| | Nb-92 | | |
| | Boron | | |
| | Graphite | | |
| Nb-96 | Nb-96 | same as Nb-90 | |
| | Nb-96 | | |
| | Nb-96 | | |
| | Boron | | |
| | Graphite | | |
| Bk-245 | Bk-245 | Ar | Bk-245 |
| Bk-246 | Bk-246 | same as Bk-245 | |
| Bk-247 | Bk-247 | same as Bk-245 | |

TABLE 39-continued
MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Cf-249 | Cf-249 | Ar | Cf-249 |
| Es-254m | Es-245m | Ar | Es-254m |
| U-237 | U-237 | same as U-231 | |
| | U-237 | | |
| | Boron | | |

TABLE 40
MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Be-7 | Be-7 | Ar | Be-7 |
| | Be-7 | Ar/Nitrogen | Be-7 nitride |
| | Be-7 | Ar/Oxygen | Be-7 oxide |
| | Be-7 | Ar/Acetylene | Be-7 oxide |
| Sc-46 | Sc-46 | same as Sc-47 | |
| Co-57 | Co-57 | Ar | Co-57 |
| | Co-57 fluoride | Ar | Co-57 fluoride |
| | Co-57 | Ar/oxygen | Co-57 oxide |
| Rb-83 | Rb-83 bromide | Ar | Rb-83 bromide |
| | Rb-83 chloride | Ar | Rb-83 chloride |
| | Rb-83 iodide | Ar | Rb-83 iodide |
| Sr-85 | Sr-85 | same as Sr-83 | |
| | Sr-85 | | |
| | Sr-85 | | |
| Ti-44 | Ti-44 | Ar | Ti-44 |
| | Ti-44 | Ar/Acetylene | Ti-44 carbide |
| | Ti-44 | Ar/Nitrogen | Ti-44 nitride |
| | Ti-44 | Ar/$B_2H_6$ | Ti-44 boride |
| Cr-51 | Cr-51 | Ar | Cr-51 |
| | Cr-51 | Ar/Acetylene | Cr-51 carbide |
| | Cr-51 | Ar/$H_2S$ | Cr-51 sulfide |

TABLE 41
MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Se-75 | Se-72 | same as Se-72 | |
| | Se-72 | | |
| | Se-72 | | |
| | Se-72 | | |
| | Se-72 | | |
| | Iridium | | |
| | Indium | | |
| | Thallium | | |
| Zr-88 | Zr-88 | same as Zr-86 | |
| | Zr-88 diboride | | |
| | Zr-88 | | |
| | Zr-88 | | |
| | Zr-88 | | |
| | Zr-88 | | |
| | Zr-88 | | |
| | Graphite | | |
| | Boron | | |
| Zr-93 | Zr-93 | same as Zr-86 | |
| | Zr-93 diboride | | |
| | Zr-93 | | |
| | Zr-93 | | |
| | Zr-93 | | |

TABLE 41-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| | Zr-93 | | |
| | Zr-93 | | |
| | Graphite | | |
| | Boron | | |

TABLE 42

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Zr-95 | Zr-95 | same as Zr-86 | |
| | Zr-95 diboride | | |
| | Zr-95 | | |
| | Zr-95 | | |
| | Zr-95 | | |
| | Zr-95 | | |
| | Zr-95 | | |
| | Graphite | | |
| | Boron | | |
| La-138 | La-138 | Ar | La-138 |
| | La-138 | Ar/Oxygen | La-138 oxide |
| | La-138 | Ar/$B_2H_6$ | La-138 boride |
| | Boron | Ar/La-138$Cl_3$ | La-138$B_6$ |
| Gd-146 | Gd-146 | same as Gd-149 | |
| | Gd-146 iodide | | |
| Nb-92 | Nb-92 | same as Nb-90 | |
| | Nb-92 | | |
| | Nb-92 | | |
| | Boron | | |
| | Graphite | | |
| *Cd-109 | Cd-109 fluoride | same as Cd-115 | |
| | Cd-109 | | |
| | Cd-109 | | |
| *Cd-115m | Cd-115m | same as Cd-115 | |
| *In-114m | In-114m | same as In-115 | |

TABLE 43

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Sn-119m | Sn-119m | same as Sn-123 | |
| | Sn-119m | | |
| | Sn-119m | | |
| | Tellurium | | |
| *Sn-121m | Sn-121m | same as Sn-123 | |
| | Sn-121m | | |
| | Sn-121m | | |
| | Tellurium | | |

TABLE 44

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Nb-93m | Nb-93m | samae as Nb-90 | |
| | Nb-93 | | |

TABLE 44-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| | Nb-93 | | |
| | Boron | | |
| | Graphite | | |
| Nb-94 | Nb-94 | same as Nb-90 | |
| | Nb-94 | | |
| | Nb-94 | | |
| | Boron | | |
| | Graphite | | |
| Nb-95 | Nb-95 | same as Nb-90 | |
| | Nb-95 | | |
| | Nb-95 | | |
| | Boron | | |
| | Graphite | | |
| *Mo-93 | Mo-93 | same as Mo-99 | |
| | Mo-93 | | |
| | Graphite | | |
| | Graphite | | |
| Sb-125 | Sb-125 | same as Sb-119 | |
| | Tellurium | | |
| | Indium | | |
| *Sb-124 | Sb-124 | same as Sb-119 | |
| | Tellurium | | |
| | Indium | | |

TABLE 45

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Te-129m | Te-129m | same as Te-132 | |
| | Te-129m | | |
| | Gallium | | |
| | Lead | | |
| | Indium | | |
| *Ru-103 | Ru-103 | same as Ru-97 | |

TABLE 46

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| I-129 | CuI-129 | same as I-125 | |
| | AgI-129 | | |
| | KI-129 | | |
| | Ti(I-129)$_2$ | | |
| | Zr(I-129)$_4$ | | |
| | Hf(I-129)$_4$ | | |
| | Cr(I-129)$_2$ | | |
| | Dy(I-129)$_3$ | | |
| | Er(I-129)$_3$ | | |
| | Eu(I-129)$_2$ | | |
| | Ho(I-129)$_3$ | | |
| | Li(I-129) | | |
| | Lu(I-129)$_3$ | | |
| | Nd(I-129)$_3$ | | |
| | Rb(I-129) | | |
| | Sm(I-129)$_2$ | | |
| | Tb(I-129)$_3$ | | |
| | Titanium | | |
| | Zirconium | | |
| | Hafnium | | |
| | Chromium | | |

TABLE 46-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
|  | Dysprosium |  |  |

TABLE 47

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| I-129 | Erbium | same as I-125 |  |
|  | Europium |  |  |
|  | Holmium |  |  |
|  | Lithium |  |  |
|  | Lutetium |  |  |
|  | Neodymium |  |  |
|  | Rubidium |  |  |
|  | Samarium |  |  |
|  | Terbium |  |  |
| Cs-137 | Cs-137 bromide | same as Cs-129 |  |
|  | Cs-137 chloride |  |  |
|  | Cs-137 fluoride |  |  |
|  | Cs-137 iodide |  |  |

TABLE 48

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Ce-144 | Ce-144 | same as Ce-134 |  |
|  | Ce-144 fluoride |  |  |
|  | Ce-144 |  |  |
| Pm-143 | Pm-143 | Ar | Pm-143 |
| Pm-145 | Pm-145 | same as Pm-143 |  |
| *Sm-145 | Sm-145 | same as Sm-153 |  |
|  | Sm-145 bromide |  |  |
|  | Sm-145 fluoride |  |  |
| Eu-155 | Eu-155 | Ar | Eu-155 |
|  | Eu-155 fluoride | Ar | Eu-155 fluoride |
| Gd-153 | Gd-153 | same as Gd-149 |  |
|  | Gd-153 iodide |  |  |
| Dy-159 | Dy-159 | same as Dy-166 |  |
|  | Dy-159 bromide |  |  |
|  | Dy-159 chloride |  |  |
|  | Dy-159 fluoride |  |  |
| *Tm-171 | Tm-171 | same as Tm-170 |  |
|  | Tm-171 bromide |  |  |
|  | Tm-171 fluoride |  |  |
|  | Tm-171 |  |  |
| *Sm-151 | Sm-151 | same as Sm-153 |  |
|  | Sm-151 bromide |  |  |
|  | Sm-151 fluoride |  |  |

TABLE 49

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Tb-160 | Tb-160 | same as Tb-155 |  |
|  | Tb-160 bromide |  |  |

TABLE 49-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
|  | Tb-160 fluoride |  |  |
|  | Tb-160 |  |  |

TABLE 50

MANUFACTURE FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Lu-173 | Lu-173 | Ar | Lu-173 |
|  | Lu-173 fluoride | Ar | Lu-173 fluoride |
| Lu-174 | Lu-174 | same as Lu-173 |  |
|  | Lu-174 fluoride |  |  |
| Hf-172 | Hf-172 | same as Hf-170 |  |
|  | Hf-172 |  |  |
|  | Hf-172 |  |  |
|  | Hf-172 |  |  |
| Hf-175 | Hf-175 | same as Hf-170 |  |
|  | Hf-175 |  |  |
|  | Hf-175 |  |  |
|  | Hf-175 |  |  |
| *Hf-178m2 | Hf-178m2 | same as Hf-170 |  |
|  | Hf-178m2 |  |  |
|  | Hf-178m2 |  |  |
|  | Hf-178m2 |  |  |

TABLE 51

MANUFACTURE FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Hf-179m2 | Hf-179m2 | same as Hf-170 |  |
|  | Hf-179m2 |  |  |
|  | Hf-179m2 |  |  |
|  | Hf-179m2 |  |  |
| *Hf-181 | Hf-181 | same as Hf-170 |  |
|  | Hf-181 |  |  |
|  | Hf-181 |  |  |
|  | Hf-181 |  |  |
| *Hf-182 | Hf-182 | same as Hf-170 |  |
|  | Hf-182 |  |  |
|  | Hf-182 |  |  |
|  | Hf-182 |  |  |
| *W-185 | Hf-185 | same as W-187 |  |
|  | Hf-185 |  |  |
|  | Hf-185 |  |  |
|  | Hf-185 |  |  |
| W-188 | W-188 | same as W-187 |  |
|  | W-188 |  |  |
| Re-183 | Re-183 | same as Re-181 |  |
| Os-194 | Os-194 | same as Os-191 |  |

TABLE 52

MANUFACTURE FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Ir-192 | Ir-192 | same as Ir-189 |  |
| Ir-194m | Ir-194m | same as Ir-189 |  |

TABLE 52-continued

MANUFACTURE FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Hg-203 | Hg-203 fluoride | same as Hg-197 | |
| | Hg-203 | | |
| *Bi-210m | Bi-210m | same as Bi-210 | |
| | Bi-210m Tellurium | | |
| Am-241 | Am-241 | Ar | Am-241 |
| Am-242m | Am-242m | same as Am-241 | |
| *Am-243 | Am-243 | same as Am-241 | |
| Cm-243 | Cm-243 | Ar | Cm-243 |
| Cm-245 | Cm-245 | same as Cm-243 | |
| U-233 | U-233 | same as U-231 | |
| | U-233 Boron | | |
| U-234 | U-234 | same as U-231 | |
| | U-234 Boron | | |

TABLE 53

MANUFACTURE FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| U-235 | U-235 | same as U-231 | |
| | U-235 Boron | | |
| U-236 | U-236 | same as U-231 | |
| | U-236 Boron | | |
| *U-238 | U-238 | same as U-231 | |
| | U-238 Boron | | |

TABLE 54

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Si-32 | Si-32 | Ar | Si-32 |
| | Si-32 | Ar/Acetylene | Si-32 carbide |
| | Si-32 | Ar/Oxygen | Si-32 oxide |
| | Graphite | Ar/Si-32H$^4$ | NiSi-32 |
| P-32 | Platinum (P-32)2 | Ar | Platinum phosphide-32 |
| | Platinum | Ar/H$_3$P-32 | Platinum (P-32)$_2$ |
| P-33 | Platinum(P-33)2 | same as P-32 | |
| | Platinum | | |
| Cl-36 | Neodymium (Cl-36)$_3$ | Ar | Neodymium chloride-36 |
| | Holmium (Cl-36)3 | Ar | holmium chloride-36 |
| K-40 | K-40 chloride | Ar | K-40 chloride |
| | K-40 iodide | Ar | K-40 iodide |
| K-42 | K-42 chloride | same as K-40 | |
| | K-42 iodide | | |
| Ca-45 | Ca-45 | Ar | Ca-45 |
| | Ca-45 fluoride | Ar | Ca-45 fluoride |
| | Ca-45 | Ar/Acetylene | Ca-45 carbide |
| S-35 | Vanadium | Ar/H2$^{S-35}$ | VS-35 |
| | Tungsten | Ar/H2$^{S-35}$ | W(S-35)z |

TABLE 55

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Ti-45 | Ti-45 | same as Ti-44 | |
| | Ti-45 | | |
| | Ti-45 | | |
| | Ti-45 | | |
| Bi-210 | Bi-210 | Ar | Bi-210 |
| | Bi-210 | Ar/Oxygen | Bi-210 oxide |
| | Tellurium | H$_3$Bi | (BI-310)2Te3 |
| Sr-89 | Sr-89 | Same as Sr-83 | |
| | Sr-89 | | |
| | Sr-89 | | |
| Sr-90 | Sr-90 | same as Sr-83 | |
| | Sr-90 | | |
| | Sr-90 | | |
| Y-90 | Y-90 | same as Y-87 | |
| | Y-90 chloride | | |
| Zr-89 | Zr-89 | same as Zr-86 | |
| | Zr-89 diboride | | |
| | Zr-89 | | |
| | Zr-89 | | |
| | Zr-89 | | |
| | Zr-89 | | |
| | Zr-89 | | |
| | Graphite | | |
| | Boron | | |

TABLE 56

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Pd-112 | Pd-112 | same as Pd-100 | |
| Ag-111 | see Ag-111 previous entry | | |
| Cd-113m | Cd-113m fluoride | same as Cd-115 | |
| | Cd-113m | | |
| | Cd-113m | | |
| Cd-115m | Cd-115m fluoride | same as Cd-115 | |
| | Cd-115m | | |
| | Cd-115m | | |
| In-115 | In-115 | Ar | In-115 |

TABLE 56-continued

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Sn-123 | Sn-123 | Ar | Sn-123 |
|  | Sn-123 | Ar/Oxygen | Sn-123 oxide |
|  | Sn-123 | Ar/hydrogen sulfide | Sn-123 sulfide |
|  | Tellurium | Ar/Sn-123H$_4$ |  |
| Cs-135 | Cs-135 bromide | same as Cs-129 |  |
|  | Cs-135 chloride |  |  |
|  | Cs-135 fluoride |  |  |
|  | Cs-135 iodide |  |  |
| Pr-143 | see previous Pr-143 entry |  |  |
| Ho-166 | see previous Ho-166 entry |  |  |

TABLE 57

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Tm-170 | see previous Tm-170 entry |  |  |
| Yb-175 | see previous Yb-175 entry |  |  |
| Lu-177 | Lu-177 | same as Lu-173 |  |
|  | Lu-177 fluoride |  |  |
| W-185 | W-185 | same as W-187 |  |
|  | W-185 |  |  |
|  | W-187 |  |  |
|  | Boron |  |  |
|  | Graphite |  |  |
| W-188 | W-188 | same as W-187 |  |
|  | W-188 |  |  |
|  | W-188 |  |  |
|  | Boron |  |  |
|  | Graphite |  |  |
| *Tl-204 | Tl-204 | same as Tl-201 |  |
|  | Vanadium |  |  |
| Th-231 | Th-231 | same as Th-231 |  |
|  | Th-231 hexaboride |  |  |
|  | Th-231 |  |  |
|  | Th-231 |  |  |
|  | Th-231 |  |  |

TABLE 58

MANUFACTURE FOR ELECTRON-PRODUCING MULTILAYERED RADIOACTIVE MICROSPHERES
High Energy Electron Particle Radiation without Major Gamma-ray Component

| RADIONUC | TARGET MATERIAL | ATMOSPHERE GAS | COAT |
|---|---|---|---|
| Th-234 | Th-234 | Same as Th-231 |  |
|  | Th-234 hexaboride |  |  |
|  | Th-234 |  |  |
|  | Th-234 |  |  |
|  | Th-234 |  |  |
|  | Th-234 |  |  |

*footnote for tables 4-58: "Radioisotope can be created from natural element by neutron irradiation of corresponding naturally-occurring non-radioactive isotope, thus allowing manufacture of the finished non-radioactive microsphere with later conversion to the radioactive product by activating the seeds in a 'neutron oven'."

This material of layer 16 is atomically bound to the central section 12 and to the layer above it and in some cases such as sputtered metal layers and their nitrides, carbides or oxides, have hardness and durability that are several times higher than similar bulk metals. Generally, each layer is bound atomically to the material in the layers on either side of it.

The radiation emitting layer 16 may be a radiation emitting compound layer (such as thallium selenide-72, antimony telluride-119, uranium boride-231, zirconium carbide-86, copper iodide-125, Mo carbide-99, tantalum carbide-177, vanadium carbide-48, gallium telluride-67, indium telluride-125m, titanium iodide-125, or copper indium selenium-75) laminated with a hard metal (tantalum, tungsten, titanium, hafnium, zirconium, diamond-like carbon, niobium, osmium), metal compound (titanium nitride, titanium carbonitride, zirconium nitride, zirconium carbide, tantalum carbide, tungsten carbide, boron carbide, chromium dicarbide, hafnium carbide, hafnium oxide, lanthanum oxide, thorium carbide, vanadium carbide, hafnium nitride), or nonmetal (diamond or carbon) diffusion barrier. This laminated radiation-emitting coat uniformly covers the solid microspherical metal or carbon core (substrate).

In one embodiment, pure metal is deposited onto microspherical substrates from plasma in an atmosphere containing only an inert gas and a radiation-emitting chemical compound is deposited onto microspherical substrates when a radiation-emitting reactive gas such as a radioactive hydride gas is introduced into the system to form a radioactive compound from the metal and gas. In another embodiment, cycles of different coating materials are alternated to produce a laminate of thin hard (high boiling point metal) and soft (radiation-emitting compound) coats such as for example of the materials described above. Using adequate biasing of the substrate, each cycle is approximately thirty seconds in duration so that one layer of radiation-emitting compound is sealed by one layer of pure (high boiling point) metal each sixty seconds.

Depending on the materials being coated and the efficiency of the deposition apparatus, each alternate layer is approximately 100 Angstroms to 1000 Angstroms thick, depending on the coating method used as well as the apparatus and atomic weights of the elements being coated. The coating of the soft radiation-emitting layer with a hard-metal layer seals the radiation-emitting layer before it begins to break or vacuum weld with other microspheres. This is continued using one of the coating methods outlined hereinafter until the desired activity or radiation-emitting compound is accumulated on the microsphere. A laminate of thin hard (metal nitride, metal oxide, metal carbide, or metal carbonitride) and soft (metal-radionuclide compound) coats are produced.

The outer layers 18 and 20 confine the radiation-emitting layer 16. In one embodiment, these layers are made of a material that permits the transmission of electrons through them such as carbon thus permitting electron seeds by the appropriate selection of the material for the layer 16 but in other embodiments are made of metals that are hard and protective but absorb or filter electron particles. These materials in layers 18 and 20 are included in embodiments with radiation-emitting materials in the layer 16 to protect, seal, identify and under some circumstances provide filtering of radiation.

In some embodiments, the layer 18 is a diffusion barrier that prevents the movement of radioactivity outwardly toward the suface of the microsphere 10. The outer layer may serve as both diffusion barrier and provide mechanical protection or color identification if desired. The material of the diffusion barrier is selected for its functions in conjuction with the nature of the material that provides the radiation.

Suitable diffusion barriers include: (1) single metals such as gold, palladium, tantalum, tungsten, platinum, and titanium; or (2) multilayered combinations of metals such as gold-palladium-titanium, gold-titanium and tungsten-titanium; or (3) compounds such as titanium nitride (TIN), and titanium carbide (TIC), tungsten carbide (WC), tungsten nitride (WN), tungsten-titanium nitride (TiWN), hafnium nitride (HfN), hafnium carbide (HfC), zirconium nitride (ZrN), zirconium carbide (ZrC), vanadium carbide (VC), boron carbide (BC) and tungsten boride (WB); or (4) nonmetallic elements or compounds such as diamond or diamond-like carbon.

The preferred diffusion barrier materials of the present invention are titanium nitride, tungsten carbide, hafnium nitride and groups of layers such as a titanium layer 100 nm (nanometers) thick, a layer of palladium 100 nm thick, and a layer of gold 300 nm thick. The purpose of the diffusion barrier is to prevent difusion of the radiation-emitting component into the outer coats of the multilayer radiation-emitting microsphere. It also serves as a radiation -emitting gas barrier for radionuclides which sublimate or form gases at room temperature.

An essential criterion of thin film structures is that they maintain structural integrity. Pronounced reaction or interdiffusion of thin films is known to occur over short distances of several hundred angstroms. Thin metal layers tend to diffuse and react chemically, and this tendency is enhanced by thin film defects or grain boundaries. The diffusion barrier helps prevent this diffusion.

It is important to prevent radiation-emitting materials from diffusing through the outer metal coats of the multilayer radiation-emitting microsphere because metals such as I-125 can sublimate into a gas upon exposure to air, or if they are implanted into a patient, the I-125 can enter the bloodstream and become concentrated in the thyroid gland. Diffusion barriers are not necessary when the radionuclide element is a chemically stable or high boiling point metal or metal compound that is relatively inert.

The outer coat 20 is a thick spherical (up to 0.10 mm) protective coat containing the inner coats 16 and 18. The spherical thick protective coat may be composed of: (1) a resistant human tissue-compatible metal which also has low atomic weight to minimize X-ray shielding such as titanium or other corrosion-resistant metal alloy such as stainless steel; or (2) a resistant human tissue-compatible metal compound (using reactive acetylene nitrogen, oxygen, methane, or carbon monoxide gases during coating to form carbides, nitrides, or carbonitrides of transition metals or other metals) such as titanium carbide, titanium nitride, titanium carbonitride, titanium aluminum nitride, zirconium nitride and hafnium nitride; or (3) a resistant human tissue-compatible metal coat less than 0.1 millimeters thick which has a high atomic weight such as tantalum, platinum or gold; or (4) a human tissue-incompatible metal coat which is covered by a tissue-compatible thin coat.

If a tissue-compatible outermost coat such as sputtered diamond, tantalum, or titanium is applied over the thick protective metal casing, then the more toxic but low atomic weight metals such as beryllium, vanadium, nickel and boron nitride may be used as the thick casing. Appropriate outermost coat are typically thin and consist of a special-purpose coat designed to enhance physical properties of the seed such as diamond or diamond-like carbon, platinum, or tantalum. These coats individually enhance the multilayer radiation-emitting microsphere by adding hardness, and corrosion resistance. The outermost thin coat may also be used to produce different seed identification colors.

To produce color, the outermost thin coat may include of titanium nitride (TIN) to produce a golden color, titanium carbonitride (TiCN) to produce a brown color, titanium aluminum nitride (TiAlN) to produce a black color, titanium carbide (TIC) to produce a gray color, zirconium nitride (ZrN) to produce a silver-yellow color, and hafnium nitride (HfN) to produce a yellow-green color.

Some appropriate strong hard corrosion-resistant human tissue-compatible metal include titanium, hafnium, and zirconium. Low atomic weight metal alloys such as stainless steel are also satisfactory. Other usable corrosion-resistant metals include tantalum, tungsten, gold, and platinum. Because this "thick" layer is still relatively thin (less than 0.1 mm) and because the coat is highly uniform and spherical, a high atomic weight metal such as platinum or gold may still be effectively used as the thick protective coat without causing radiation aniostropy and with minimal gamma-ray shielding and loss of radioactivty.

Because of spherical uniform construction, any self-shielding can be compensated for by increasing the seed activity. In the preferred embodiment of this invention, metals having low atomic weight with minimal shielding of low-energy gamma rays, tissue and corrosion resistance, high hardness and high boiling point are preferred for the casing of multilayer radiation-emitting microsphere's containing low energy emitting (less than 100 KeV) radionuclides. Titanium is such a metal. The preferred metal for casings of multilayer radiation-emitting microsphere's containing high energy emitting (greater than 100 KeV) radionuclides have high atomic weight with some shielding of low energy gamma rays and very little shielding of high energy gamma rays, high tissue and corrosion resistance, high hardness and very high boiling point. Two such metals are tantalum and tungsten.

The casing 20 also may include a strong hard corrosion-resistant human tissue-compatible non-metallic element. The preferred non-metallic thick protective coat is sputtered or plasma-deposited diamond or plasma-deposited diamond-like carbon. These non-metallic coats not only have the advantage of low atomic weight to minimize X-ray self-shielding of the radionuclide layer, but they also have the advantage of being completely non-ferromagnetic.

Other hard corrosion-resistant metals include carbides, metal nitrides, metal borides, metal oxides, metal sulfides, or metal carbonitrides. The preferred metallic compound thick protective coats of the present invention include titanium carbide, titanium nitride, titanium carbonitride, tantalum carbide, tungsten carbide, hafnium nitride, and zirconium nitride.

All of these thick coats may be incorporated individually into different seed designs to adequately serve as a hard crush-resistant corrosion-resistant protective outer casing of the multilayer radiation-emitting microsphere. All of these coats may be easily applied by the standard deposition or reactive deposition techniques described elsewhere.

Additionally, if a tissue-compatible outermost coat such as sputtered diamond, tantalum, or titanium is applied over the thick protective metal casing, then the thick protective layer need not be composed of a tissue-compatible material. In this case, more toxic but low atomic weight metals such as beryllium, vanadium, nickel and boron nitride may be used as the thick protective casing.

Additionally, if a tissue-compatible outermost coat such as sputtered diamond, tantalum, or titanium is applied over the thick protective metal casing, then the thick protective layer need not be composed of a tissue-compatible material. In this case, more toxic but low atomic weight metals such as beryllium, vanadium, nickel and boron nitride may be used as the thick protective casing.

In FIGS. 2-5, there are shown four other embodiments of radiation-emitting microspheres 10A, 10B, 10C and 10D respectively having corresponding layer sections 14A-14D with different numbers of and/or thicknesses of its layers or coats, ranging from four coats to five coats but normally with one thick protective coat and several thin coats so as to minimize the diameter of the radiation-emitting microsphere. The microsphere 10A of FIG. 2 has a hollow substrate 12A but would include a solid spherical substrate instead. For convenience the coats are numbered from the center outwardly regardless of their specific composition or use. The extra layers are an optional special-purpose inner spherical coat designed to enhance diagnositc X-ray or magnetic resonance or PET imaging and an optional thin outermost special-purpose coat.

Figure 4:
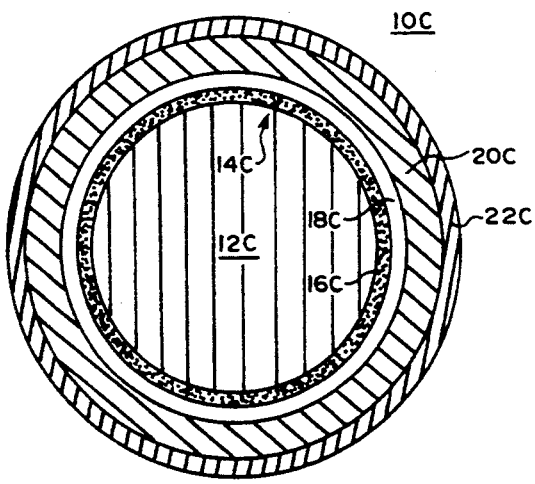
FIG. 4 is a sectional view of still another embodiment of multilayer radioactive microsphere.

The optional thin (less than 0.01 mm thick) outermost special-purpose coat is shown at 22C in FIG. 4 and at 24D in FIG. 5. This optional outer coat may be dc, rf, laser ablation or magnetron sputtered, ion-plated, ion-beam sputtered, or curvilinear or standard cathodic arc plasma deposited materials such as diamond, diamond-like carbon, titanium nitride, titanium carbonitride, titanium carbide, tantalum carbide, hafnium nitride, zirconium nitride, platinum, or tantalum. These coats individually produce additional desirable multilayer radiation-emitting microsphere physical characteristics such as increased hardness, scratch resistance, colors used for identification, reduced friction, increased tissue compatability, and increased corrosion resistance that enhance the basic spherical sputtered laminated multilayer radiation-emitting microsphere design of the present invention.

Optional thin outer multilayer radiation-emitting microsphere coats may be used to produce different seed identification colors to clearly label seeds of differing compositions or to differentiate seeds with low versus high activities, long versus short half-lives, or low versus high gamma energies. These layers must not only produce colors but they must also be tissue compatible and corrosion resistant, because they are the outermost layer of the multilayer radiation-emitting microsphere.

Diamond coated multilayer radiation-emitting microsphere's are less likely to be damaged by surgical instrumentation. Also, reduced friction of this surface coat makes the multilayer radiation-emitting microsphere of the present invention less likely to jam in an autofeeding tissue implantation gun. A thin layer of diamond (less than 0.001 mm) thick produced by reactive cathodic arc deposition from a carbon-containing gas is a preferred optional thin outer multilayer radiation-emitting microsphere coat of the present invention.

If necessary, to reduce porosity or remove crystallization of the coats of the finished product, or to improve adhesion between layers, after completion of coat, the multilayer radiation-emitting microsphere's may be annealed in a separate apparatus. In some embodiments, this may be done by heating close to the bulk metal melting temperature in a microsphere bouncing pan and thus result in a fine crystal structure typical of annealed materials.

The optional inner spherical uniform special purpose coats may be used to enhance imaging of the multilayer radiation-emitting microsphere by conventional radiographs, computed tomography or magnetic resonance imaging or other remote imaging arrangements. It may be a relatively thin (less than 0.01 mm thick) rf, magnetron, laser ablation or dc sputter-deposited, or ion-plated, or ion-beam self-sputtered, curvilinear cathodic arc plasma deposited or standard cathodic arc plasma deposited layer for diagnostic X-ray imaging enhancement or magnetic resonance imaging enhancement or positron emission imaging enhancement (PET) or single position emission computed topography (SPECT) for seed identification.

A coat such as gadolinium, erbium, terbium, thulium, cerium, cobalt fluoride, dysprosium oxide, dysprosium sulfide, neodymium fluoride, terbium oxide, samarium bromide, thulium oxide, etc. is chosen for the purpose of magnetic resonance imaging because of their properties of paramagnetism and high magnetic susceptibility as well as high-boiling point that reduces vacuum welding during coat deposition.

Elements or compounds that are suitable for the magnetic resonance imaging layer of the present invention include cerium (B.P. 3,468 C, magnetic susceptibility (ms) in 10-6 cgs ms+5,160.0), cobalt fluoride (B.P. 1,400 C, ms+9,490.0), dysprosium oxide (M.P. 2,340 C, ms+89,600.0), dysprosium sulfide (M.P. - - - , ms+95,200.0), erbium (B.P. 2,900 C, ms+44,300.0) gadolinium (B.P. 3,000 C, ms+75,000.0), manganese dichloride (B.P. 1,900 C, ms+14,300.0), neodymium fluoride (B.P. 2,300, ms+4,980.0), samarium bromide (B.P. 1,880, +5,337.0), terbium (B.P. 2,800 C, ms+146,000.0), terbium oxide (B.P. - - - , ms+78,340.0), thulium (B.P. 1,727 C, ms+25,000.0), thulium oxide (B.P. - - - ms+51,444.0).

Because these elements have sufficiently high boiling points to be effectively coated onto the multilayer radiation-emitting microsphere of the present invention, and because they have significantly different magnetic susceptibilities, it is possible to separately identify different multilayer radiation-emitting microsphere's coated with different magnetic resonance imaging imaging agents within the same tumor for purposes of tumor dose calculations. This is significant because, to take full advantage of the wide variety of multilayer radiation-emitting microsphere's of the present invention, it is advantageous to implant more than one type of multilayer radiation-emitting microsphere in one procedure into the same tumor.

To be discharged from a hospital, a patient with permanently-implanted radiation-emitting seeds must wait until the total activity of the seeds falls below a permissible level specified for that particular radionuclide. Using short-lived radionuclides, these radiation-emitting activity levels can be obtained within a reasonable number of days, thus avoiding excessively long hospitalization, while still delivering adequate tumor dose.

The central sphere or other coats may be formed of a material that is heatable by remotely radiated energy for hyperthermia and/or a magnetic material that enables force to be applied to the seed to move it around using externally radiated energy to avoid damage to tissue. For example, ferromagnetic materials may be used that are heated by induced radio frequency energy to the Curie temperature and have a Curie temperature appropriate for hyperthermia such as, for example, 50 degrees Centigrade. Moreover, a strongly magnetic material may cause movement of the seed by externally applied electromagnetic fields.

Substrate cores composed of a suitable ferromagnetic alloy or paramagnetic or ferroelectric compounds in the form of microspheres that have a sharp Curie transition in the range of 40 to 50 degrees Centigrade may be manufactured in situ by coating a starting seed with a ferromagnetic compound such as by sputtering, laser ablation or cathodic arc deposition using the appropriate target materials and/or reactive gases or by making the entire seed of the appropriate material. Elements suitable for Curie-transition-point substrate microspheres for use in the present invention include iron, cobalt, nickel, dysprosium and gadolinium. Other alloys can be formed to have the proper Curie point.

Elements and compounds are combined in optimal proportions to produce a final seed that has a sharp Curie transition point in the range of 42 degrees Centigrade to 50 degrees Centigrade. The compounds and elements may be alloyed in situ by sputtering from the appropriate shuttered targets. Differential shuttering of the targets permits control of the sputtering rate of each target, and permits precise control of the percentages and proportions of target materials alloyed onto the substrate microspheres. Similarly, the proportions can be easily controlled using laser ablation techinques, wherein a laser is used to vaporize one or several sputtered targets.

For example, the nickel series of alloys can be used to produce microspherical substrates with Curie transition points in the range of 42 to 50 degrees Centigrade. These include: Vanadium 4%+Nickel 96%; Molybdenum 6%+Nickel 94%; Chromium 8%+ Nickel 92%; Titanium 9%+Nickel 91%; Sb 7%+Nickel 93%; Silicon 8%+Nickel 92%; Aluminum 12%+Nickel 88%; Platinum 28%+Nickel 72%; Manganese 17%+Nickel 83%; Copper 29%+Nickel 71%.

Although the embodiments of FIGS. 1-5 show from three to five coats, a seed may be formed of a 0.20 mm diameter tantalum center, a 0.01 mm to 0.045 thick Ti (I-125) 2/TIN inner coat and a 0.05 mm thick titanium nitride outer coat. This structure is possible because the TiN serves as both a diffusion barrier and as a protective coat, thus removing the need for another diffusion barrier coat.

In use, the multilayer radioactive microspheres are surgically implanted, either permanently by placing them directly into the tissue, or temporarily by placing them in catheters, or removable tubes, etc. One surgical technique for implantation of multilayer radioactive microspheres includes selecting the half-life, energy, activity and field strength of the implant in accordance with the time of implantation, implanting the high energy microspheres and removing high energy microspheres after a time period long enough to destroy only neoplastic tissue and not long enough for the destruction of differentiated healthy cells in accordance with the intensity of the radiation. However, if the high energy microsphere has a relatively short half-life, it need not be removed and may be permanently implanted. Also, low-energy miscrospheres are not hazardous to others because the energy is almost completely absorbed within the patient. Thus, low-energy microspheres are usually permanently implanted, unless a high dose rate is desired. Even for temporary implants, low-energy implants are less hazardous to hospital personnel.

A plurality of low energy microspheres may be implanted at distances from each other in accordance with the intensity wherein only neoplastic tissue is destroyed by physically confining the major radiation dose to the neoplastic tissue by virtue of the physical characteristics of the microspheres. An auto-feeding implantation gun may be used.

In one form of treatment, between 30 and 300 low activity multilayer radioactive microspheres are implanted permanently into a human tumor at approximately 1 centimeter intervals throughout the volume wherein continuous-low-dose rate low energy irradiation is produced at less than 1.5 Gray per hour. In conjunction with the implant, minimum doses of 80 to 3,000 Gray to the tumor volume over the average lifetime of the multilayer radioactive microsphere may be delivered.

The idea of synchronizing cells prior to radiation therapy has been tried clinically by utilizing chemotherapy agents as cell synchronizing agents. For example, hydroxyurea has been tried as a cell synchronizing chemical agent prior to external beam irradiation in the treatment of cervical cancer and malignant glioblastomas of the brain. These trials have been only moderately successful or unsuccessful.

An "inverse dose-rate effect" has been described in which decreasing the dose rate of radiation delivery results in increased cell killing. This paradoxic effect has been explained by the fact that at certain dose rates, cells tend to progress through the cell cycle and become arrested in G-2 or G-2/S, a very radiosensitive phase of the cell cycle. Further continuous low-dose rate irradiation of these "arrested and radiosensitized" cells then results in very effective cell killing, far beyond that expected from the relatively low radiation doses delivered.

The actual dose-rates that produce this effect vary widely for different cell lines. The dose-rates that effectively produce a G-2 block for a given tumor type can be determined experimentally by culturing tumor cells and analyzing the cell-cycles using standard flow-cytometry techniques. It can also be determined by trial and error with a patient. It has been determined by one investigator that the minimum dose- rate necessary to stop cell division of HeLa cells was approximately 23 rad/hour, but it was approximately 270 rad/hour for V-79 cells - - - a ten-fold difference.

For these "optimum" dose rates that stopped cell division, all the cells were noted to progress through G-1 and S-phase, with a small delay in S-phase, followed by complete block in G-2 phase. HeLa cells showed a dramatic effect of redistribution of cells into sensitive phases of the cell cycle during exposure, which was reflected in the survival curves at low dose rate, and more cell killing per unit dose was observed at 37 rad/hour than at 74 rad/hour. Thus, at the optimal dose rate, cells tend to progress through the cell cycle and become arrested in G-2, a known radiosensitive phase of the cell cycle. While so arrested, they may be more efficiently killed by delivery of further radiation. At higher dose rates, cells are "frozen" in the phase of the cycle they are in at the start of irradiation. At lower-than-optimal dose rates, the cells escape the G-2 block and proceed to cycle and divide as usual during irradiation.

Each tumor-type has a characteristic "optimal-dose rate" that produces prolonged cell cycle ar rest in the radiosensitive G-2 phase. This "optimal-dose-rate" can be determined using standard cell culture and cell-cycle analytic techniques. Bedford and Mitchell noted that dose rates of 38 rads per hour for HeLa cells and 90 rads per hour for V-79 Chinese hamster cells essentially prevented cell division, but such continuous irradiation had no effect upon the progress of cells through G-1 or S-phase, but produced a G-2 delay and prevented cell division.

The multilayer radioactive microspheres disclosed in the present invention can be matched (by producing multilayer radioactive microspheres with specifically matched energies, half-lives, and activities) to a particular tumor to produce this "optimal-dose-rate" throughout the tumor target volume, and cause a prolonged block at G-2, and thus serve as a "radiosensitizer" if present during administration of a conventional course of external-beam irradiation. In other words, the multilayer radioactive microspheres disclosed in the present invention can be manufactured to "match" the radiobiology of a particular tumor and thus produce an "optimal" dose rate of continuous irradiation and thus serve as a "radiosensitizer" by blocking the cells within the tumor target volume in the G-2 phase of their cell cycles.

Percutaneous needle biopsy using either CT (computed tomography) or sonographic (ultrasound) guidance is a common procedure that has been developed over the past 15 years. In the early years of radiologically guided needle biopsy, most biopsies were performed using thin-caliber (21-gauge to 22 gauge) needles which provided a known wide margin of safety. The use of thin-gauge needles to perform biopsies is historically associated with the lowest risk of bleeding and tissue trauma. Even overlying loops of stomach or small intestine are not a contraindication to needle biopsy if small-caliber thin-gauge needles are used. The most common human body sites in which radiologically guided biopsy has been performed include the liver, pancreas, retroperitoneum, adrenal gland, pelvis, chest, bone, extremity, and neck.

Because of its small size, (usually less than 0.40 mm diameter) the multilayer radioactive microspheres of the present invention can be easily and safely implanted into almost any body site using a small-caliber thin-gauge (21G to 22G) interstitial implantation needle using the same techniques initially developed to perform percutaneous needle biopsies under CT and sonographic guidance. Additionally, multilayer radioactive microspheres of the present invention can be implanted using MRI guidance (magnetic resonance imaging).

The relatively recent use of computers to digitize the relative spatial coordinates of human body organs derived from CT, MRI, and PET (positron emission tomography) scans and produce three-dimensional images (Scandiplan, Scanditronix Inc, Uppsula, Sweden) could be utilized to stereotactically implant multilayer radioactive microspheres into specific body sites using such digitized data to guide the interstitial needle to specific cartesian or polar body coordinates in relation to a reference system. While stereotactic frames have been used extensively in the past to perform neurosurgical procedures, stereotactic techniques have not been used in the past to implant radioactive seeds into body sites other than the brain, pituitary, or skull base. However, such stereotactic techniques may be applied to implant multilayer radioactive microspheres into any body site in a "stereotactic body-implantation" system using either a "stereotactic frame" or a "robotic-arm".

Stereotactic brain surgery is a technique for guiding the tip of a probe into the brain through a hole drilled in the skull without having direct visualization of the surgical site. Such techniques have been developed and applied in the field of neurosurgery. Stereotactic surgical frames have been coupled with CT scanners since any point identifiable on a CT scan can be related to stereotactic coordinates, allowing stereotactic guidance of surgical instruments for biopsy or neurosurgical procedures. There are numerous geometrical systems upon which stereotactic frame coordinates could be based.

The four main types of frames developed to date include: (1) polar coordinate; (2) arc-radius; (3) focal point; (4) phantom target. A typical polar coordinate stereotactic system requires that a trajectory is described in polar coordinates relative to an entry point. Arc radius frames employ a probe in a semicircular arc which is introduced orthogonal to a tangent along the arc. Phantom or "dummy" devices may use any coordinate system to determine the angles and probe lengths of a stereotactic device mechanically rather than trigonometrically. This approach may be used to implant microspheres at the selected locations.

A new teqhnique in which a commercially available robot (Unimation Puma 200 robot) performs a "robotic stereotactic" brain biopsy is known. Spatial information determined by CT scanning is tied into a base frame used to immobilize the patient, and this information is translated into robotic spatial coordinates that are used to direct the robotic arm and biopsy needle to the proper location.

Robotic stereotactic techniques may be applied to implant multilayer radioactive microspheres into any body site in a "robotic body-implantation" system without relying upon a "stereotactic-frame". The primary use of multilayer radioactive microspheres and related products is the safe delivery of high tumoricidal radiation doses to human tumors that are two to five times higher than those achievable by conventional external-beam radiation therapy. A second use of multilayer radioactive microspheres is the clinical use of multilayer radioactive microspheres as radiation sensitizers to enhance the tumor-effect of a conventional course of external-beam radiation therapy.

Generally, the primary use of multi layer radioactive microspheres is to permit safe delivery of tumoricidal doses of radiation that are two to five times higher than that deliverable by external means. In the first application of multilayer radioactive microspheres, the total dose delivered is the critical factor, and this dose must be completely tumoricidal. The second use of multilayer radioactive microspheres of the present invention includes the use of multilayer radioactive microspheres radiation as a radiation sensitizer in the sense that continuous low dose rate irradiation produced by multilayer radioactive microspheres optimally synchronizes tumors and causes cells to remain blocked in the radiosensitive portion of their cell cycles. In this secondary application, the dose of radiation delivered by the seed is not critical, and in most cases it may not even be substantially tumoricidal. However, the tumor volume dose rate is critical, and it must be high enough to hold cells in the G-2 block 24 hours per day, but it must be low enough to permit cells to progress through their cell cycles until they come to G-2. An excessively high dose rate would result in immobilization of all cells at their particular points within their cell cycles and is an undesirable effect.

Because of their small diameters, the multilayer radioactive microspheres of the present invention may be implanted using thin-caliber 21-Gauge or 22-Gauge needles using either CT, MRI, or sonographic guidance techniques originally developed in the field of radiology to perform percutaneous needle biopsies.

Stereotactic techniques developed and applied to the field of neurosurgery are now applied to all body sites to permit stereotactic implantation of multilayer radioactive microspheres of the present invention into any body site. A stereotactic body frame is introduced for implantation of multilayer radioactive microspheres using CT or MRI guidance.

Robotic techniques developed and applied to the field of neurosurgery are now applied to all body sites to permit robotic implantation of multilayer radioactive microspheres of the present invention into any body site. A robotic multilayer radioactive microspheres implantation system is introduced for implantation of multilayer radioactive microspheres using CT or MRI guidance coupled to a robotic arm without a stereotactic frame.

Multilayer radioactive microspheres implanted into human tumor tissues whether permanently or temporarily, are used to deliver tumoricidal radiation doses that are two to five times higher than those achievable using conventional external-beam radiation therapy techniques. In some cases, a standard course of radiation therapy may be delivered before seed implantation (4,000 cGy to 7,000 cGy in four to eight weeks) to achieve some tumor shrinkage prior to multilayer radioactive microsphere implantation. The combination of external-beam radiation therapy delivered either before or after seed implantation generally improves the homogeneity of the radiation within the target volume over that obtained using radioactive seeds alone.

External beam radiation therapy given before or after seed implantation is frequently used to irradiate occult microscopic metastases in regional nodes around a primary tumor and beyond the tumor target volume treated by the radioactive (multilayer radioactive microspheres) seed implant. For example, the treatment of a poorly-differentiated adenocarcinoma of the prostate could involve irradiation of the pelvic lymph nodes followed by radioactive seed (multilayer radioactive microspheres) implantation of the primary tumor mass.

This approach is effective because it is known that 5,000 cGy will control 90 percent of occult microscopic metastases in regional lymph nodes, but much higher doses of 16,000 cGy are necessary to achieve 90 percent control of a primary solid tumor mass in the prostate. Thus, sterilization of occult regional nodal metastases is accomplished by administration of external-beam radiation therapy, and sterilization of the primary tumor mass is accomplished by delivery of a high localized radiation dose using multilayer radioactive microspheres radioactive seed implantation of the tumor mass.

The course of external beam radiation therapy is then followed by implantation of multilayer radioactive microspheres radioactive seeds to safely deliver a high tumoricidal radiation dose to the target volume encompassing the tumor (8,000 cGy to 300,000 cGy). Alternatively, seed implantation alone can be used to treat a human tumor without the addition of external beam radiation therapy. Thus, tumoricidal radiation doses are achieved using either implantation of multilayer radioactive microspheres alone, or by administration of external beam radiation therapy before or after radioactive seed (multilayer radioactive microspheres) implantation. The critical point is that the primary goal of treatment using multilayer radioactive microspheres implantation with or without the addition of external beam radiation therapy is to achieve safe delivery of high tumoricidal radiation doses that are effective in controlling human tumors.

The primary types of endocurietherapy applications utilizing multilayer radioactive microspheres include: (1) permanent implantation of multilayer radioactive microspheres into human tumor tissues in locations such as the brain, pituitary, skull base, parotid, base of tongue, thyroid, tonsil, pharyngeal wall, neck nodes, mediastinum, spinal cord, lung, chest wall, axilla, brachial plexus, pleura, pancreas, liver, stomach, adrenals, abdominal wall, prostate, bladder, sacral tumors (chordoma), pelvic tumors (cervix, endometrium, prostate, bladder, rectum, anus, ovary, sarcomas), extremity tumors, et cetera, and implantation of multilayer radioactive microspheres surgical fabric in a resected tumor bed; (2) temporary interstitial needle or catheter implantation of multilayer radioactive microspheres (via removable tubes or sutures threaded through the needles, or via removable multilayered radioactive needles) into human tumor tissues located in accessible body sites such as the brain, floor of the mouth, anterior tongue, tonsil, face, scalp, skin surface, buccal mucosa, lip, extremities, neck nodes, chest wall, mediastinum, lung, bladder, cervix, endometrium, vagina, anus, rectum; (3) temporary intracavitary application of encapsulated multilayer radioactive microspheres or coated intracavitary cylinders or wires into accessible body cavities such as the bladder, rectum, vagina, cervix, endometrium, esophagus, trachea, bronchus, nose, nasopharynx et cetera; and (4) temporary application of multilayered radioactive plaques to accessible sites such as the hard palate, extremities, and globe of the eye.

In the second application, the dose delivered by the multilayer radioactive microspheres may be much less than tumoricidal. The goal of multilayer radioactive microspheres implantation in this case is not to directly kill the tumor by radiation emitted by the multilayer radioactive microspheres. Instead, the multilayer radioactive microspheres functioning as a radiation sensitizer is used to deliver continuous low dose rate radiation at a dose rate that serves to synchronize and block tumor cell populations in the most radio-sensitive phases of their cell cycles throughout a six to eight-week course of conventional external-beam radiation therapy.

This therapy accomplished by delivering radiation to the tumor tissues continuously 24-hours per day at a rate that permits cells to cycle yet causes the cell cycle to be blocked in the radio-sensitive part of the cell cycle ($G_{2M}$, late G2, or $G_2/S$). The continuous radiation dose rate must be sufficiently high to prevent cell escape from the block and thus hold them at the block, but it must be sufficiently low to permit cells to proceed through their cell cycles without complete cycle inhibition. If the cells are blocked and held in the most radio-sensitive phases of their cell cycles, then the daily administration of conventional fractionated external-beam radiotherapy (given daily, 5 days/week, 1 fraction/day, 150–225 cGy/fraction, 100–400 cGy/minute dose rate) will be much more efficient in killing tumor cells that might otherwise be in radioresistant phases (S-phase, $G_1$) at the time of administration of external-beam radiation (given in two-minutes every 24-hours).

Because of the great flexibility of the manufacturing process for production of multilayer radioactive microspheres of the present invention and the ability to produce multilayer radioactive microspheres containing over 220 different radionuclides, the half-life, energy, and activity of the multilayer radioactive microspheres can be precisely matched to the type and size of tumor being treated to deliver continuous low dose rate radiation at the proper rate to produce a sustained G-2 block.

Normally, the majority of cells in a tumor population are in radioresistant phases (quiescent somatic, resting phases) during the majority of the time, and only a small percentage of the population resides in radiosensitive phases. Thus, daily administration of fractionated external-beam radiation therapy results in irradiation of tumors composed mainly of cells that are radioresistant. The dose of conventional fractionated radiation required to control a radioresistant tumor cell population is relatively high (8,000 to 12,000 centi-Gray), and this dose is approximately 40 percent to 60 percent higher than what the surrounding normal tissues can tolerate.

For this reason, it is only possible to control approximately 30 percent of solid tumors (adenocarcinomas, squamous cell carcinomas, sarcomas, melanomas) treated by a conventional modern course of external-beam radiation therapy. This poor therapeutic ratio characteristic of conventional fractionated external-beam radiation therapy could be dramatically improved by modifying the radiosensitivity of the tumors under treatment. If tumors composed mainly of radiosensitive cells are irradiated in a conventional fashion, then the required tumor dose should be much lower. In fact, cell culture studies have indicated that cells blocked in G-2 phase can be killed by approximately half the dose of radiation normally required.

The amount of radiation that can be safely delivered by external means is limited by the surrounding normal tissues to a maximum of approximately 7,000 centi-Gray (cCy). This dose applied to a 5 centimenter diameter tumor composed largely of radioresistant cells results in approximately a 30 percent local control rate.

However, the same dose applied to a tumor composed largely of radiosensitive cells should result in a much higher local control rate. The tumor can be converted from one composed of radioresistant cells to one composed of radiosensitive cells by the permanent implantation of one or several multilayer radioactive microspheres which deliver continuous low dose rate irradiation at the proper rate to cause a sustained G-2 cell cycle block. Consequently, prior to administration of a conventional course of external-beam radiation therapy, implantation of one or several multilayer radioactive microspheres should dramatically increase the cure rate. This can be accomplished without an increased complication rate, because a relatively low total dose of radiation is delivered by the multilayer radioactive microspheres, and this dose is sharply localized due to the physical characteristics of the radionuclide.

If tumors treated by external-beam radiation therapy are first "radiosensitized" by implantation of one or several multilayer radioactive microspheres, then the seed implantation procedure may safely performed in a wide variety of human body sites without risk of complication caused by seed implantation. Because of the seed design, multilayer radioactive microspheres may be implanted into almost any body site using thin-caliber (21-gauge to 22-gauge) needles. Multilayer radioactive microspheres implantation performed using these thin gauge needles permits safe implantation without significant risk of bleeding or tissue trauma, and overlying loops of stomach or small intestine are usually not a contraindication.

In one system of therapy, a CT scanning system or other imaging system such as MRI (magnetic resonance imaging) is used to obtain images. A flat table is designed to attach over the standard curved CT scanner patient table. This table serves as a reference base for a stereotactic coordinate system. The table has built into the side rails X-ray markers that may be seen on the CT scout film, and allow determination of distance from a reference point on the Z-axis of the coordinate system.

The patient is immobilized on this table by means of straps or pins. A CT scan of the body is taken with images taken 0.20 to 2.0 centimeters apart. The area to be implanted with multilayer radioactive microspheres is determined by a physician, and a scan image (for example, image 5, $Z = -90$ millimeters) corresponding to the desired point of implantation is chosen. A semicircular arc composed of a material that is relatively transparent to X-ray images (titanium, or carbon filament) is then attached to the reference table at the level corresponding to the chosen scan image. A stereotactic instrument holder is attached to the arc or aiming bow.

The 21-gauge or 22-gauge implantation needle is inserted into the instrument holder. Stereotactic coordinates of the biopsy point are set on the aiming bow (arc) and instrument holder to direct the needle to the proper point, and adjustment are locked. A table slides the patient to the proper scan point, and using repeated CT scans through the chosen Z-coordinate slice, the needle is inserted into the target point within the patient under CT-guidance. The position of the needle tip is verified with a final CT scan when it is positioned in the center of the tumor to be implanted. The stylet is removed from the 21-G or 22-G implantation needle, and the radioactive multilayer radioactive microspheres is placed into the hollow needle and implanted into the tissue by replacing the needle stylet.

In another such system, the flat table is designed to attach over the standard curved CT scanner patient table. This table serves as a reference base for the robotic coordinate system. The table has built into the side rails "Z-shaped" X-ray markers that may be seen on the CT scout film, and allow determination of distance from a reference point on the Z-axis of the coordinate system. A commercially-available robot arm containing six joints of rotation and a relative accuracy of 0.05 millimeters is attached to a gantry linked to the table base coordinate system. The robotic arm is modified in that the arm is constructed only of materials known not to interfere with CT scanning X-rays (titanium, carbon filaments).

The patient is immobilized on this table by means of straps or pins. A CT scan of the body is taken with images taken 0.20 to 2.0 centimeters apart. The area to be implanted with multilayer radioactive microspheres is determined by a physician, and a scan image (for example, image 5, $Z = -90$ millimeters) corresponding to the desired point of implantation is chosen. Spatial target coordinates are determined by selecting the target point on the chosen CT-slice, and these are translated into base-reference system coordinates and robotic arm coordinates. The robotic arm aims a spring-loaded needle injector (which is capable of instantaneously injecting a 21-gauge or 22-gauge thin-diameter needle through human tissues to any desired distance at 1 to 5 millimeters increments to a maximum depth of 40 centimeters) at the target point.

The base table slides patient to proper scan point, and the needle injector is fired, placing the needle tip instantaneously at the desired target point within the body. The correct position of the needle tip is verified with a final CT scan when it is positioned in the center of the tumor to be implanted. The stylet is removed from the 21-G or 22-G implantation needle, and the radioactive multilayer radioactive microspheres is mechanically injected into the hollow needle and implanted into the tissue by mechanically pushing the stylet through the needle behind the seed.

EXAMPLES

The following hypothetical nonlimited examples illustrate the invention:

Example 1

A patient has a malignant adenocarcinoma of the head of the pancreas which is inoperable because of its proximity to the celiac plexus and porta hepatis and measures 3.5 in length×2.0 centimeters in diameter. The patient receives external-beam radiation therapy, but the maximum deliverable dose is limited to 6,000 centi-Gray because of potential toxicity to the surrounding normal tissues. This dose of 60 Gray delivered over 6 weeks, 200 centiGray/fraction, 5 days/week is known to be inadequate to result in lasting local control of this radioresistant tumor. His chances for local tumor control are now less than 30 percent.

The tumor is needle biopsied, and cell culture of the tumor is accomplished, and the cells are exposed to various dose rates of continuous irradiation. It is determined using flow cytometry techniques that a sustained G-2 block occurs if the cells receive continuous irradiation at a rate of 25 to 50 centi-Gray per hour. Computerized radiation dosimetry indicates that two 1–125 seeds containing 25 mCi each implanted 1.7 centimeters apart produce a dose of 35 centi-Gray/hour to a tumor target volume measuring 3.5 cm×2.0 cm.

Two spherical multilayer radioactive microspheres 0.30 millimeters in diameter and containing 25 mCi of radioactive I-125 as described above are obtained. The patient is taken to the CT scanner and placed on the special flat base table connected to the robot gantry. Scans are taken, the target points are chosen, and coordinates are calculated and translated into robot arm coordinates. The robot arm fires the spring loaded 21-G needle to the correct location within the pancreatic tumor, and the correct position is verified with CT scan. The first I-125 multilayer radioactive microspheres is injected and permanently implanted. Another 25 mCi multilayer radioactive microspheres is implanted 1.7 centimeters from the first using the same technique.

Repeat tumor biopsy is performed 5 days later, and using flow cytometry, it is found that more than 90 percent of the tumor cells are blocked at G-2. Now the radiation dose of 6,000 cGy will be twice as effective because the tumor is composed mainly of radiosensitive tumor cells blocked in G-2. The 6,000 centi-Gray will be biologically equivalent to a dose of 12,000 centi-Gray, and chances for tumor control are increased to over 90 percent. The radiation dose delivered by the I-125 seeds adds to the tumoricidal effect, in addition to producing a sustained G-2 block that results in radiosensitization to external-beam irradiation.

Example 2

A female patient with a malignant fibrous histiocytoma (MFH, soft tissue sarcoma) located in the presacral hollow and measuring 10 centimeters in diameter is determined to have an inoperable tumor due to bony invasion of the first sacral vertebral body. She is to receive a course of external-beam radiation therapy, but the maximum dose deliverable is limited to 7,000 centi-Gray in 7 weeks due to the poor tolerance of surrounding normal tissues including small bowel and colon. Her chances for local tumor control are less than 30 percent.

Cell culture of the tumor is successful, and cells are exposed to low dose rate irradiation. Flow cytometry studies indicate that radiation dose rates of 150 centi-Gray/hour are required to produce a sustained G-2 block, and thus render the sarcoma cells radiosensitive. Because of the high dose rates required to produce a G-2 block, the radioactive seed must have low energy to avoid irradiation adjacent structures.

Palladium-112 is chosen as the radionuclide with an energy of 18.5 KeV and half-life of 21.0 hours. Computerized radiation dosimetry indicates that ten seeds should optimally be implanted throughout the tumor volume. Ten spherical multilayer radioactive microspheres containing the required amount of Pd-112 and measuring less than 0.30 millimeters in diameter are manufactured according to the present disclosure.

The patient is taken to the CT scanner and the robotic arm is used to implant ten Pd-112 MRM's via a 21-G needle using CT guidance for verification. Repeat biopsy and cell culture with flow cytometry analysis indicates that more than 90 percent of cells are in G-2 block, and external-beam radiation therapy is initiated. The 7,000 cGy dose will be biologically equivalent to approximately 14,000 cGy due to radiosensitization and G-2 block produced by the multilayer radioactive microspheres. Tumor control probability is increased to over 90 percent. Because of the short half-life of the radionuclide, the robotic multilayer radioactive microspheres implantation procedure is repeated twice a week during the patient's external-beam radiation therapy (seven week course).

In FIG. 6, there is shown an intracavitary radiation-emitting capsule 30 having a plurality of radiation emitting microspheres 34A–34G, a stainless steel tube 36 and an end weld 38. The end weld 38 seals the tube 36 which contains the microspheres 34A–34G. The microspheres 34A–34G are of the type described in connection with FIGS. 1–5 and are selected for the therapeutic treatment desired. While only 7 are shown in FIG. 6, a larger number are normally used and there may be as many as 40 contained in a cylindrical tube that is 2.0 centimeters long and 1 millimeter in diameter.

While microspheres are shown in FIG. 6 as inserts to the intracavitary implant 30, other sizes and shapes may be used such as cylindrical bars or other geometric shaped radiating units. However, standard sizes manufactured by the electron bonding processes in quantities are desirable because of their economy and the ability to manufacture them with different radiation characteristics for flexibility of treatment. Moreover different shapes and sizes of containers may be used and the walls, instead of being of only one material, may include different materials or added materials to provide different amounts of shielding. For example a square tube may contain square radiating elements and include shielding and elements of different radiating intensities and characteristics.

A wide variety of radionuclides with energies varying from very low to very high can be incorporated into composite intracavitary sources by sealing mulitple multilayer radioactive microspheres of one or several types into an appropriate container. Use of low energy intracavitary sources composed of low energy multilayer radioactive microspheres allows selective shielding of adjacent vital structures such as rectum and bladder using relatively thin high atomic weight foils placed over the intracavitary sources. Morever, a 1 millimeter diameter solid intracavitary source and a solid needle source can be manufactured by coating the rod or needle substrate with a radioactive coat, diffusion barrier coat and protective coat.

The intracavitary sources of the present invention eliminate the need for dilating openings because of their small size. For example: (1) the cervial canal or endocervial canal need not be dilated because the intracavitary multilayer radioactive microspheres or wires have an outside diameter not exceeding 1 millimeter and cervial applicator has an outside diameter of only 2 millimeters which can be easily inserted into the uterus without cervical dilitation; (2) the diameter of the intracavitary multilayer radioactive microsphere applicator is less than that of a uterine sound; (3) an intraoperative brain tumor applicator has a diameter of only two millimeters; and (4) the 1 millimeter source can be placed in a balloon catheter and easily slipped through the urethra for intracavitary bladder tumor irradiation.

The intracavitary multilayer radioactive microspheres can be easily shielded, making possible effective in vivo shielding of critical normal tissues at risk for radiation toxicity such as the bladder and rectum adjacent to the cervix. Thus, a radiation dose distribution can be designed that suits the individual patient's anatomy. The intracavitary multilayer radioactive sources of the present invention are suitable for treatment of cervix and uterine cancer, bladder cancers, esophageal cancers, biliary duct cancers, brain tumors, and nasopharyngeal cancers.

In FIG. 7, there is shown another embodiment 42 of multilayer radiation emitting implant formed as a solid wire-like cylinder, without void spaces, and having a plurality of layers similar to the microspheres described in connection with FIGS. 1-5.

In the preferred embodiment, the radiation emitting implant 42 is substantially 10 to 20 centimeters long and has an outer diameter of approximately 0.15 to 0.40 millimeters in diameter. The intensity of its emission may vary along its length and may vary in intensity and half-life. Moreover, radioactive shielding may be coated on part of it. It has a sufficiently high yield point to permit bending to that it can be shaped in coordination with its radiation characteristics along its length to permit planned dosage in three dimensions through a tumor.

The wire-like implant 42 includes a central cylinder 44 and a plurality of tubular layers 45 concentric with the central cylinder 44 and bonded to each other. The central cylinder serves as a substrate upon which other other layers, at least one of is a radiation emitter, are coated. The type of radiation emitting material is selected for appropriate intensity, to be beta partice or gamma ray emissive and for a predetermined half-life.

In the preferred embodiment, the central cylinder is 0.10 millimeter in diameter and made of tantalum and the layers are a holmium I-125 cylindrical tube 46, a hafnium nitride (HfN) cylindrical tube 48 and a titanium cylindrical tube 50, in the order named from the inside outwardly. The tube 46 is radiation emitting and may be applied at different thicknesses along the length of a wire-like implant by any of several methods to be described hereinunder. However, in the preferred embodiment, it is approximately 0.01 to 0.045 millimeters thick. The tube 48 is a diffusion barrier and substantially 0.005 to 0.05 millimeters in thickness and the tube 50 is a protective layer and is approximately 0.05 millimeter thick.

The multilayer radioactive wires of the present invention are used primarily for temporary removable implants. Instead of inserting bits of iridium wire into nylon tubing for afterloading (Rad/Irid Inc, Capitol Heights, Md.), a variety of different radionuclides incorporated into multilayered radioactive wires may be inserted into nylon or tissue compatible polyethylene tubing (American V. Mueller, American ttospital Supply Corporation) for temporary removable interstitial implants. These types of temporary removable implants are useful for implantation of tumors at accessible sites where the tubes penetrate the skin surface. Furthermore, a cut multilayer wire 1 millimeter in outer diameter may serve as an intracavitary source, or as a removable radioactive needle.

Temporary removable iridium-192 nylon ribbon implants have been used for treatment of head, neck, lung, vaginal, cervical, vulvar cancers, prostrate, breast, soft-tissue satcomas and skin cancers. Radioactive wires placed in after loading tubing may also be used for intracavitary treatment of esophageal cancer and biliary duct cancers (Klatskin's tumor) or bronchial lung cancers.

In FIGS. 8 and 9, there are shown a side sectional view and top sectional view of a ribbon-like radiation emissive implant 54 having a flexible ribbon-like connecting member 56 and a plurality of microsphere radiation emitters 58A-58C. The ribbon-like connecting member 56 acts as a rigid spacer between radiation emitters 58A-58C and allows multiple emitters to be implanted at once with a conventional thin gauge hollow needle by pushing the ribbon-like implant 54 out of the conventional tissue-embedded needle with a stylet while withdrawing the needle. The preferred rigid spacer material is metal with a diamond coat.

In the preferred embodiment, the ribbon and the ribbon-emitters 58A-58C may be implanted with a very thin 21 or 22-gauge needle. Although three radiation emitters are shown in FIG. 8, the ribbon-like implant 54 may be of any length and may contain any number of radiation emitters and any variety of different types of radiation emitters.

The ribbon-like implant 54 connects radioactive members internally by means of a thin metal ribbon or wire, rather than by an external suture, reducing the overall diameter. The ribbon-like connecting members are made rigid by locating lengths of tissue-compatible material over the connecting member between radiation emitters or by coating diamond-like carbon, or a low-atomic weight metal such as titanium or metal compound such as titanium nitride or zirocnium carbide over the connecting member between emitters using sputtering or plasma deposition. This rigid structure may be pushed into tissues from the proximal rather than distal end while simultaneously withdrawing the interstitial needle or may be implanted rapidly using automatic implantation devices described hereinafter.

In the preferred embodiment, the connecting member 56 is a 0.01 millimeter ribbon, substantially square or a 0.01 millimeter wire made of tungsten and the microspherical emitters contain, as shown in connection with emitter 58B an inner sphere 60 welded to the connector 56.

In this embodiment, the central sphere is 0.10 millimeters in diameter and made of tantalum and the layers are a holmium I-125 sphere 62, a hafnium nitride sphere 64 and a titanium sphere 66, in the order named from the inside outwardly. The sphere 62 is radiation emitting and methods to be described hereinunder. In the preferred embodiment, it is approximately 0.01 to 0.045 millimeters thick. The sphere 64 is a diffusion barrier and substantially 0.005 to 0.05 millimeters in a thickness and the sphere 66 is a protective layer and is approximately 0.05 millimeters thick.

The radiation emitters 58A–58C are optimized for individual tumor types so that permanent implants which deliver continuous low dose-rate irradiation over less than 130 days, may be used for slowly growing tumors such as prostate cancers, but because they may be less suitable for rapidly growing tumors such as glioblastomas, other shorter-lived emitters can be manufactured as needed by simply changing deposition parameters as discussed hereinafter. The ribbon-emitters are used mainly for permanent implants and the wire-emitters are used primarily for temporary-removable implants.

In FIGS. 10 and 11, there are shown a plan and a sectional view of a curved circular optical plaque 70 for applying radiation to the eye having a central radioactive layer 76, two outer steel or titanium supports 72A and 72B on either side of the radioactive layer 76, separated from the radioactive layer 76 by a corresponding two diffusion layers 78A and 78B. On the outside may be tissue compatible, anti-corrosive additional layers 80 and 82, if necessary. The layers form a section of a sphere with circumferentially spaced suture holes 74A–74H through it that provides a concave socket for applying a therapeutic dose of radiation inwardly to the eye.

To fit against the eye, the socket has a radius of curvature between 1.40 to 1.10 centimeters and the socket is formed in layers with no voids. The radioactive layer is low energy gamma emitter or beta emitter and may be a titanium-44 layer, an Sm-145, Sin-151, Tin-171 or I-125 layer having a thickness of about 0.01 to 0.045 millimeters. Titanium-44 provides 68–78 kiloelectron volts (KeV) of radiation a half life of 47 years. The cord length from edge to edge (diameter of plan view) is between 8 millimeters to 22 millimeters.

In FIG. 12, there is shown a plan view of another embodiment of optical plaque 70A similar in construction to the plaque of 70 except that one portion at 71 is cut away so as to fit close to the lens to avoid damage thereto. Generally, this type of optical plaque will have a cord diameter of between 20 to 22 milimeters. Similarly, FIG. 13 shows an embodiment having an arc shaped cut away compartment at 71A to provide space around the optic nerve so as to avoid damage thereto. This embodiment may range in size between 8 millimeters to 22 millimeters in cord size.

Similar sized plaques are shown in the embodiment 70C in FIG. 14 with a larger portion cut away for convenient fitting and three other embodiments 70D, 70E, and 70F are shown in FIGS. 15, 16 and 17 respectfully, all of which have multiple parts. The embodiment 70D of FIG. 15 is generally an 8 millimeter embodiment and is formed in two section divided along a hemispheric line whereas the embodiments 16 and 17 are formed in three sections having a central section and two end sections, with the embodiment 7F including an optic nerve cut away in one of the sections.

Other variations are possible and are designed to fit closely adjacent to the cancerous tissue with minimum overlapping that might unnecessarily irradiate healthy tissue. All of these embodiments are intended to provide a high radiation level such as 10,000 centi-Gray encompassing the cancerous tissue near the capular wall and retina with rapid attenuation so that a short distance out the energy level falls below 3,000 centi-Gray which is tolerable to the retina and optic nerve. Generally that drop occurs at a 30 percent isodose line.

Figure 18:
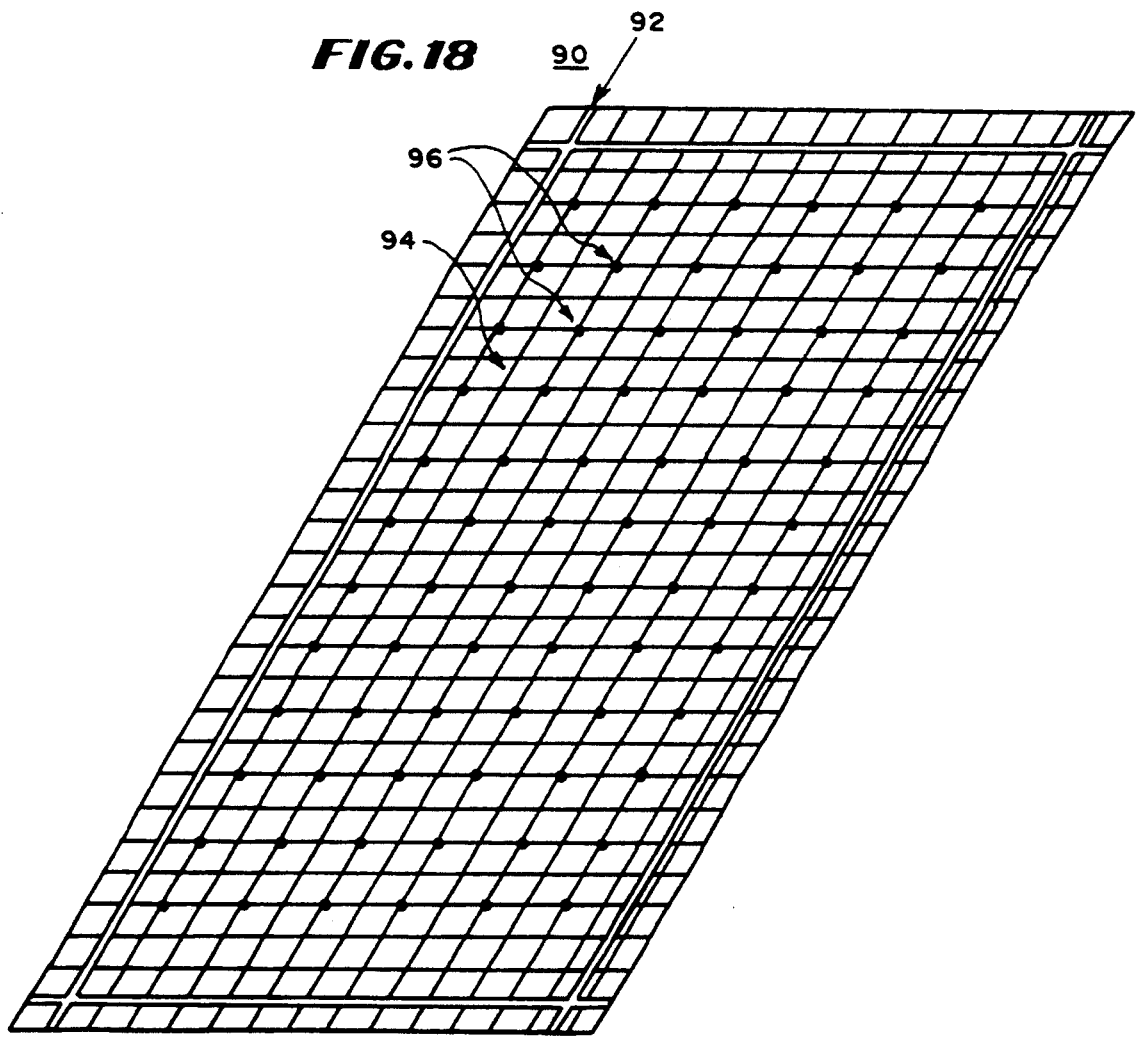
FIG. 18 is a plan view of a fabric-type embodiment of the invention.

In FIG. 18, there is shown a surgical radiation-emitting fabric 90 having a border strip 92 of X-ray opaque fiber, a fabric base 94 of cellulose fibers, and a plurality of radiation emitters 96 spaced throughout the fabric base 94. The radiation emitters 96 have basic structure of the microspheres of FIGS. 1–5 extending from it.

One embodiment of the fabric of this invention self-adheres to the tissues over which it is placed. The fabric may be either tissue-absorbable or non-tissue absorbable and may contain multiple multilayered radioactive microspheres. This construction allows rapid surgical implantation of multiple seeds without need of interstitial needles or a seed gun. The radiation emitters 96 may be spaced at 1.0 to 2.5 centimeter intervals embeded into a tissue compatible fabric. This fabric may be sewn intraoperatively into the tumor bed, or in the case of brain tumors, the fabric is simply laid over the area to be treated. It self-adheres to the tissues over which it is placed.

Two types of fabric multilayer radioactive microspheres are produced—tissue-absorbable fabric and non-tissue absorbable fabric. The tissue-absorbable fabric is also hemostatic and is suitable for intraoperative permanent implantation of the surgical bed in the chest, abdomen, extremity, or brain. Since the multilayer radioactive microsphere surgical fabric is hemostatic, it sticks to the tissues upon which is applied and need not be sutured.

However, it may be sutured in for additional immobilization if desired. The fabric eventually dissolves after several months, and tissue fibrosis caused by local seed irradiation holds the seeds in place. The tissue half-life of the fabric is made to match the radioactive half-life of the radioactive seeds. The non-tissue absorbable multilayer radioactive microsphere surgical fabric may be used in accessible body cavities.

In use, a non-tissue absorbable tissue-compatible fabric containing multilayer radioactive microspheres is placed into a cavity being treated. Either gauze packing or suture can be used to immobilize this temporary removable fabric multilayer radioactive microsphere. After an adequate treatment time, the fabric multilayer radioactive microsphere is removed. Because the fabric multilayer radioactive microsphere incorporates the entire wide range of radionuclides used in single multilayer radioactive microsphere, a great flexibility in treatment is provided. Using low energy multilayer radioactive microsphere surgical fabric, the patient may be discharged home with the low energy temporary removable implant in place and return at a later date for implant removal.

Tumors are detected either visually or through the use of imaging devices such as CAT, MR, PET or the like. A determination is made as to whether permanent implants or temporary multilayer radioactive implants should be used generally based on location of the tumor. A determination is then made concerning the use of temporary or permanent multilayer radioactive appliances. This determination is principally based on the location of the tissue.

Temporary implants are inserted for the required amount of time or permanent implants of selected half-lifes and energy levels are implanted for treatment. Scanning may be utilized both to aid in the proper implanting location or to monitor what has been implanted already.

To utilize temporary implants, generally needles formed from the multilayer wires, plaques such as ocular plaques or radioactive wires are inserted in accessible sites. For example, the very thin needles formed as wires and cut to size may be inserted at spaced locations through the epidermal layer or mucus membranes into the tumor. The energy of the temporary multilayer radioactive implants may be relatively high and the half-lives relatively long because of the temporary implantation.

In the case of needles, the needles may be inserted directly through the skin spaced apart from each other to achieve an appropriate energy absorbed by the tissue. This may require either lower energy needles near the center of the tumor and higher energy extending outwardly where the additive effect of the radiation is lower and need for radiation higher or a closer spacing of the needles near the outside of the tumor. Placement of the needles may be controlled by sonograms and a computer to make the appropriate configuration.

With a wire, a relatively small needle may be used because of the thinness and compactness of the wire or ribbon and a pattern may be sewn under the control of a imaging device and computer to apply the optimum field. To aid in the versitality of this approach, the needles may have higher energy radiation at the outer ends of the needle and lower in the center to aid in applying the correct concentration or where the wire is to be threaded, a controlled variation in energy may be created. The needle used to thread wire through a tumor or ribbon through a tumor may be as small in diameter as 21 or 22 gauge to permit ready insertion through tissues.

Relatively small intracavitary containers may be used to implant temporarily radioactive spheres in a safe manner without excessive dilation of body parts. These may be inserted in a conventional manner except that reduced dilation is required. Such intracavitary containers may be inserted and later removed from the bladder, cervix and the like.

Fabric may be used to quickly supply a contoured radiation over wide areas such as the chest. It is laid over the entire area. Stiff ribbon may be used to supply microspheres quickly through a tumor.

Permanent multilayer radioactive implants with low half-1 ires or low energy are permanently implanted. Generally, microspheres are injected for this purpose and in some embodiments, may be injected percutaneously through the mucus membrane or the skin using an injector gun with a needle smaller than 19 gauge and preferably being 21 or 22 gauge.

Relatively small intracavitary containers may be used to implant temporarily radioactive spheres in a safe manner without excessive dilation of body parts. These may be inserted in a conventional manner without excessive dilation of body parts. These may be inserted in a conventional manner except that reduced dilation is required. Such intracavitary containers may be inserted and later removed from the bladder, cervix and the like.

Fabric may be used to quickly supply a contoured radiation intraoperatively over wide areas such as the chest and abdomen. It is laid over the entire area. Stiff ribbon may be used to supply microspheres quickly through a tumor.

Figure 19:
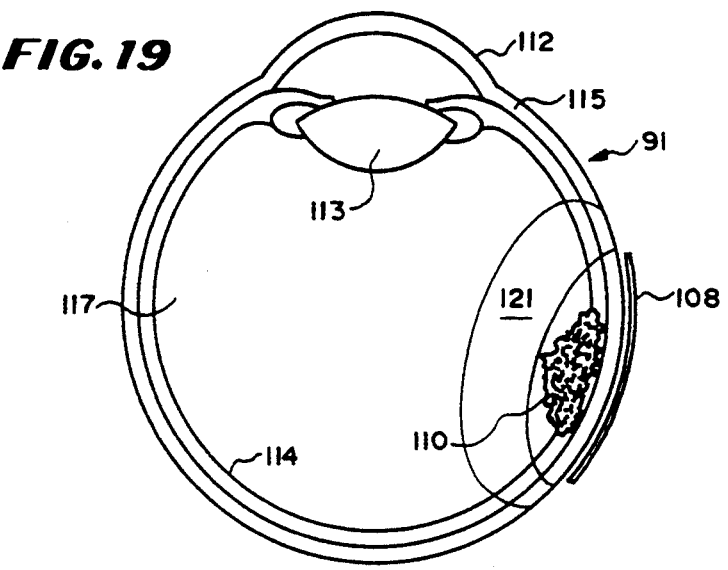
FIG. 19 is a diagrammatic view of an eye showing a manner in which an embodiment of the invention is applied.

In FIG. 19, there is shown a diagramatic view showing the treatment of an eye 91 with a multilayered radioactive ocular plaque 108 positioned adjacent to a tumor 110 adjacent to it. The sectional view of the eye 91 is simplified to show only the cornea 112 a lens 113, the sclera 115, the retina 114 and the vitreas center section 117. With this arrangement, the ocular plaque 108 is positioned adjacent to the tumor 110 with its curved portion mounted to irradiate the tumor 110 with relatively high energy radiation.

To treat the tumor 110, after locating it visually, sonographically, radiographically or using MRI the ocular plaque 108 is selected by size to have minimum overlap on either side of the tumor 110 and to avoid the optic nerve. If the tumor is close to the optic nerve, a plaque having a cup or hemispheric portion is selected and if the tumor is large, a multiple part plaque is used to avoid muscles attached to the globe (rectus muscles). Generally, it is mounted outside the wall of the globe adjacent to the location of the tumor 110 so that its isodose line of 10,000 centi-Gray 121 extends just over and adjacent to the tumor with its lower isodose lines being substantially beyond the tumor so that the highest energy is applied directly to the tumor but normal tissue and adjacent retina is less irradiated.

After the plaque is positioned properly, it is sutured in place for the prescribed period of time, after which the sutures are removed and the plaque removed. The thinness of the plaque facilitates placement, which is usually difficult using state-of-the-art plaques with bulky seed inserts.

In manufacturing the multilayer radioactive microspheres, decisions are first made as to: (1) the intensity of radiation desired; (2) the permanency of the radioactivity desired; (3) the magnetic or ferromagnetic characteristics; (4) tissue compatibility; (5) the ability to be heated by radio frequency radiation for hyperthermia treatment; and (6) its ability to visually identify them such as by X-rays or by magnetic resonance imaging or the like. The substrate is chosen in accordance with this process and the appropriate coats are applied one on the other in intimate contact with each other and with no voids. They are then classified and sent to the customer (when the radioactive microspheres are manufactured directly from radioactive targets or gases). Alternatively, the finished microspheres are manufactured using non-radioactive isotopes. These are sent to be activated in a "neutron oven" and sent to the customer.

The multi-layered radioactive spheres may comprise as many as of six distinct structural components. Four of these are basic to produce a functional multilayer radioactive microsphere and two are optional enhancements. The layers may be applied by any of several processes such as by: (1) sputter-deposition of radioactive dielectric or radioactive metal target followed by sputtering, laser ablation, ion-plating, or cathodic arc deposition of multilayers from non-radioactive targets in non-radioactive gases; (2) reactive sputter-deposition or laser-ablation deposition in excited radionuclide gas followed by sputter-deposition or laser-ablation deposition of multilayers from non-radioactive targets in non-radioactive gas; (3) reactive cathodic arc plasma deposition in excited radionuclide gas and cathodic arc multilayer deposition from non-radioactive targets in non-radiaoctive gas; (4) reactive ion beam sputtering using a cathodic arc ion source in excited radionuclide gas and ion-beam self-sputtering multilayer deposition from non-radioactive targets in non-radioactive gas; (5) reactive ion plating in excited radioncuclide gas and multilayer ion-plating from non-radioactaive targets in non-radioactive gas; and (6) cathodic arc plasma deposition of radioactive dielectric and radioactive metal targets followed by cathodic arc deposition of multilayers from non-radioactive targets.

The central core of the multilayer radioactive microsphere is selected for certain functions. For example, it may consist of a starting solid metal microspherical x-ray marker substrate of high atomic number metal or alloy such as iridium, platinum, gold, tantalum, tungsten or lead. Additionally, a lower atomic weight metal or alloy which is satisfactorily visualized on radiographs may be used including molybdenum, indium, lithium, silver, copper, and steel. Platinum, tantalum, gold, and silver are the preferred X-ray marker MRM core substrate materials in the present invention on conventional radiographs.

In another seed design disclosed wherein only magnetic resonance imaging (MRI) of the seed is clinically desirable and X-ray imaging is not necessary, the seed core is composed of a non-metal such as carbon or glass and an outer seed coat produces a an MRI signal (gadolinium) described below produces the seed image. An MRM without a ferromagnetic metal core is essentially non-magnetic. This absence of ferromagnetic metal is advantageous for clinical situations where multiple seeds are implanted in close proximity to critical structures. In such situations, a strong magnetic field produced by MRI equipment may exert enough force to dislodge or move a metal-containing seed. A magnetically dislodged seed in the brain could cause immediate neurologic damage, stoke, or death of the patient. It could also be lost into the cerebrospinal fluid. For MRI imaging, a non-metal containing multilayer radioactive microspheres would be an improvement over the metal encapsulated seeds currently marketed for clinical usage.

The microspherical substrates are then primed by applying a coat several Angstroms thick of the appropriate primer metal, metal oxide, or metal nitride by means of sputtering or reactive sputtering. Preferred primer metals include titanium, aluminum, tin, tantalum, vanadium, titanium nitride, titanium iodide, titanium oxide, titanium carbide, or metal alloys such as stainless steels or nickel alloys. If the coated material does not have good surface comparability with any primer metal, then a graded interface can be created composed of the substrate material and the radioactive dielecric material.

Another layer consists of an uniformly distributed highly controlled spherical radioacative coat produced by either: (1) radio-frequency (rf), laser ablation, magnetron, or planar magnetron sputter-deposition of a dielectric radioactive coat from a radioactive dielectric target material; or (2) dc or rf sputter-deposition from a target composed of pure electrically conducting radioactive metals. This radionuclide coating is a smooth, spherical, uniform, fine-grained, and thin (less than 0.01 mm to 0.045 mm) radioactive layer that uniformly covers the solid micropherical metal core (substrate).

Also, the target material may be a nonradioactive isotope precursor of the desired radioactive isotope. For example, a multilayer radioactive microsphere containing a primary coat of nonradioactive palladium-102 or samarium-144 is later irradiated with neutrons in a nuclear reactor or in a neutron oven to produce a finished multilayered radioactive microsphere containing radioactive palladium-103 or radioactive samarium-145, respectively.

Another layer may be a dc, rf, laser ablation or magnetron sputter-deposited thin single or multilayered spherical (less than 0.01 millimeter thick) diffusion barrier coating the laminated radionuclide layer.

When the highest quality coat are required, sputter-deposition (direct current dc magnetton, or radio-frequency rf) is the preferred method of producing both the radionuclide coats and diffusion barrier coats because this process is more versatile and is able to produce very thin fine grained smooth surfaces with low peak to valley heights. The sputtering process is highly controllable because many operational parameters of the sputtering process can be changed or adjusted to produce an optimum coat. High coat quality is paid for at the expense of increased manufacturing time due to slower deposition rates and lower energy deposition characteristic of sputter. This may be improved by using large sputter-guns and high-watt power supplies.

Still another layer may be an optional (non-essential) relatively thin (less than 0.01 millimeter thick) rf, magnetron, laser ablation or dc sputter-deposited, or ion-plated, or ion-beam self-sputtered, curvilinear cathodic arc plasma deposited or standard cathodic arc plasma deposited layer or layers of material that have specialized purposes such as magnetic resonance imaging enhancement or positron emission imaging enhancement for seed identification.

A coat such as gadolinium, erbium, terbium, thulium, cerium, cobalt fluoride, dysprosium oxide, dysporsium sulfide, neodymium fluoride, terbium oxide, samarium bromide, thulium oxide, etc. is chosen for the purpose of MRI imaging because of their properties of paramagnetism and high magnetic susceptibility as well as high-boiling point that reduces vacuum welding during coating deposition. Elements or compounds that are suitable or the MRI imaging layer of the present invention include cerium, cobalt fluoride, dysprosium oxide, dysprosium sulfide, erbium, gadolinium, manganese dichloride, neodymium fluoride, samarium bromide, terbium, terbium oxide, thulium and thulium oxide. If lower boiling point materials are to be used, under some circumstances vacuum welding can be prevented by introducing a small amount of oxygen into the sputtering chamber to form an oxide.

Because these elements have sufficiently high boiling points to be effectively coated into the microspheres (boiling points above 2,300 degrees Centigrade are considered higher boiling points for this purpose) and because they have significantly different magnetic susceptibilities, it is possible to separately identify different spheres with different magnetic resonance imaging agents within the same tumor for purposes of tumor dose calculations. To take full advantage of the wide variety of spheres available, it is advantageous to implant more than one type in one procedure into the same tumor. Certain radionuclides with particular energy emissions form a coat that is detected by PET scanner for imaging purposes.

The thick protective coat may be: (1) produced by dc or rf sputtering, planar, magnetron or laser-ablation sputtering, ion plating, ion-beam self-sputtering using a cathodic arc ion source or standard or curvilinear cathodic arc plasma deposition of a metal; or (2) produced by a reactive deposition processes of a compound metal or nonmetallic material.

Some embodiments require low boiling point or soft metals. To coat substrates with these low boiling point metals, such as low boiling point radionuclides without having microspheres fuse together, two targets are used, one of high boiling point harder metal and one of low boiling point softer metal, either simultaneously or one after the other. In the alternative, a target can be prepared with both materials on it. In this specification, high boiling point means in excess of 1,000 degrees Centigrade and low boiling point means lower than 1,000 degrees Centigrade.

The term "high boiling point metals" is used herein to refer to metals or compounds that tend not to vacuum weld when used to coat microspheres in a sputtering apparatus. The term "low boiling point metals" is used herein to refer to metals or compounds that do tend to vacuum weld when used to coat microspheres in a sputtering apparatus. While in many cases these same metals actually do have relatively high boiling points in terms of degrees Centigrade, this is not always the case. Metals with lower boiling points in degrees Centigrade will still be referred to as "high boiling point metals" for the purposes herein.

Thus, the term "boiling point" is correlated with vacuum welding insofar as metals that tend to vacuum weld are generally the same metals that tend to have high sputtering rates also have increasinly-filled "d" shells. Thus, looking at the Periodic Chart of Elements it can be seen that the microsphere coatings used to avoid vacuum-welding come from metals located to the left of the Cu-Ag-Au column, with the Ni-Pd-Pt column being acceptable but marginal, and the Ti-Zr-Hf column being excellent in terms of reduced tendency to vacuum weld.

Metals located in the Periodic Chart of Elements in columns 4, 5, 6, 7, 8, 9 using new notation; or using previous IUPAC notation: columns IVA, VA, VIA, VIIA, and VIIIA (with the exception of Ni, Pd, and Pt from VIIIA) form acceptable microsphere "high-boiling point" coatings to reduce vacuum-welding between microspheres. Be from col 2: B from col 13: C, Si, and Ge from col 14 also form acceptable hard "high boiling point" coatings.

Thus, elements from columns 4, 5, 6, 7, 8, 9 of the Periodic Table of Elements form excellent coatings on microspheres with little tendency to vacuum-weld. These can also be alloyed or laminated with softer metals to form acceptable microsphere coatings. Be from col 2: B from col 13: C, Si, and Ge from col 14 also form acceptable hard coatings.

Elements from column 10 form acceptable to marginally-acceptable coatings that can be produced by adding dopant gas such as oxygen.

Elements in columns 11-17 (previous IUPAC IB, IIB, IIIB, IVB, VB, VIB, VIIB) to the right of column 10 including aluminum, copper, gold, silver, and (excluding carbon-diamond coatings and boron coatings, and silicon and Ge coatings) tend to vacuum-weld and form unacceptable microsphere coatings unless they are alloyed or laminated with a hard element from columns 2-9. Elements from columns 1 and 2 are also unacceptable with the exception of Be and possibly Ra.

Another criteria for acceptable microsphere coatings is a coating hardness of greater than 4.0 on the MOHS scale. This criteria also applies to compounds whereas the previous periodic table rule only applies to individual elements.

Some acceptable microsphere metal coatings that tend not to vacuum-weld are Be, Ti, Zr, Hf, V, Nb, Ta, Cr, Mo, W, Mn, Tc, Re, Fe, Ru, Ir, Ni (dopant gas necessary), Pd (dopant gas necessary), Pt (dopant gas necessary, B, C (diamond only), Si, Ge. The element may be a radioactive isotope.

TABLE 59

| COMPOUND | HARDNESS RATING |
|---|---|
| chromium boride | 1,800 kg/mm$^2$ |
| hafnium boride | |
| molybdenum boride | 8 MOHS, 1,570 kg/mm2 |
| tantalum boride | |
| thorium boride | |
| titanium boride | 3,400 kg/mm2 |
| tungsten boride | 9 MOHS |
| uranium boride | 8-9 MOHS |
| vanadium boride | 8-9 MOHS |
| zirconium boride | 8 MOHS |
| diamond | 10 MOHS |
| ZnS, zinc sulfide | 1,780 kg/mm2 |
| ZnSe, zinc selenide | 1,350 kg/mm$^2$ |
| BH, boron nitride | 10 MOHS |
| BP, boron phosphide | 37,000 kg/mm$^2$ |
| BA, boron arsenide | 19,000 kg/mm2 |
| AlP, aluminum phosphide | 5.5 MOHS |
| BeO, berrylium oxide | 1250 (Knoop value) |

TABLE 60

| COMPOUND | HARDNESS RATING |
|---|---|
| zirconium boride | 1550 Knoop |
| titanium nitride | 1800 Knoop |
| tungsten carbide | 1880 Knoop |
| tantalum carbide | 2000 Knoop |
| zirconium carbide | 2100 Knoop |
| aluminum trioxide | 2100 Knoop |
| berrylium carbide | 2410 Knoop |
| titanium carbide | 2470 Knoop |
| silicone carbide | 2480 Knoop |
| aluminium boride | 2500 Knoop |
| boron carbide | 2750 Knoop |
| diamond | 7000 Knoop |
| iron arsenic sulfide | 6 MOHS |
| zirconium dioxide | 6.5 MOHS |
| titanium dioxide ("Tiox") | 6 MOHS |
| nickel oxide | 5.5 MOHS |
| tin dioxide | 7.0 MOHS |
| cobalt arsenic sulfide | 5.5 MOHS |

TABLE 61

| COMPOUND | HARDNESS RATING |
|---|---|
| SiO$_2$, silicone dioxide | 7.0 MOHS |
| Mn$_3$O$_4$, manganese oxide | 5.5 MOHS |
| FeAs$_2$, iron arsenide | 5.5 MOHS |
| MnO, manganese oxide | 5.5 MOHS |
| FeS$_2$, iron di-sulfide | 6.5 MOHS |
| SiC, silicone carbide | 9.5 MOHS |
| NiAs, nickel arsenide | 5.5 MOHS |
| MgO, magnesium oxide | 5.5 MOHS |
| FeS, iron sulfide | 6.5 MOHS |

TABLE 61-continued

| COMPOUND | HARDNESS RATING |
| --- | --- |
| MgF$_2$, magnesium fluoride | 5.0 MOHS |
| Pt As$_2$, platinium arsenide | 7.0 MOHS |
| ThO$_2$, thorium oxide | 6.5 MOHS |
| NiSbS, nickel-antimony sulfide | 5.5 MOHS |
| UO$_2$, uranium dioxide | 6.0 MOHS |

Some unacceptable microsphere metal coatings that tend to vacuum-weld are Cu, Ag, Au, Zn, Cd, Hg, Al, Ga, In, Tl, Sn, Pb, P, As, Sb, Bi, S, Se, Te, Po, Cl, Br, I, and At.

Table 59 gives some acceptable compounds for microspherical coatings that do not vacuum-weld followed by their hardness rating. One of elements may be radioactive isotope of element. These may be laminated or alloyed with softer metals to form acceptable microsphere coatings.

Table 60 gives some acceptable compounds for microspherical coatings that do not vacuum-weld followed by hardness rating. One of elements may be radioactive isotope of element. These may be laminated or alloyed with softer metals to form acceptable microsphere coatings.

Table 61 shows some acceptable compounds for microspherical coatings that do not vacuum-weld followed by hardness rating. One of elements may be radioactive isotope of element. These may be laminated or alloyed with softer metals to form acceptable microsphere coatings.

Because of spherical uniform construction, any self-shielding can be compensated for by increasing the seed activity. In the preferred embodiment of this invention, titanium (low atomic weight with minimal shielding of low-energy gamma rays, tissue and corrosion resistant, high hardness and boiling point) is the preferred metal casing used for construction of multilayer radioactive microspheres containing low energy emitting (less than 100 KeV) radionuclides, and tantalum (high atomic weight with some shielding of low-energy gamma rays and very little shielding of high energy gamma rays, highly tissue and corrosion resistant, high hardness and very high boiling point) and is the preferred metal casing used for construction of multilayer radioactive microspheres containing high-energy emitting (greater than 100 KeV) radionuclides.

If necessary, to reduce porosity or remove crystallization of the coatings of the finished product, or to improve adhesion between layers, after completion of coating, the microspheres may be annealed by heating close to the bulk metal melting temperature in a microsphere bouncing pan.

The sputtering and other deposition techniques as practiced in this invention are substantially adaptations of existing systems and will not be described in detail herein. The adaptation can be made with knowledge of the parameters of the equipment such as the rate of deposition and the materials which can be deposited coupled together with an explanation of the microspheres, wires and fabrics disclosed herein. However, the techniques are modified to form radioactive layers in some embodiments that: (1) sputter or otherwise coat in a high energy vacuum process "high and low boiling point radioactive metals" (as previously defined on page 184) together or as interleaved layers while levitating or bouncing the spheres to prevent sticking of the spheres; and (2) in other embodiments, sputter or otherwise coat in high energy vacuum processes a gaseous radioactive nuclide and non-radioactive metal to form a radioactive metal compound coat because of the reaction of the metal target material and the gas radioactive nuclide to form a radioactive compound coat.

Figure 20:
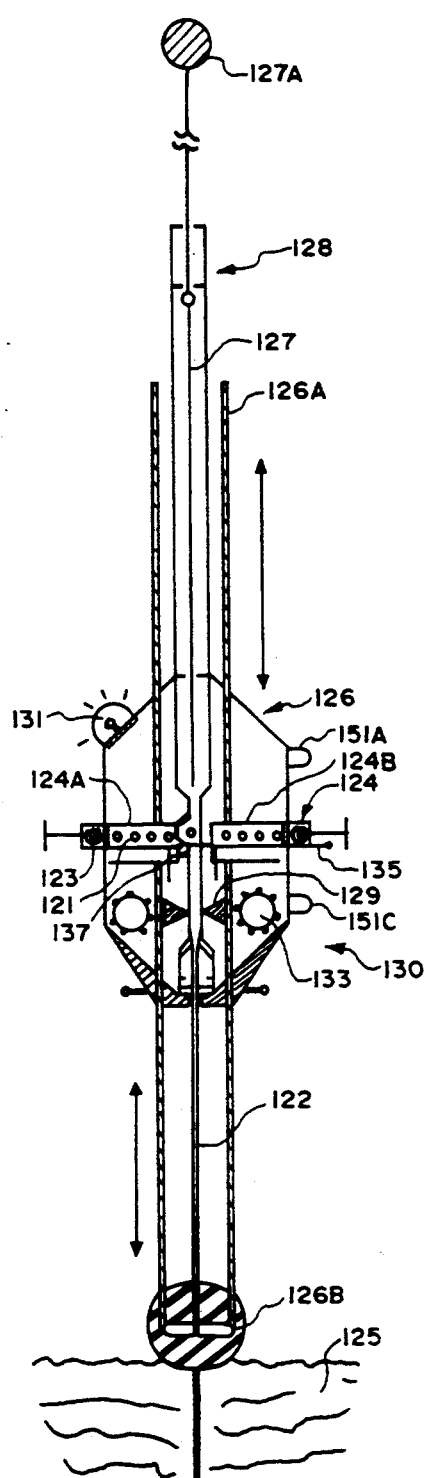
FIG. 20 is a diagrammatic view of an implant gun.

In FIG. 20, there is shown a simplified view of an injector gun 120 for multilayered radioactive microspheres having a needle 122, a seed container assembly 124, a housing 126, a stylet assembly 128, and a motor assembly 130. The ejector 120 is similar to existing ejectors except that: (1) the needle 122 may have a diameter much smaller than the existing seed guns and is no larger than 20 gauge; (2) there is an electronic radioactive seed detector to indicate when a seed is loaded into the chamber; (3) the seed container assembly is circular in shape; (4) the housing is made of radiation-shielding material to protect the operator's hands; and (5) the seed cartridges contain spherical rather than cylindrical seeds. An existing gun is sold by Mick Radio-Nuclear Instruments, Inc., 1470 Outlook Avenue, Bronx, N.Y., 10465 under the designations Mick Application catalog 7308 and 1-125 Gun catalog 8006.

The seed container assembly 124 is circular in shape and includes a plurality of removable and replaceable seed cartridges, two of which are shown at 124A and 124B, which may include seeds of differing activity or type. The injector gun 20 may be mounted to a robotic arm by four eyelets two of which are shown at 151A and 151C. Only the cartridge 124A will be described since the others are substantially the same.

The cartridge 124A includes a seed compartment 121 containing a plurality of spherical seeds compressed by a spring biased plunger 123 and a rotatable release plate having a slot alignable with any of the cartridges to release one seed into the needle 122 each time the plunger is depressed. Beneath the slot is a pair of spring biased bearings at the distal seed chamber which extend into the needle 122 at a location that blocks the path into the needle 122 until the seed is pushed by the stylet, opening bearings 137. With this arrangement, rotation of the slot permits release of a seed from the selected cartridge.

The housing 126 is made of radiation-shielding material to protect the operator's hands. It includes a tubular wall 126A that slides through the housing at either 2 mm or 5 mm increments along its longitudinal axis with the seed container assembly 124 and motor assembly 130 being mounted to it at a central position. It includes at one end a tissue pad 126B for positioning against tissue 125 to permit passage of needle 122 therethrough into the tissue. When assembly 126 is attached to a robotic arm, tissue pad 126B and wall 126A is fully retracted and not used.

To provide a guide for seeds, the needle 122, which is 20 centimeters long and 21 to 22 gauge to permit deep penetration, extends through the tissue pad and upwardly through the housing to the stylet assembly 128, having an opening to receive seeds located adjacent to the seed container assembly.

To force seeds one at a time through the needle 122, the stylet assembly 128 includes a needle stylet 127, 24 centimeters long that fits into the needle 122 and is able to force a seed therethrough for implanting in tissue and a needle stylet handle 127A, 24 centimeters long for forcing a seed from the needle tip or up to the needle tip for release by moving the tubular wall 124 upwardly.

Elements such as palladium-102 can be made radioactive by neutron irradiation which converts them to radioactive palladium-103. Thus, seeds can be packaged in the cartridge 128B as non-radioactive seeds, shipped to a licensed facility and bombarded with neutrons in a neutron oven to make them radioactive and then shipped in a shielded container to the end user.

The motor assembly 130 includes a radiation seed detector diode 129 that detects a seed and provides an indication in indicator lamp 131. The injection of a seed in the needle is accomplished by withdrawing stylet 127 to expose the chamber to the selected cartridge to cause a seed to enter the tube. The stylet is used to block the tube against further seeds and to force the seed to the tip of the needle. Seeds are prevented from falling into needle by a set of spring-loaded ball bearings on each side of seed chamber advancing the stylet deposits a seed in the tissue. The servometor 133 moves the tube downward and needle upwardly at 2 mm to 5 mm increments.

Figure 21:
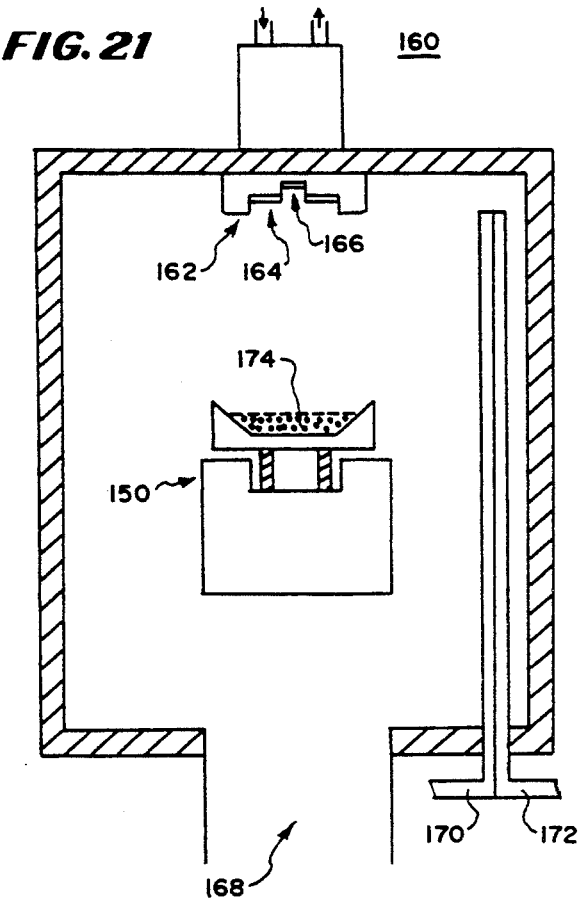
FIG. 21 is a schematic diagram of one embodiment of equipment for making microspheres.

In FIG. 21, there is shown a sputtering device, which in this example is a radio-frequency sputtering device 160 having a source of rf power 162 mounted adjacent to a target 164 spaced slightly from an anode 166 to cause the material deposited to be sputtered off into a vacuum chamber. The vacuum chamber is maintained in a vacuum through the vacuum conduit 168. A radionuclide gas is supplied to the vacuum chamber through a conduit 170 together with the appropriate mixture of argon gas supplied through another conduit 172 to create an atmosphere in which a radionuclide gas may be combined with the target material for application to microspheres.

To mount the microspheres for uniform coating, a levitation pan 150 contains the microspheres located generally at 174 and contiually bounces them by vibration so as to permit access to all sides for even coating. Some levitating devices are available commercially or may be constructed as described below.

Figure 22:
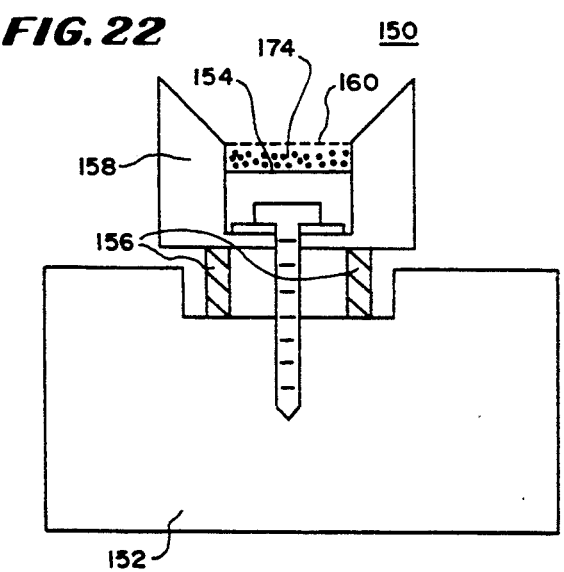
FIG. 22 is a schematic diagram of another embodiment of apparatus for making microspheres.

In FIG. 22, there is shown an enlarged schematic view of the levitation pan 150 containing a holder for the microspheres mounted within a pan 154 and held by a cage 160. Vibrators, 156, which may be crystalls are positioned to be vibrated electronically so as to bounce the microspheres shown in 174.

Figure 23:
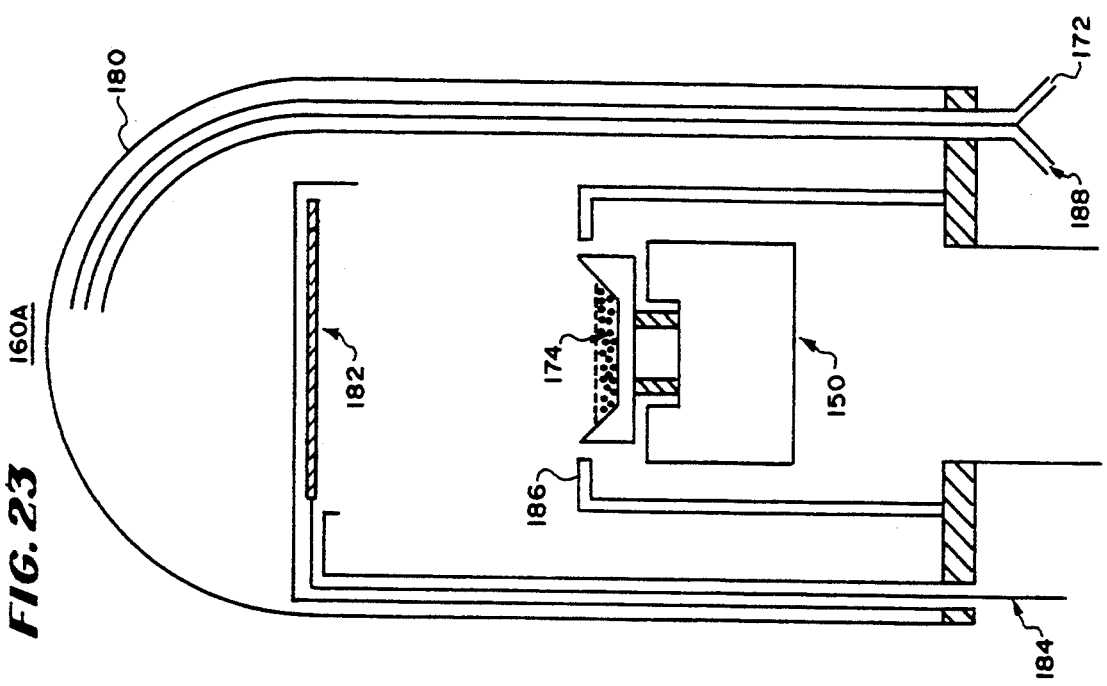
FIG. 23 is a schematic diagram of still another embodiment of apparatus for making microspheres.

In FIG. 23, there is shown another embodiment of sputtering device 160A having a cathode target 182 with the material to be coated, a high voltage potential 184, an anode 186 a levitation device and a source of radionuclide gas 188. The cathode target 182 is energized through the conductor 184 to a high potential which causes the material to be plated to be drawn to the anode 186 and coated on the charged levitated microspheres 174. The radionuclide gas 188 may be applied for combining through the conduit 188 in a proper argon gas atmosphere 172 while a vacuum is maintained in the usual manner.

Figure 24:
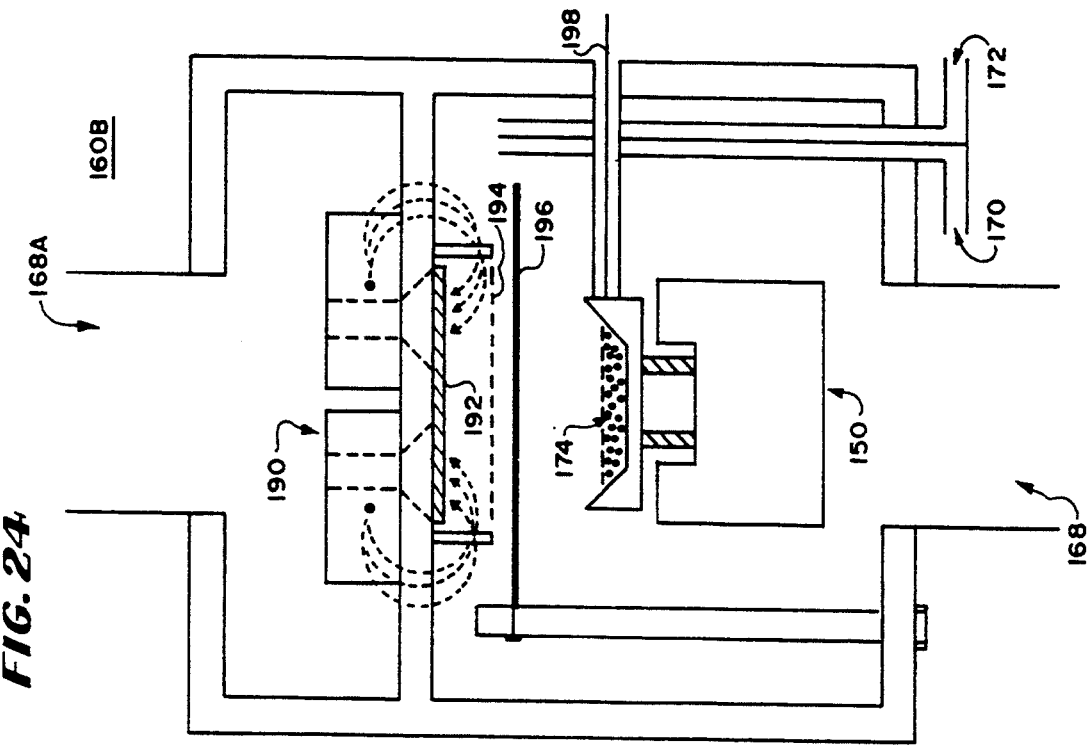
FIG. 24 is a schematic diagram of still another embodiment for making microspheres.

In FIG. 24, there is shown another embodiment of a coating apparatus for sputtering having a vacuum chamber evacuated through the conduits 168 and 160A, an electron beam source 190, target 192, confined by a grid 194 in shutter 196, a source of high frequency rf or positive or negative high voltage 198 substrate bias and the levition pan 150.

In this embodiment, electron beams are emitted to bombard the target 192 and remove sputtered material which is attracted to the radio frequency or high frequency connection to the cage containing the microspheres 174. A radionuclide gas can be applied through the conductor 170 with an argon atmosphere maintained through the conduit 172 in the same manner as in the previous embodiments. The microspheres may be vibrated to provide an even coat from the material from the target and/or radionuclide gas.

Figure 25:
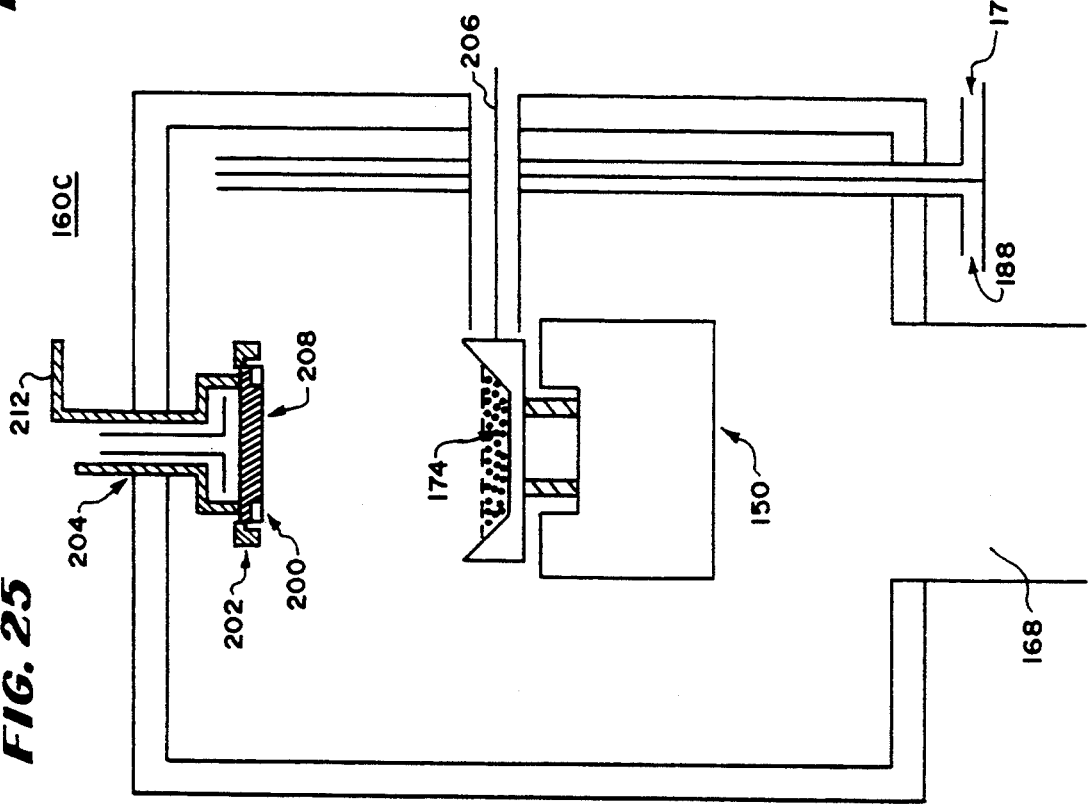
FIG. 25 is still another embodiment of apparatus for making microspheres.

In FIG. 25, there is shown another embodiment of coating device 160C having an arc cathode 204, anode 202, a target 208, the levitation pan 150 and a source dc or rf of bias voltage 206 maintained in a vacuum chamber from which vacuum pressure is drawn by a vacuum pump through the conduit 168. The target has coating materials spun off from it under high voltage from an arc supply 212 for drawing by means of the negative or rf bias 206 to the microspheres 174 in the levitation pan 150. Radionuclide gas can be supplied through the conduit 188 and argon gas through the conduit 172 in the manner of the other embodiments so as to coat particles.

Figure 26:
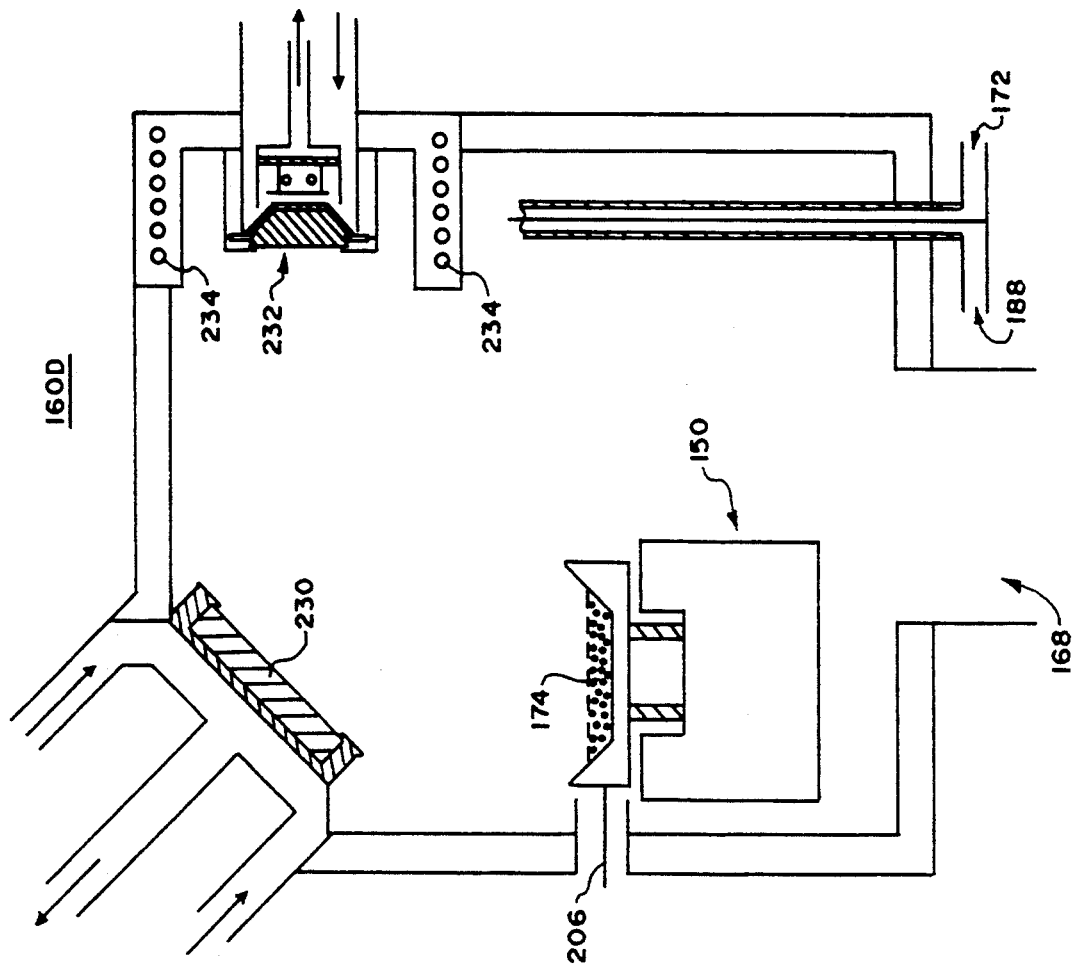
FIG. 26 is still another embodiment of apparatus for making microspheres.

In FIG. 26, there is shown another embodiment 160D of sputtering agent having a target 230 a source of ions 232, a controlling solinoid 234, and the levitation pan 150 in a vacuum compartment evacuated through the conduit 168. The ion source 232 generates ions which are propelled by the solinoid 234 against the target 230 to sputter off material which is drawn by a bias potential 206 to the microspheres 174 being levitated in the levitation pan 150. A radionuclide gas can be applied through the conduit 188 together with argon through the conduit 172 for incorporation of a radionuclide onto the coated material.

In FIG. 27, there is shown still another coating apparatus 160E having a tubular plasma guide 250 extending from an anode having a target 256 mounted to it about an arc cathode 258 on one end and the levition pan 150 supporting the microspheres 174 on the opposite end. Guide coils 260 maintain a field around the plasma guide duct at 250 to guide plasma to the microsphere. The conduits 188 and 172 for applying radionuclide gas and argon respectively to the microspheres communicate with the levitation pan directly. An exit solinoid 270 channels the plasma directly onto the levitated microspheres. Only "clean" charged plasma reaches the microspheres and neutral macroparticle contaminants are eliminated. The microspheres and the exit end of the plasma duct are all encased in a vacuum compartment evacuated by a vacuum turbomoleculer pump through the conduit 168.

In FIG. 28, there is shown another embodiment of coating apparatus 160F having the levitation apparatus 150 for bouncing spheres 174, conduits 172 and 188 plus any auxiliary conduits required for introducing inert gasses and reactive gasses and radioactive gasses and seven magnetrons, three of which are shown as 350, 352 and 354 within a vacuum enclosure evacuated through a conduit 356 by a turbo-molecular pump, a conduit 358 by a diffusion pump and a conduit 360 by a vacuum pump, depending on the mode of operation of the apparatus. A bias voltage may be applied to the microspheres in the levitation apparatus through an electrical connection 362.

With this arrangement, any of the seven magnatrons including 350, 352 and 354 may cause targets mounted to it to sputter off coating material which, in some instances may be combined with radionuclide gasses such as radioactive hydrides to form compounds composed of the gas and a target metal for preparing a radioactive coat. Other materials for other coats of a microsphere may be sputtered off for application to the spheres under a bias transmitted to the spheres through the conductor 362. In this embodiment, the magnatron 350 is a three inch magnatron, the magnatron 352 is an eight inch magnatron and the magnatron 354 is a six inch magnatron.

The target materials are selected in accordance with the purpose for the coat and the thickness of the coat. The larger magnatron is used for thicker coats to provide a faster coating operation. To energize reactive gasses, a 13 megahertz (mHz) radio frequency excitation coil 362 is provided adjacent to the conduits 172 and 188. Each of the magnatrons 350, 352 and 354 includes a corresponding source of radio frequency power 350A, 352A and 354A, corresponding coolant 350B, 352B and 354B targets 350C, 352C and 354C and shutters for the targets 350D, 352D and 354C.

With this arrangement, the higher powered magnatrons are capable of spinning off target material from a larger surface area to provide a higher rate of reaction and thus enable the same apparatus to prepare different coats of different materials in a step by step manner.

Figure 29:
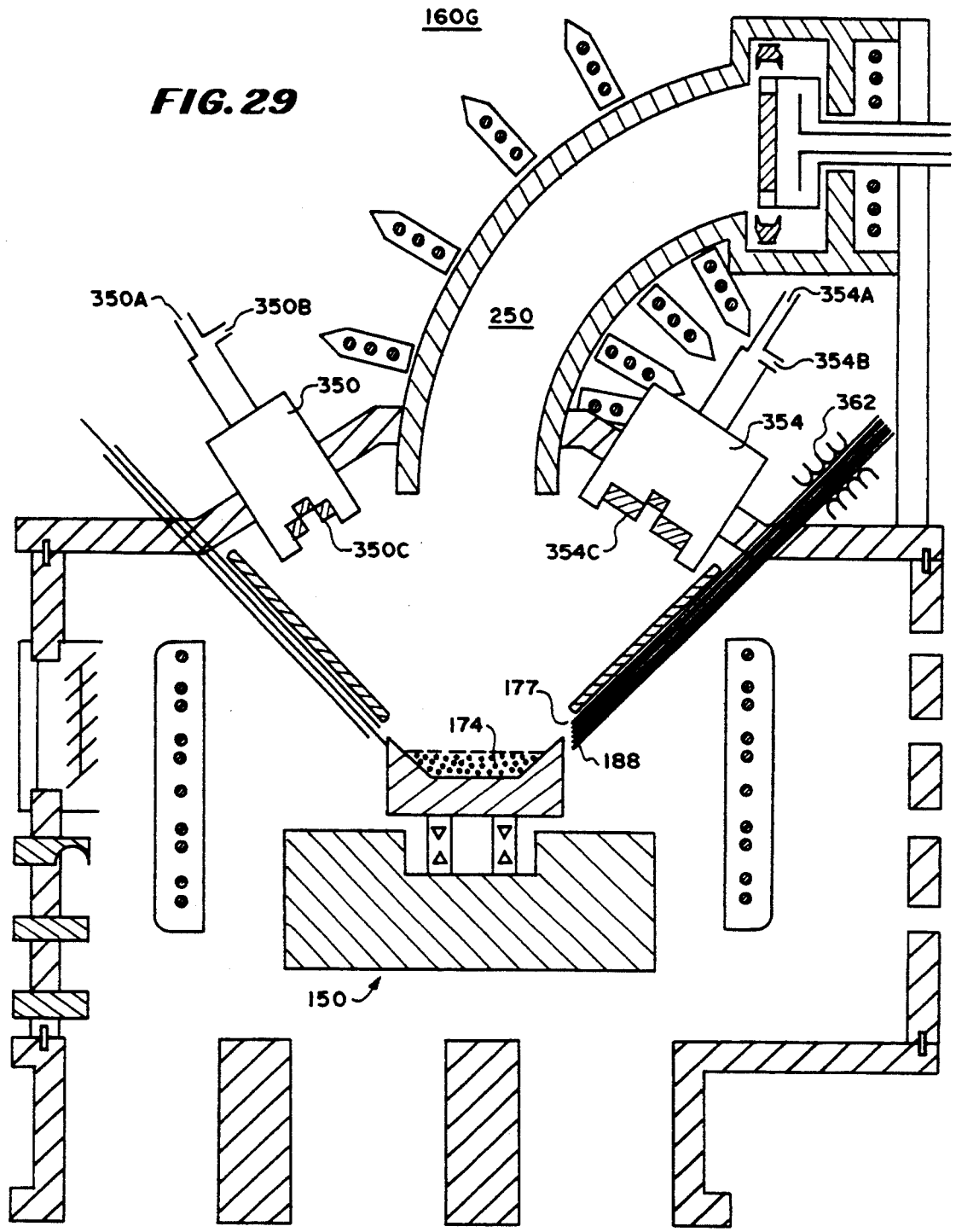
FIG. 29 is still another embodiment of apparatus for making microspheres.

In FIG. 29, there is shown another embodiment of coating apparatus. In FIG. 29, there is shown another embodiment 160G of coating apparatus similar to the embodiment 160F of FIG. 28 except instead of the larger magnatron, a plasma source similar to that of the embodiment of 160E is used to provide macroparticle-free plasma beams to the levitated microspheres from a cathodic arc target to provide a pure uniform coat. The device contains six magnetrons and one cathodic arc source with a curvilinear plasma tube with solenoids used to clean neutral macroparticles from the charged plasma beam.

Figure 30:
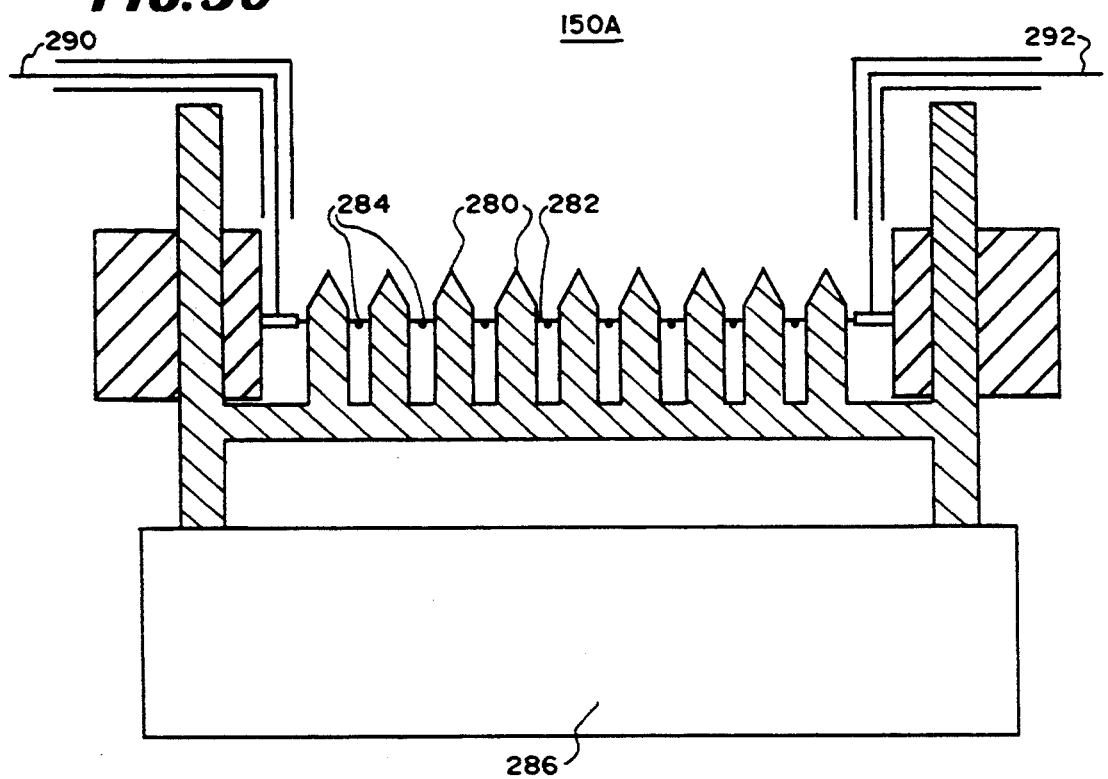
FIG. 30 is a schematic diagram of an apparatus for preparing radiation-emitting ribbon.

In FIG. 30, there is shown another holding apparatus 150A for multilayered radioactive implants having a plurality of mask members 260 overwhich a fabric or ribbon 282 to which microspheres 284 are attached is mounted. The mask is mounted to a base 286 and bias voltages are applied to the microspheres through electrical connections shown at 290 and 292. A stepping motor rotates the ribbon or fabric strip to apply coats evenly to the microspheres 284 This holder may be mounted within any of the coating apparatus 160-160G instead of the levitating apparatus 150.

With this arrangement, the microspheres may be coated while on a ribbon or fabric in the manner described above either in a one-by-one manner or with a plurality of them being energized at once for coating. Different coats may be applied to different microspheres for the purpose of providing a contoured radioactive effect along the ribbon or a different locations on the fabric and the coats may be applied one by one.

Any form of deposition may be used with this apparatus and the bias may be adapted from microsphere to microsphere or by masking so as to obtain the desired effect of different amounts of radiation from different microspheres. Moreover, the radionuclide gas may be selected with a metal to form a metallic radioactive coat that contains the gaseous radionuclide introduced into the container.

Figure 31:
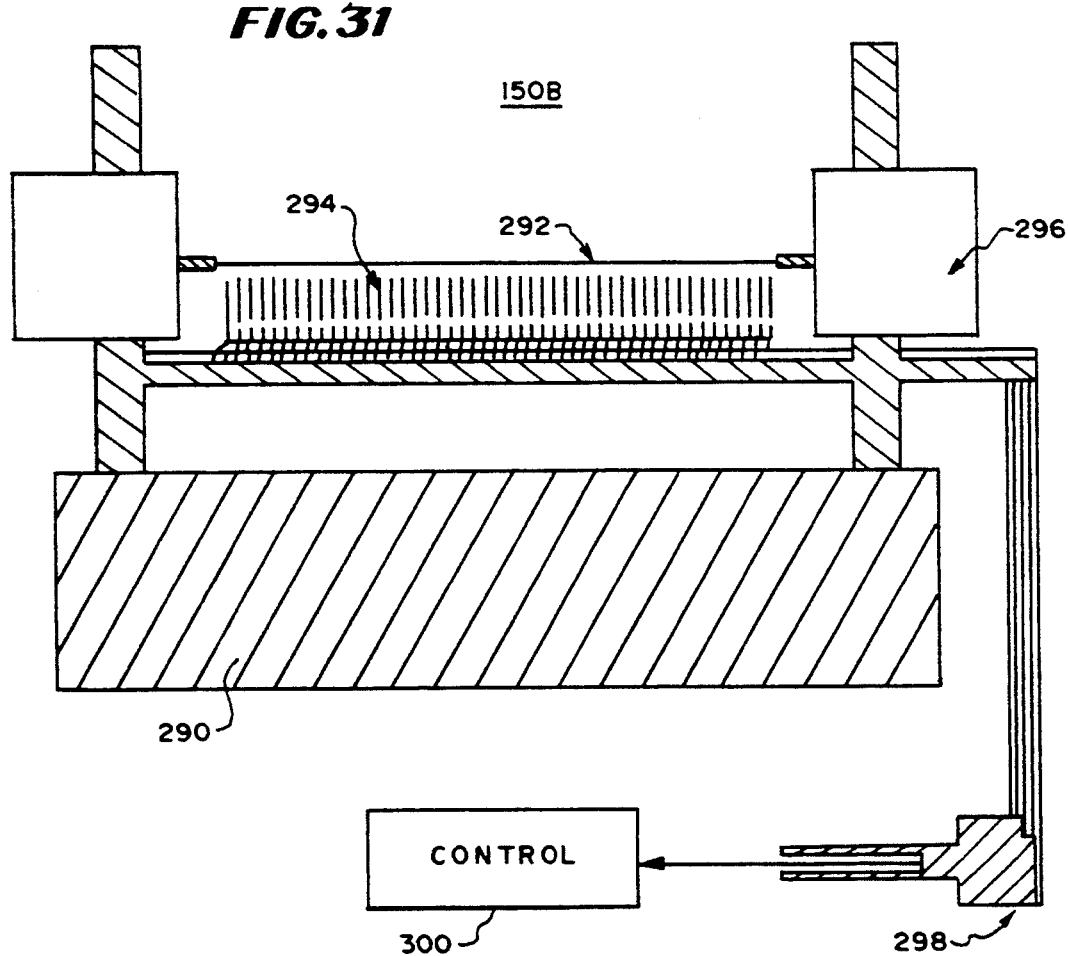
FIG. 31 is a schematic diagram of another embodiment for producing variable deposition of radionuclide per unit length along elongated radiation-emitting members.

In FIG. 31, there is shown still another embodiment 150B of coating apparatus for coating a wire 292. This coating apparatus provides a differential radioactivity along the length of the wire and includes a base 290, a differential bias voltage array at 294, a stepping motor 296, a digital to analog amplifier 298 and control mechanism 300 for rotating the wire from angular position to angular position for even coating. The differential bias 294 is controlled through the digital to analog convertor 298 and provides a differential bias along the wire 292. The control of a computer or other device as shown at 300. With this arrangement, since the bias is varied, the sputtered material onto the wire differs from location to location along with wire to provide preprogrammed radioactive contour. A similar arrangement holds an optical plaque or ribbon or fabric and provides a layer area differential bias to create a contoured layer of preprogrammed radioactivity by controlling the thickness of the radioactive layer from location to location.

Figure 32:
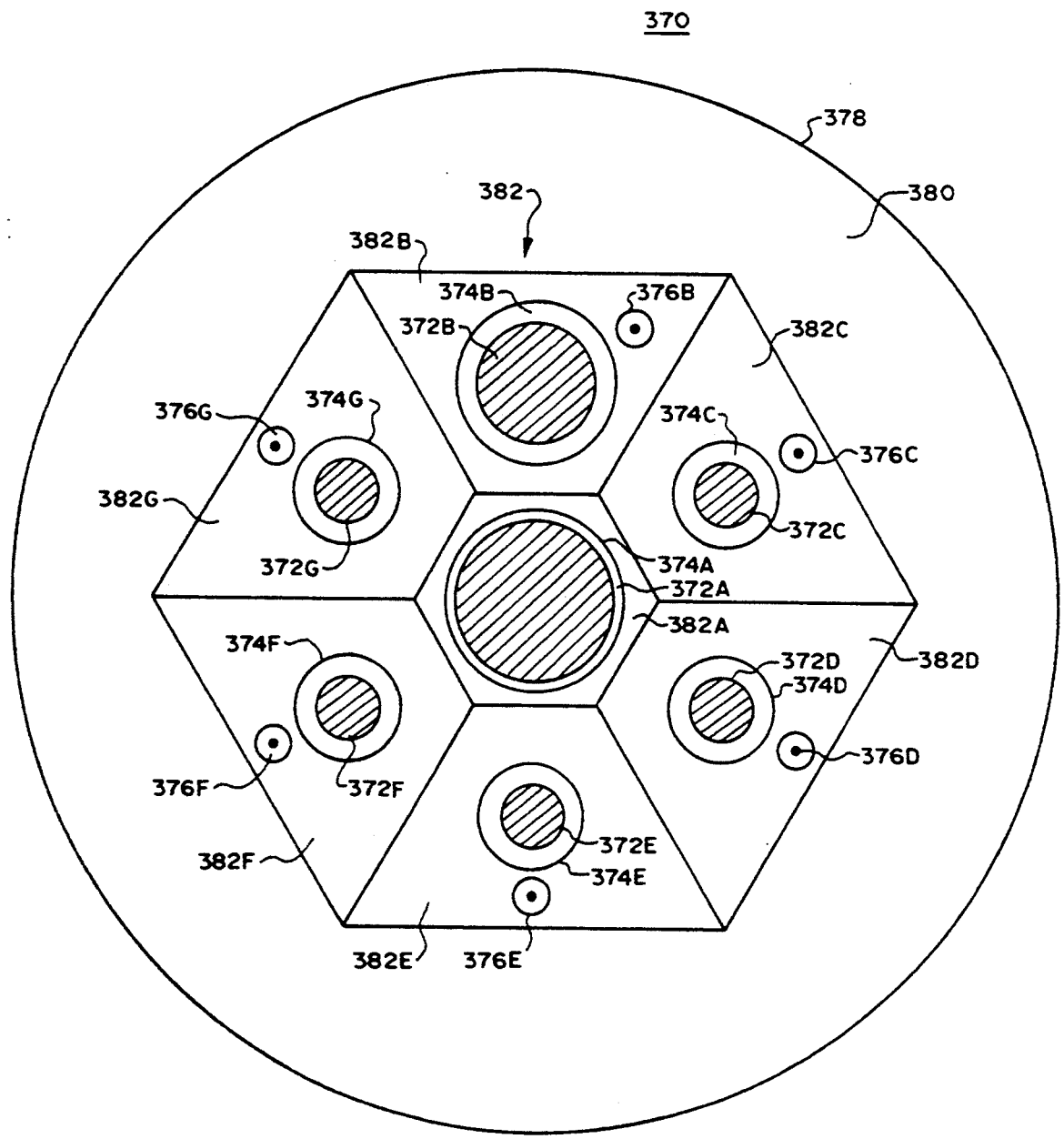
FIG. 32 is a schematic diagram of an embodiment of target assembly for use in an apparatus for making microspheres.

In FIG. 32, there is shown a composite target topplate 370 having a target of the type used in the embodiment of FIG. 28 holding plate 380, an O-ring 378, and a centrally located composite target holding plate 382. The plate 380 is circular and surrounded the O-ring 378 to permit fitting with any of the vacuum chambers of the previous embodiments to provide a target containing a plurality of target materials and suitable target sources for applying sequentially coats on multilayered elements or for aiding in the preparation of a composite target material which contains a metal compound of a nuclide gas such as a radioactive hydride gas.

To provide a plurality of target sources, the composite target plate 382 includes six sections 382A–382G each of which supports a different target and each of which is located in an angled plane to permit focusing upon a single element to be coated with multilayers. To provide sputtered material to a multilayered element being coated, each of the target plates 382A–382C includes a corresponding one of the target materials 372A–372G, sources of ions or sputtering energy such as cathodic arc sources or magnatron sources 374A–374G, and feed through conduits to support shutters for closing off certain of the target areas 376B–376G.

With this arrangement, selected sources may have the shutters closed for convenience while one other is energized to sputter off material onto an element to be coated. Alternatively, each target can be sequentially activated by vaporizing the target material with a laser beam as in laser ablation sputtering. Consequently, in each of the targets 370, there is at least one radionuclide material and one material for each of the other coats to be applied to a multilayered radioactive element or there is one metal adapted to be combined with a gaseous radioactive nuclide to form a metal-radionuclide coat within the vacuum chamber and one metal for each of the other different layers to be applied to the multilayer radioactive element.

The target having a radioactive nuclide may be formed in any of the previous apparatus for forming coats by positioning the target within the coating apparatus to receive a sputtered material and sputtering the materials metal onto it from another target. In one embodiment, a target containing a radioactive compound is formed by sputtering a metal in combination with the appropriate radioactive nuclide hydride gas to form a metal radioactive nuclide compound on the target being formed. Thus, the target being formed will contain a sputterable material which has as part of it a radioactive metal compound corresponding to the normal gaseous radioactive nuclide.

While any configuration may be prepared using this target as described in this application, a typical example is for the support 382A to include an eight inch central magnatron target of titanium 372A adapted to be energized by the magnatron 374A used to produce a thick protective coat, the support 382B to include a six inch magnatron target composed of an alloy of gadolinium, nickel, palladium and iron and used to produce magnetic coating, the support 382C to include a three inch magnatron target containing samarium bromide pressed powder as the target 372C used to produce magnetic resonance imaging coat and a three inch magnatron 374C for energizing the compound, for support plate 382D to include a tungsten target 372D used to laminate radioactive titanium iodide-125 coat or form diffusion barrier of tungsten or tungsten nitride and a three inch magnatron 374D; the support 382E to include a titanium plate target 372E used to form radioactive titanium iodide-125 by sputtering in radioactive iodine-125 gas or used to form titanium nitride laminate or diffusion barrier. A three inch magnatron 374E, the support plate 382F to contain a target of Hafnium to produce HFN colored coat and the support plate 382G to include a titanium $Ti(I-125)^2$ target and a three inch magnatron 374G to serve as the single radioactive nuclide source.

As can be understood, the large central target support plate 382A because it is recessed into the face of the paper with other targets at an angle and arranged to focus on the same location. In the example of FIG. 32, the central target is large and most suitable to sputter off the material for the thicker protective layer whereas the surrounding targets are most suitable for the thinner coats but may involve any source size depending on the rate of deposition required and the boiling point of the material to be sputtered.

The radioactive single seed design of this invention has several advantages such as: (1) it is smaller than prior art radioactive seeds and is spherical thus permitting a wider range of uses and easier use with less traumatic insertion into human tissues; (2) it is stronger and has high structural integrity and is thus safer; (3) it is symmetrical and spherical and uniform and thus produces a symmetrical and spherical radiation field as shown by symmetrical dosimetry; (4) it may be constructed using a wide variety of isotopes of differing energies and half-lives selected for specific applications, thus permitting optimization of the radiobiology of the type of cancer being treated; (5) it is inexpensive; and (6) in clinical practice, it permits safe delivery of radiation tumor doses that are two to five times higher than that achieved with external beam irradiation; (7) the different multilayered radioactive microspheres can be identified by their different imaging contrast agent coats or center substrate and (8) dose-rate control for purposes of radiosensitization is easily accomplished incorporating a variety of over 220 radionuclides of various half live energies and activities.

In use, the microspheres have several advantages such as: (1) an effective modality for treatment is provided by combining a relatively low continuous dose of radiation by multilayer radioactive microspheres implanted in a tumor at any anatomic location and which serve as radiosensitizers so that a short fractionated conventional course of external-beam radiation therapy is much more effective; (2) radiation dose localization is improved beyond that achievable with the low energy permanent gamma-ray seeds by use of an electron-producing seed because electron dosimetry is more localized than X-ray dosimetry; (3) different types of multilayered radioactive microspheres with different half-lives and photon or electron energies can be implanted into a tumor in the same operation to optimize tumor therapy; (4) the use of permanent implantation of short-lived seeds rather than temporary-removable implants eliminate exposed tubes which penetrate the skin surface and serve as a route for infection over many days; and (5) microspheres can be implanted into tissues using thin-gauge needles reducing risk.

There are also advantages from the composite designs that can be produced using the spheres, such as for example: (1) ribbons and a tissue-compatible fabric containing seeds useful for rapid surgical implantation may be produced; (2) the thin ribbon design containing multiple seeds allows rapid implantation of multiple seeds using a hollow interstitial needle; (3) a tissue-compatible surgical fabric containing multiple radioactive seeds allows rapid intraoperative implantation of a sheet of evently spaced radioactive seeds; and (4) the various surgical procedures and devices used for implantation of radioactive seeds provide better adaptability to a patient's needs.

There are also advantages from a wire multilayered radioactive design such as: (1) it may be cut up into pieces and placed into afterloading catheters or into nylon or polyethylene ribbons for temporary removable implants or placed inside appropriate containers to construct various intracavitary sources; (2) it has the advantages of being flexible or remain as a long needle, with or without an added sleeve for temporary implanting.

When encapsulated: (1) the multilayered radioactive microspheres or wires simplify intracavitary therapy because smaller intracavitary capsules can be construced using multiple small-diameter seeds of the present invention; (2) a wide variety of radionuclides with energies varying from very low to very high can be incorporated into composite intracavitary sources by sealing multiple multilayered radioactive microspheres of one or several types into an appropriate container; (3) use of low energy intracavitary sources composed of low energy multilayered radioactive microspheres or wires allow selective shielding of adjacent vital structures such as rectum and bladder using relatively thin high atomic weight foils placed over the intracavitary sources or source holders.

There are also several advantages related to manufacturing the radioactive implants such as: (1) it permits mass production of a variety of designs without need of assembly of separate (radioactive) parts; (2) changes in seed composition may be made easily; (3) it permits customized manufacture of multilayered radioactive microspheres, multilayered radioactive wires, ribbon-multilayered radioactive microspheres or ocular plaques optimized for individual tumor types; (4) manufacture of a new models of multilayered radioactive microspheres, multilayered radioactive wires and ribbon-multilayered radioactive microspheres can be accomplished as needed by changing deposition parameters the type, thickness, and layering of deposited elements using the same deposition equipment; (5) it permits construction of seeds containing many optional different types of laminated materials such as imaging contrast agents, colored seed identification markers, or supplemental protective outer layers; (6) use of the high energy processes of sputtering, laser ablation vacuum deposition, ion-beam sputtering, cathodic arc or curvilinear cathodic arc plasma deposition, reactive deposition, and ion plating increase the hardness of metals coated in this manner compared to the bulk materials; and (7) the controlled variable deposition of radioactive material per unit length or per unit surface area permits customized manufacture of brachytherapy sources to exactly match the requirements of 3-dimensional computerized brachytherapy treatment plan.

The ability to provide a variety of half-lives and intensities of implants has several advantages, such as for example: (1) the smaller permanent seeds permit implantation of a greater number of seeds in more body sites using thinner needles with less risk of complication; (2) a combination of short-acting high-energy and long-acting low energy seeds can be implanted in the same procedure; (3) under some circumstances repeated implantation of seeds with short half-lives may be used instead of repeated temporary removable implant procedures thus reducing the risk of infection associated with temporary removable implants; (4) high energy short-lived seeds provide results equivalent to a temporary removable implant, but they may be applied to sites not accessible to temporary removable implantation; (5) short-lived seeds may be implanted as a "tumor-boost" replacing and improving upon a "tumor-boost" delivered by means of external-beam radiation thearpy; (6) with a wide variety of seeds available, many cancers can be more effectivley managed by brachytherapy alone; (7) a wide variety of radionuclides with energies varying from very low to very high can be incorporated into composite intracavitary sources by sealing multiple multilayered radioactive microspheres of one or several types into an appropriate container; (8) use of low energy intracavitary sources composed of low energy multilayered radioactive microspheres allow selective shielding of adjacent vital structures such as rectum and bladder using relatively thin high atomic weight foils placed over the intracavitary sources or source holders.

The ribbons, wire, plaques and fabric of this invention have the advantages of: (1) multiple multilayered radioactive microspheres provided on a single ribbon allow multiple multilayered radioactive microspheres to be implanted at once by a thin gauge hollow needle by pushing the multilayer radioactive microsphere ribbon out of the tissue-embedded needle with a stylet while withdrawing the needle; (2) the ribbon-multilayered radioactive microspheres of the present invention may be implanted by a very thin 21 or 22-gauge needle; (3) the fabric of this invention self-adheres to the tissues over which it is placed and may be either tissue-absorbable or non-tissue absorbable; (4) the use a fabric containing multiple multilayered radioactive microspheres or microsphere ribbons allows rapid surgical implantation of multiple seeds without need of interstitial needles or a seed gun; and (5) very thin plaques such as optical plaques can be contoured have the appropriate strength and appropriate intensity for effective treatment.

Although a preferred embodiment of the invention has been described with some particularity, many modifications and variations may be made without deviating from the invention. Accordingly, it is to be understood that within the scope of the appended claims, the invention can be practiced other than as expressly described.

What is claimed is:

1. A one-piece substantially spherical seamless multilayered radioactive seed, comprising:
   a microsphere including a central sphere and a layer section with no substantial voids between the central sphere and the layer section;
   said layer section including at least two layers concentric with the central sphere; said layer section being in intimate contact with the outer surface of the central sphere;
   a first layer of said at least two layers being an outer non-radioactive layer;
   at least one of said central sphere and layer section including radioactive material, wherein said microsphere has a therapeutic amount of radioactivity; and
   said microsphere having an outside diameter no greater than 1 millimeter.

2. A one-piece substantially spherical seamless multilayered radioactive seed according to claim 1 in which said layer section includes a second layer and a third layer of said at least two layers, said second layer being a spherical diffusion barrier coat, and said third layer being a spherical coat designed to enhance diagnostic imaging; said first of said at least two layers being a spherical protective coat.

3. A one-piece substantially spherical seamless multilayered radioactive seed according to claim 1 in which said layer section includes a thin outermost special-purpose coat.

4. A one-piece substantially spherical seamless multilayered radioactive seed according to claim 1 in which the seed contains no free spaces or cavities.

5. A one-piece substantially spherical seamless multilayered radioactive seed according to claim 1 in which the seed contains no end-welds.

6. A one-piece substantially spherical seamless multilayered radioactive seed according to claim 1 in which said protective coat is not thicker than 0.20 millimeters thick.

7. A one-piece substantially spherical seamless multilayered radioactive seed according to claim 1 in which the central sphere is an imaging device marker.

8. A one-piece substantially spherical seamless multilayered radioactive seed, comprising:
   a microsphere including a central sphere and a layer section with no substantial voids between the central sphere and the layer section;
   said layer section including at least one layer concentric with the central sphere and in intimate contact with the outer surface of the central sphere;
   at least one of said central sphere and layer section including radioactive material wherein said microsphere has a therapeutic amount of radioactivity;
   said microsphere having an outside diameter no greater than 1 millimeter;
   said layer section further including a spherical coat designed to enhance diagnostic imaging.

9. A one-piece substantially spherical seamless multilayered radioactive seed according to claim 1 further including a radionuclide with a weighted average gamma energy of less than 100 KeV, and with a half-life of less than 130 days, wherein the multilayer radioactive microsphere is a low energy permanent multilayered radioactive microsphere for permanent interstitial implantation into human tumor tissue.

10. A one-piece substantially spherical seamless multilayered radioactive seed according to claim 1 further including a radionuclide with a weighted average gamma energy greater than or equal to 100 KeV and with a half-life of less than 15 to 20 days, wherein the one-piece substantially spherical seamless multilayered radioactive seed is a high energy permanent multilayered radioactive microsphere for permanent interstitial implantation into human tumor tissues.

11. A multilayer radioactive microsphere according to claim 1 in which the layer section includes a radionuclide that has a weighted average gamma energy greater than or equal to 100 KeV, with a half-life of greater than 15 to 20 days, or an average energy less than 100 KeV and a half-life of greater than 130 days, wherein the multilayer radioactive microsphere is a temporary removable multilayered radioactive microsphere for temporary removable interstitial implantation into human tumor tissues.

12. A multilayer radioactive microsphere according to claim 1 in which the layer section includes a radionuclide that emits a high energy electron particle without significant high-energy gamma-ray component, wherein the multilayer radioactive microsphere is an electron-producing or beta multilayered radioactive microsphere for permanent or temporary removable interstitial implantation into human tumor tissue.

13. A multilayer radioactive microsphere according to claim 1 in which said layer section includes a radioactive coat concentric with said central sphere.

14. A multilayer radioactive microsphere according to claim 13 in which the radioactive coat is metalic.

15. A multilayer radioactive microsphere according to claim 13 in which the radioactive coat is a mixture of metals.

16. A multilayer radioactive microsphere according to claim 13 in which the radioactive coat is a dielectric compound.

17. A multilayer radioactive microsphere according to claim 13 in which the radioactive coat is a mixture of compounds.

18. A multilayer radioactive microsphere according to claim 13 in which the radioactive coat is a radionuclide bound to a metal.

19. A multilayer radioactive microsphere according to claim 13 wherein the radioactive coat includes a compound dielectric material containing one non-radioactive and one radioactive component.

20. A multilayer radioactive microsphere according to claim 13 wherein the radioactive coat includes radioactive dielectric compound coat having two or more radioactive components.

21. A multilayer radioactive microsphere according to claim 13 in which the radioactive coat is laminated with a nonradioactive and radioactive materials.

22. A one-piece substantially spherical seamless multilayered radioactive microsphere, comprising:
a microsphere including a central sphere and a layer section with no substantial voids between the central sphere and the layer section;
said layer section including at least one layer concentric with the central sphere and in intimate contact with the outer surface of the central sphere;
said microsphere having a therapeutic amount of radioactivity and an outside diameter no greater than 1 millimeter; the layer section including a radioactive coat; said radioactive coat being uniformly covered by a spherical diffusion barrier.

23. A multilayer radioactive microsphere according to claim 22 wherein the diffusion barrier comprises a metallic coat.

24. A multilayer radioactive microsphere according to claim 23 wherein the metallic coat comprises several layers of metals.

25. A multilayer radioactive microsphere according to claim 23 wherein the metallic coat comprises several layers of compounds and metals.

26. A one-piece substantially spherical seamless multilayered radioactive microsphere, comprising:
a microsphere including a central sphere and a layer section with no substantial voids between the central sphere and the layer section;
said layer section including at least one layer concentric with the central sphere and in intimate contact with the outer surface of the central sphere;
at least one of said central sphere and layer section including radioactive material wherein said microsphere has a therapeutic amount of radioactivity; and
said microsphere having an outside diameter no greater than 1 millimeter wherein the multilayer radioactive microsphere contains an inner spherical uniform coat of a material opaque to imaging rays, wherein the multilayer radioactive microsphere may be imaged by imaging means.

27. The multilayer radioactive microsphere according to claim 1 wherein the layer section is covered by a uniform spherical protective coat.

28. The multilayer radioactive microsphere according to claim 27 wherein the uniform spherical protective coat is composed of a chemically resistant human tissue-compatible metal having sufficiently low atomic weight to minimize X-ray shielding.

29. The multilayer radioactive microsphere according to claim 27 wherein the spherical protective coat is composed of a chemically resistant human tissue-compatible metal compound.

30. The multilayer radioactive microsphere according to claim 27 wherein the spherical protective coat is composed of a resistant human tissue-compatible metal coat less than 0.1 millimeters thick which has a high atomic weight.

31. The multilayer radioactive microsphere according to claim 27 wherein the spherical protective coat is composed of a human tissue-incompatible metal coat which is covered by a tissue-compatible thin coat, whereby a tissue-compatible outermost coat applied over the protective spherical metal coat permits more toxic but low atomic weight metals to be used as the spherical protective coat.

32. The multilayer radioactive microsphere according to claim 27 wherein the tissue-compatible thin coat is sputtered diamond.

33. The multilayer radioactive microsphere according to claim 27 wherein the tissue-compatible thin coat is platinum.

34. The multilayer radioactive microsphere according to claim 27 wherein the outermost thin coat consists of a special-purpose coat designed to enhance physical properties of the seed, whereby the seed may have its hardness, and corrosion resistance increased.

35. The multilayer radioactive microsphere according to claim 27 wherein the outermost thin coat consists of a thin layer used to produce different seed identification colors.

36. The multilayer radioactive microsphere according to claim 1 which has a diameter no greater than 0.40 millimeters to permit interstitial tissue implantation by a needle having a size no larger than 20-G.

37. The multilayer radioactive microsphere according to claim 1 wherein the multilayer radioactive microsphere contains no more than 1,000 millicuries of activity.

38. The multilayer radioactive microsphere according to claim 1 wherein the multilayer radioactive microsphere produces a completely spherical photon fluence without significant anisotropy.

39. A one-piece substantially spherical seamless multilayer radioactive seed, comprising:
a microsphere including a central sphere and a layer section with no substantial voids between the central sphere and the layer section;
said layer section including at least one layer concentric with the central sphere and in intimate contact with the outer surface of the central sphere;
at least one of said central sphere and layer sections including radioactive material, wherein said microsphere includes a therapeutic amount of radioactivity; and
said microsphere including a significant amount of ferromagnetic material wherein the sphere may be moved by an externally applied electromagnetic field and apply a therapeutic amount or radioactivity to tissue;
said microsphere having a diameter of between 1 millimeter and 9 millimeters.

40. A one-piece substantially spherical seamless multilayered radioactive microsphere, comprising:
a microsphere including a central sphere and a layer section with no substantial voids between the central sphere and the layer section;
said layer section including at least one layer concentrical with the central sphere and in intimate contact with the outer surface of the central sphere;
said microsphere has a therapeutic amount of radioactivity and an outside diameter no greater than 1 millimeter;
said microsphere having a ferromagnetic alloy that is capable of being inductively heated in situ by applied radiofrequency radiation until it passes through a Curie transition at temperatures useful for clinical hyperthermia.

41. A ribbon-multilayer radioactive unit having a plurality of substrate radioactive microspheres with outer diameters between 0.04 and 0.8 millimeters attached to a ribbon.

42. A multilayered seamless radioactive wire, comprising:
a central wire section and a layer section;
said layer section including at least three layers coaxial with the central wire section, said layer section being in intimate contact with the outer surface of the central wire section;
at least one of said central wire section and layer section including radioactive material, wherein said wire has a therapeutic amount of radioactivity; and
said wire having an outside diameter no greater than 1 millimeter.

43. A one-piece seamless multilayered radioactive ocular applicator, comprising:
a substrate section and a layer section;
said layer section including at least one layer in intimate contact with a surface of the substrate section;
said applicator having a surface curved adapted to conform to a portion of the eye and containing a therapeutic amount of radioactivity in which radioactive multilayers in the layer section having a thickness no greater than 0.5 millimeters.

44. A radioactive applicator comprising:
surgical factor containing multiple evenly-spaced multilayer radioactive microspheres; each of said microspheres being a one-piece substantially spherical seamless multilayered radioactive seed having a central sphere and a layer section;
said layer section including at least one layer concentric with the central sphere and in intimate contact with the outer surface of the central sphere;
at least one of said central sphere and layer section including radioactive material, wherein said microsphere has a therapeutic amount of radioactivity; and
said microsphere having an outside diameter no greater than 1 millimeter.

45. A radioactive applicator according to claim 44 in which said surgical fabric is tissue absorbable.

46. A miniturized intracavitary source comprising:
a container having thin walls;
a plurality of one-piece substantially spherical seamless multilayered radioactive seeds within said container; at least certain of said seeds including a central sphere and a layer section;
said layer section including at least one layer concentric with the central sphere and in intimate contact with the outer surface of the central sphere;
certain of said seeds having a therapeutic amount of radioactivity selected to cooperate with certain other of said seeds in said container and an outside diameter no greater than 1 millimeter; and
said intracavitary source having an active length of between 10 millimeters and 40 millimeters.

47. An intracavitary applicator, comprising:
a container having thin wall;
said contained having an internal compartment with an internal diameter less than 1 millimeter and a length larger than 10 millimeters;
said container including a closure wherein the container is adapted to receive and confine a plurality of removable radioactive elements for afterloading.

48. An intracavitary applicator according to claim 48 further including a plurality of one-piece substantially spherical seamless multilayered radioactive seeds having selected radioactivities whereby the container may be loaded to serve as a cervical intercavity applicator;
each of said microspheres including a central sphere and a layer section;
said layer section including at least one layer concentric with the central sphere and in intimate contact with the outer surface of the central sphere;
at least one of said central sphere and layer section including radioactive material, wherein said microspheres having a therapeutic amount of radioactivity;
said microspheres having an outside diameter no greater than 1 millimeter; and
said applicator having an active length of between 10 millimeters and 40 millimeters.

49. A ribbon-multilayer radioactive unit according to claim 41 in which both the ribbon and the substrate microspheres have an outer coat of the same material.

50. A one-piece substantially spherical seamless multilayered radioactive seed, comprising:
a microsphere including a central sphere and a layer section with no substantial voids between the central sphere and the layer section;
said layer section including at least one radioactive layer concentric with the central sphere, said radioactive layer having a peak-to-valley height variation that does not exceed plus or minus 400 angstroms; and said microsphere has a therapeutic amount of radioactivity and an outside diameter no greater than 1 millimeter.

51. A ribbon-multilayer radioactive unit having a plurality of substrate radioactive microspheres with outer diameters between 0.04 and 0.08 millimeters attached to a ribbon; said microspheres having a radioactive layer; said radioactive layer having a peak-to-valley height variation that does not exceed plus or minus 400 angstroms.

52. A multilayered seamless radioactive wire, comprising:

a central wire section and a layer section;

said layer section including at least one radioactive layer coaxial with the central wire section; said radioactive layer having a peak-to-valley height variation that does not exceed plus or minus 400 angstroms; and said wire having a therapeutic amount of radioactivity and an outside diameter no greater than 1 millimeter.

53. A one-piece seamless multilayered radioactive ocular applicator, comprising:

a substrate section and a layer section;

said layer section including at least one radioactive layer, said radioactive layer having a peak-to-valley height variation that does not exceed plus or minus 400 angstroms; and said applicator having a therapeutic amount of radioactivity in which radioactive multilayers in the layer section having a thickness no greater than 0.5 millimeters.

54. A radioactive applicator, comprising:

surgical fabric containing multiple evenly-spaced multilayer radioactive microspheres; each of said microspheres being a one-piece substantially spherical seamless multilayered radioactive seed having a central sphere and a layer section; said layer section being in intimate contact with the outer surface of said central sphere;

said layer section including at least one radioactive layer concentric with the central sphere; said radioactive layer having a peak-to-valley height variation that does not exceed plus or minus 400 angstroms; and said microsphere having a therapeutic amount of radioactivity and an outside diameter no greater than 1 millimeter.

55. A miniturized intracavitary source, comprising:

a container having thin walls;

a plurality of one-piece substantially spherical seamless multilayered radioactive seeds within said container; at least certain of said seeds including a central sphere and a layer section;

said layer section including at least one radioactive layer concentric with the central sphere; said radioactive layer having a peak-to-valley height variation that does not exceed plus or minus 400 angstroms;

certain of said seeds having a therapeutic amount of radioactivity selected to cooperate with certain other of said seeds in said container and an outside diameter no greater than 1 millimeter; and said intracavitary source having an active length of between 10 millimeters and 40 millimeters.

* * * * *